United States Patent
Goel et al.

(10) Patent No.: US 10,190,174 B2
(45) Date of Patent: Jan. 29, 2019

(54) ULCERATIVE COLITIS (UC)-ASSOCIATED COLORECTAL NEOPLASIA MARKERS

(71) Applicant: BAYLOR RESEARCH INSTITUTE, Dallas, TX (US)

(72) Inventors: Ajay Goel, Dallas, TX (US); Yuji Toiyama, Mie (JP); C. Richard Boland, Dallas, TX (US); Yoshinaga Okugawa, Mie (JP)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 15/672,778

(22) Filed: Aug. 9, 2017

(65) Prior Publication Data

US 2018/0030545 A1 Feb. 1, 2018

Related U.S. Application Data

(63) Continuation of application No. 14/777,414, filed as application No. PCT/US2014/025976 on Mar. 13, 2014, now Pat. No. 9,758,835.

(60) Provisional application No. 61/787,670, filed on Mar. 15, 2013, provisional application No. 61/941,366, filed on Feb. 18, 2014.

(51) Int. Cl.
| | |
|---|---|
| *C12Q 1/68* | (2018.01) |
| *C12Q 1/6886* | (2018.01) |
| *A61B 1/31* | (2006.01) |
| *A61B 10/00* | (2006.01) |
| *A61B 10/04* | (2006.01) |

(52) U.S. Cl.
CPC .............. *C12Q 1/6886* (2013.01); *A61B 1/31* (2013.01); *A61B 10/007* (2013.01); *A61B 10/0038* (2013.01); *A61B 10/0051* (2013.01); *A61B 10/04* (2013.01); *C12Q 2600/154* (2013.01)

(58) Field of Classification Search
CPC .................. C12Q 1/6886; C12Q 2600/154
USPC ........... 435/6.1, 6.11, 91.1, 91.31, 455, 458; 514/1, 2, 44; 536/23.1, 24.6; 506/16; 600/300, 562
See application file for complete search history.

(56) References Cited

U.S. PATENT DOCUMENTS

| | | | |
|---|---|---|---|
| 2011/0130341 A1 | 6/2011 | Suzuki et al. | 514/19.3 |
| 2012/0094289 A1 | 4/2012 | Garrity-Park et al. | 435/6.11 |

FOREIGN PATENT DOCUMENTS

| | | |
|---|---|---|
| EP | 2295598 | 3/2011 |
| WO | WO 2012/047899 | 4/2012 |

OTHER PUBLICATIONS

Balaguer et al., "Colorectal Cancers with Microsatellite Instability Display Unique miRNA Profiles," *Clin. Cancer Res.*, 2011; 17(19): 6239-6249.
Belaguer, et al, "Epigenetic silencing of miR-137 is an early event in colorectal carcinogenesis", *Cancer Res*, 70(16): 6609-18, 2010.
Brentnall, et al, "Mutations in the p53 gene: an early marker of neoplastic progression in ulcerative colitis", *Gastroenterology*. 107:369-78, 1994.
Calin, et al., "MicroRNA signatures in human cancers", *Nat Rev Cancer.* 6:857-66, 2006.
Claus, et al. "Decitabine induces very early in vivo DNA methylation changes in blasts from patients with acute myeloid leukemia", *Leuk Res*, 37(2): 190-6, 2012.
Deng et al., "MicroRNA-124a and microRNA-34b/c are frequently methylated in all histological types of colorectal cancer and polyps, and in the adjacent normal mucosa," *Oncology Lett.*, 2011; 2: 175-180.
Eaden, et al, "The risk of colorectal cancer in ulcerative colitis: a meta-analysis", *Gut.* 48:526-35, 2001.
Extended European Search Report issued for European Application No. 14768369.2, dated Oct. 21, 2016.
Fujii, et al., "Efficacy of surveillance and molecular markers for detection of ulcerative colitis-associated colorectal neoplasia", *J Gastroenterol.* 38:1117-25,2003.
Hata, et al., "Earlier surveillance colonoscopy programme improves survival in patients with ulcerative colitis associated colorectal cancer: results of a 23-year surveillance programme in the Japanese population", *Br J Cancer.* 89:1232-6,2003.
Hsieh, et al., "Hypermethylation of the p16INK4a promoter in colectomy specimens of patients with long-standing and extensive ulcerative colitis", *Cancer Res.* 58:3942-5, 1998.
International Search Report and Written Opinion issued in PCT/US14/25976, dated Jun. 6, 2014.
Iorio, et al., "MicroRNAs in cancer: small molecules with a huge impact", *J Clin Oncol.* 27:5848-56, 2009.
Issa, "Aging, DNA methylation and cancer", *Crit Rev Oncol Hematol.* 32:31-43, 1999.
Itzkowitz, et al., "Inflammation and cancer IV. Colorectal cancer in inflammatory bowel disease: the role of inflammation", *Am J Physiol Gastrointest Liver Physiol.* 287:G7-17, 2004.
Kanaan et al., "Differential MicroRNA expression tracks neoplastic progression in inflammatory bowel disease-associated colorectal cancer," *Hum. Mutat.*, 2012; 33(5): 551-560.
Kornbluth et al., "Ulcerative colitis practice guidelines in adults (update): American College of Gastroenterology, Practice Parameters Committee", *Am J Gastroenterol.* 105:501-523, 2010.
Laszlo, el al. "Detection and mapping of 5-methylcytosine and 5-hydroxymethylcytosine with nanopore MspA", *Proc Natl Acad Sci USA*. 110:18904-18909, 2013.
Lu, et al., "MicroRNA expression profiles classify human cancers", *Nature.* 435:834-8, 2005.
Maruyama et al. "Emerging links between epigenetic alterations and dysregulation of noncoding RNAs in cancer," *Tumor Biol.* 2012, 33: 277-285.

(Continued)

*Primary Examiner* — Jane J Zara
(74) *Attorney, Agent, or Firm* — Norton Rose Fulbright US LLP

(57) ABSTRACT

Embodiments provide methods and compositions related to detecting neoplasia in ulcerative colitis patients by detection and analysis of the methylation state of miR-1, -9, -124, miR-137 and/or miR-34b/c in samples from UC patients.

19 Claims, 21 Drawing Sheets

Specification includes a Sequence Listing.

(56) References Cited

OTHER PUBLICATIONS

Necela et al., "Differential Expression of MicroRNAs in Tumors from Chronically Inflamed or Genetic (APC(Min/+)) Models of Colon Cancer," *PLoS ONE*, 2011, 6(4): E18501 1-12,.

Pekow, et al., "miR-143 and miR-145 are downregulated in ulcerative colitis: putative regulators of inflammation and proto-oncogenes", *Inflamm Bowel Dis.*, 18(1): 94-100, 2012.

Sato, et al., "Hypermethylation of the p14(ARF) gene in ulcerative colitis-associated colorectal carcinogenesis", *Cancer Res.* 62:1148-51, 2002.

Schreiber, et al. "Error rates for nanopore discrimination among cytosine, methylcytosine, and hydroxymethylcytosine along individual DNA strands", *Proc Natl Acad Sci USA*. 110:18910-18915, 2013.

Toyota, et al., "CpG island methylator phenotype in colorectal cancer", *Proc Natl Acad Sci USA*. 96:8681-6, 1999.

Ullman, et al., "Diagnosis and management of dysplasia in patients with ulcerative colitis and Crohn's disease of the colon", *Inflamm Bowel Dis.* 15:630-8, 2009.

Vogelstein, et al., "Genetic alterations during colorectal-tumor development", *N Engl J Med.* 319:525-32, 1988.

Watanabe, et al., "Predicting ulcerative colitis-associated colorectal cancer using reverse-transcription polymerase chain reaction analysis", *Clin Colorectal Cancer.* 10(2):134-41, 2011.

Watanabe, et al., "RUNX3 copy number predicts the development of UC-associated colorectal cancer", *Int J Oncol.* 38(1):201-7, 2011.

Wu, et al., "MicroRNAs are differentially expressed in ulcerative colitis and alter expression of macrophage inflammatory peptide-2 alpha", *Gastroenterology.* 135:1624-1635 e24, 2008.

Zisman, et al., "Colorectal cancer and dysplasia in inflammatory bowel disease", *J Gastroenterol.* 14:2662-9, 2008.

Partial European Search Report Issued in Corresponding European Application No. 18167786.5, dated May 15, 2018.

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1 gggtgttta gtttagga                                              19

<210> SEQ ID NO 2
<211> LENGTH: 21
<212> TYPE: DNA

<213> ORGANISM: Artificial Sequence
<220> FEATURE:
<223> OTHER INFORMATION: Synthetic Primer

<400> SEQUENCE: 2
tggatttttt tttagggaaa t                                             21

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3 atttttttt agggaaat                                                  18

<210> SEQ ID NO 4
<211> LENGTH: 17
<212> TYPE: DNA
<213> ORGANISM: Artificial Sequence
<220> FEATURE:
<223> OTHER INFORMATION: Synthetic Primer

<400> SEQUENCE: 4 gaagggggaaa ggaaaag                                                 17

<210> SEQ ID NO 5
<211> LENGTH: 16
<212> TYPE: DNA
<213> ORGANISM: Artificial Sequence
<220> FEATURE:
<223> OTHER INFORMATION: Synthetic Primer

<400> SEQUENCE: 5 gaagggggaaa ggaaaa                                                  16

<210> SEQ ID NO 6
<211> LENGTH: 17
<212> TYPE: DNA
<213> ORGANISM: Artificial Sequence
<220> FEATURE:
<223> OTHER INFORMATION: Synthetic Primer

<400> SEQUENCE: 6
ccacacttct cccctttt                                                 17

<210> SEQ ID NO 7
<211> LENGTH: 16
<212> TYPE: DNA
<213> ORGANISM: Artificial Sequence
<220> FEATURE:
<223> OTHER INFORMATION: Synthetic Primer

<400> SEQUENCE: 7
ccacacttct cccctt                                                   16

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
ccaccaaaac tcttactact c                                             21

<210> SEQ ID NO 9
<211> LENGTH: 19
<212> TYPE: DNA
<213> ORGANISM: Artificial Sequence
<220> FEATURE:
<223> OTHER INFORMATION: Synthetic Primer

<400> SEQUENCE: 9
cccaaaaata ccaaacctc                                                19

<210> SEQ ID NO 10
<211> LENGTH: 24
<212> TYPE: DNA
<213> ORGANISM: Artificial Sequence
<220> FEATURE:
<223> OTHER INFORMATION: Synthetic Primer

<400> SEQUENCE: 10
ttyggaggag gtggttggtg ttgt                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tgtagtattt tttagggagt                                               20

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer

<400> SEQUENCE: 12 ggttttgag ggtagagg                                                  18

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
cacccaacct tacaataac                                                19

<210> SEQ ID NO 14
<211> LENGTH: 19
<212> TYPE: DNA
<213> ORGANISM: Artificial Sequence
<220> FEATURE:
<223> OTHER INFORMATION: Synthetic Primer

<400> SEQUENCE: 14
gggtgtttta gttttagga                                                19

<210> SEQ ID NO 15
<211> LENGTH: 16
<212> TYPE: DNA
<213> ORGANISM: Artificial Sequence
<220> FEATURE:

<223> OTHER INFORMATION: Synthetic Primer

<400> SEQUENCE: 15
ccacacttct cccctt                                                          16

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16 tggattttttt tttagggaaa t                                                   21

<210> SEQ ID NO 17
<211> LENGTH: 18
<212> TYPE: DNA
<213> ORGANISM: Artificial Sequence
<220> FEATURE:
<223> OTHER INFORMATION: Synthetic Primer

<400> SEQUENCE: 17
attttttttt agggaaat                                                        18

<210> SEQ ID NO 18
<211> LENGTH: 17
<212> TYPE: DNA
<213> ORGANISM: Artificial Sequence
<220> FEATURE:
<223> OTHER INFORMATION: Synthetic Primer

<400> SEQUENCE: 18 gaagggggaaa ggaaaag                                                        17

<210> SEQ ID NO 19
<211> LENGTH: 16
<212> TYPE: DNA
<213> ORGANISM: Artificial Sequence
<220> FEATURE:
<223> OTHER INFORMATION: Synthetic Primer

<400> SEQUENCE: 19 gaagggggaaa ggaaaa                                                         16

<210> SEQ ID NO 20
<211> LENGTH: 27
<212> TYPE: DNA
<213> ORGANISM: Artificial Sequence
<220> FEATURE:
<223> OTHER INFORMATION: Synthetic Primer

<400> SEQUENCE: 20
aaacacccct aaaaccraac taataac                                              27

<210> SEQ ID NO 21
<211> LENGTH: 18
<212> TYPE: DNA
<213> ORGANISM: Artificial Sequence
<220> FEATURE:
<223> OTHER INFORMATION: Synthetic Primer

<400> SEQUENCE: 21
caccacccaa ccttacaa                                                        18

```
<210> SEQ ID NO 22
<211> LENGTH: 17
<212> TYPE: DNA
<213> ORGANISM: Artificial Sequence
<220> FEATURE:
<223> OTHER INFORMATION: Synthetic Primer

<400> SEQUENCE: 22
ccacacttct ccccttt                                                    17

<210> SEQ ID NO 23
<211> LENGTH: 21
<212> TYPE: DNA
<213> ORGANISM: Artificial Sequence
<220> FEATURE:
<223> OTHER INFORMATION: Synthetic Primer

<400> SEQUENCE: 23
ccaccaaaac tcttactact c                                               21

<210> SEQ ID NO 24
<211> LENGTH: 19
<212> TYPE: DNA
<213> ORGANISM: Artificial Sequence
<220> FEATURE:
<223> OTHER INFORMATION: Synthetic Primer

<400> SEQUENCE: 24
cccaaaaata ccaaacctc                                                  19
```

ULCERATIVE COLITIS (UC)-ASSOCIATED COLORECTAL NEOPLASIA MARKERS

This application is a continuation of U.S. patent application Ser. No. 14/777,414, filed Sep. 15, 2015, which is a national phase application under 35 U.S.C. § 371 of International Application No. PCT/US2014/025976, filed Mar. 13, 2014, which claims priority to U.S. Application No. 61/787,670 filed on Mar. 15, 2013 and U.S. Application No. 61/941,366 filed on Feb. 18, 2014, the entire contents of each of which are hereby incorporated by reference without disclaimer.

This invention was made with government support under grant R01 CA72851 and CA129286 from the National Institutes of Health. The government has certain rights in the invention.

BACKGROUND OF THE INVENTION

1. Field of the Invention

The present invention relates generally to the fields of oncology, molecular biology, cell biology, and medicine. More particularly, it concerns prognosis or treatment of neoplasia or cancer using molecular markers.

2. Description of Related Art

Patients with ulcerative colitis (UC) are at increased risk for developing colorectal cancer (CRC), and the cumulative risk of developing UC-associated CRC increases with the duration and extent of the disease (Eaden 2001; Zisman 2008). Therefore, UC patients who are at high-risk for CRC undergo periodic colonoscopic surveillance with multiple-step biopsies for the earlier diagnosis and treatment of UC-associated colorectal neoplasia (Hata 2003; Kornbluth 2004). However, it is unclear whether current surveillance colonoscopy is effective for early detection, as UC-associated CRC can be difficult to detect endoscopically, and to differentiate from inflammatory regenerative epithelium histologically (Fujii 2003). To improve surveillance efficacy, more effective markers for identifying patients at high risk for UC-associated CRC are needed.

Carcinogenesis in UC occurs in a histologically stepwise manner, sometimes called an "inflammation dysplasia carcinoma sequence" (Vogelstein 1988; Brentnall 1994). Carcinogenetic progression involves accumulation of genetic and epigenetic alterations (Itzkowitz 2004), that can occur in both non-neoplastic and neoplastic epithelium of patients with UC-associated neoplasia; this is referred to as a "field defect" (Hsieh 1998; Sato 2002; Watanabe, *Int J Oncol*; Watanabe, *Clin Colorectal Cancer*). These phenomena suggest that genetic and epigenetic changes in non-neoplastic epithelium could predict development of UC-associated neoplasia. In addition, the genetic features that lead to sporadic CRC—chromosome instability, microsatellite instability, and DNA hypermethylation—also occur in colitis-associated CRC. However, unlike normal colonic mucosa, cells of the inflamed colonic mucosa already have these pre-existing genetic alterations before appearance of s any histologic evidence of dysplasia or cancer. The reasons for these differences are not known, but oxidative stress is likely to be involved (Thomas A. Ullman 2011).

MicroRNAs (miRNAs) are small, non-coding RNAs involved in the regulation of gene expression by either repressing translation or directly cleaving target mRNAs (Iorio 2009). In addition, miRNAs affect pathogenesis of multiple cancer types, including CRC (Lu 2005; Calin 2006). They act as oncogenes or tumor suppressor genes, affecting early-stage carcinogenesis (Calin 2006). Ectopic miRNA expression has been seen in UC mucosa; miRNAs reportedly influence development and progression of UC and UC-associated neoplasia (Wu 2008; Kanaan 2012).

In several types of neoplasia, aberrant methylation of promoter-region CpG islands, as an epigenetic DNA modification, is associated with transcriptional inactivation of tumor suppressor genes; and can result in tumorigenesis. In colon tissues, CpG islands methylated in cancer have been divided into two groups: those that display cancer-restricted methylation (type C), and those that are methylated in (initially) normally aging epithelial cells (type A) (Toyota 1999). Age-related methylation has been proposed to identify and contribute to acquired predispositions to colorectal neoplasia because it parallels age-related increased cancer incidence, and can potentially alter the physiology of aging cells and tissues (Issa 1999).

However, there remains a need to develop a molecular test for neoplasia in UC patients, whose cancers may or may not develop in the same way as non-UC-neoplasia.

SUMMARY OF THE INVENTION

In certain aspects, it was determined for the first time that methylation of one or more of miR-1, -9, -124, -137 and -34b/c in rectal tissues are robust biomarkers for early detection of UC-associated cancer. Embodiments include the use of human miRNAs in human patients.

In certain aspects, methylation of miR-1, -9, -124, -137 and -34b/c in aging colorectal normal epithelium may be used as markers for an early event in UC-associated neoplasia.

Certain embodiments may comprise methods for evaluating dysplasia or cancer risk in a patient or providing a prognosis, which provides a clinician with information useful for surveillance, diagnosis and/or treatment options. Methods involve identifying a patient with UC-associated neoplasia and determining in a sample from the patient whether the sample has increased methylation levels in a gene encoding a biomarker micro RNA such as one, two, or all of miR-1, -9, -137, miR-124 and/or miR-34b/c.

In certain aspects, the methylation levels of the gene may be compared to a control or reference level for the gene. The increased methylation levels may be indicative of a high risk of colorectal dysplasia or cancer. The control may be a normal tissue, a non-cancerous tissue, a non-dysplastic tissue, a non-ulcerative colitis tissue, or the same tissue taken at a point in time before the patient develops ulcerative colitis, dysplasia or cancer. The reference level can be a methylation level of any of the controls or an average of a population of controls or a methylation level of a different gene taken from the same tissue or a different tissue whose methylation level does not change, for example in developing dysplasia or cancer. In some embodiments, methods involve comparing the level of methylation of the at least one biomarker miRNA to the level of methylation of a comparative miRNA to determine a biomarker difference value. A "comparative miRNA" refers to a miRNA whose methylation level is used to evaluate the level of another miRNA in the sample; in some embodiments, the methylation level of a comparative miRNA is used to evaluate a biomarker miRNA methylation level. In some embodiments, the comparative miRNA may refer to a normalized or stable level of methylation.

Embodiments also concern methods and compositions that can be used for evaluating ulcerative colitis, differentiating ulcerative colitis, distinguishing ulcerative colitis, identifying ulcerative colitis as a high risk lesion or inflammation, identifying ulcerative colitis as a low risk lesion or inflammation, identifying tissue having ulcerative colitis as a target for surgical resection or intensive or frequent surveillance, determining tissue having ulcerative colitis that should not be surgically resected, categorizing ulcerative colitis, diagnosing ulcerative colitis, providing a prognosis to a patient regarding ulcerative colitis, evaluating surveillance or treatment options for ulcerative colitis, or treating a patient with ulcerative colitis.

In some embodiments, methods involve determining in a sample from the patient that the sample has increased methylation levels in a gene encoding miR-1, -9, -137, miR-124 and/or miR-34b/c compared to a control or reference methylation level for the gene and identifying the patient as being at a significant risk for developing colon dysplasia or cancer compared to the overall risk for patients with ulcerative colitis.

In certain aspects, the monitoring or surveillance include obtaining a sample. In further aspects, the monitoring or surveillance include testing a sample. The testing may include any diagnosis methods, invasive or non-invasive. For example, the monitoring may include performing endoscopy or employing a screening test for colon cancer. In further embodiments, monitoring may comprise sensitive detection technologies used to measure minimal residual disease (MRD), recurrence and/or resistance for managing or treating cancer patients For UC patients that are determined to be at low risk for colon cancer or dysplasia based on the methylation levels, normal surveillance for colon cancer may be prescribed, provided or recommended, for example, such UC patients may be advised to undergo normal or conventional surveillance, such as colonoscopy and biopsy, wherein biopsy samples may be histologically evaluated for the presence of pre-cancerous changes (colorectal dysplasia) or CRC. The normal or conventional surveillance may be performed every year, one year, two years, three years, four years, five years or within any intermediate time ranges. In addition, conventional UC treatment may be prescribed, provided or recommended.

For UC patients that are determined to be at high risk for colon cancer, intensive surveillance for colon cancer may be prescribed, provided or recommended. The intensive or frequent surveillance may be performed every day, week, month, less than a year or within any intermediate time ranges or at least different from the prescribed normal or conventional surveillance, such as in terms of frequency or intensity (e.g., invasiveness). In addition, colon cancer treatment may be prescribed, provided or recommended for those high-risk UC patients.

In further embodiments, methods involve intensive or frequent surveillance to a patient with ulcerative colitis, for example, comprising performing a colonoscopy on the patient after a sample from the patient is evaluated for increased methylation levels in a gene encoding miR-1, -9, -137, miR-124 and/or miR-34b/c compared to a control or reference methylation level for the gene.

There may also be provided methods for treating a patient with ulcerative colitis. The methods may comprise identifying the patient as having increased methylation levels in a gene encoding miR-1, -9, -124, miR-137, miR-34b and miR-34c compared to a control or reference methylation level for the gene. In a particular embodiment, the methods may comprise administering a treatment that inhibits or reduces the methylation levels in the gene.

These methods can be implemented involving steps and compositions described below in different embodiments.

In certain aspects, methods involve obtaining a sample of a subject or a patient or obtaining a sample from the subject or patient. The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy.

In certain embodiments the sample is obtained from a biopsy from rectal, cecum, or colon tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, intestine, brain, prostate, esophagus, or thyroid tissue.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In certain aspects the sample is obtained from cystic fluid or fluid derived from a tumor or neoplasm. In yet other embodiments the cyst, tumor or neoplasm is in the digestive system. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample. Other steps may or may not include amplifying a nucleic acid in a sample and/or hybridizing one or more probes to an amplified or non-amplified nucleic acid. In certain embodiments, a microarray may be used to measure or assay the level of miRNA methylation in a sample. Non-limiting amplification methods may include reverse transcription (RT), polymerase chain reaction (PCR), real-time PCR (quantitative PCR (q-PCR)), digital PCR, nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art.

There may also be provided methods for assaying nucleic acids in the sample, such as a methylation assay of the promoter in the gene. Measuring or assaying for methylation levels of a miRNA can be accomplished by a variety of different chemical and/or enzymatic reactions that are well known to those of skill in the art. Non-limiting nucleic acid assay methods may include nucleic amplification; polymerase chain reaction; quantitative PCR; RT-PCR; in situ hybridization; Northern hybridization; hybridization protection assay (HPA) (GenProbe); branched DNA (bDNA) assay (Chiron); rolling circle amplification (RCA); single molecule hybridization detection (US Genomics); Invader assay (ThirdWave Technologies); Bridge Litigation Assay (Genaco); next generation sequencing, single-molecule real-time sequencing; nanopore sequencing; mass spectrometry; bisulfite sequencing, combined bisulfite restriction analysis (COBRA); Southern blotting; single nucleotide primer extension (SNuPE); methylation-specific PCR (MSPCR); restriction landmark genomic scanning for methylation (RLGS-M); HpaII-tiny fragment enrichment by ligation-mediated PCR (HELP assay); CpG island microarray; ChIP-chip (chromatin immunoprecipitation-on-chip); ChIP-seq (chromatin immunoprecipitation-sequencing); methylated DNA immunoprecipitation (MeDIP); digital PCR; ddPCR (digital droplet PCR); nCounter (nanoString); BEAMing (Beads, Emulsions, Amplifications, and Magnetics) (Inostics); ARMS (Amplification Refractory Mutation Systems), RNA-Seq; TAm-Seq (Tagged-Amplicon deep sequencing) PAP (Pyrophosphorolysis-activation polymerization, or a microarray-based methylation profiling.

Methods may also include a step of sequencing one or more nucleic acids isolated from a subject or derived from nucleic acids isolated from a subject.

Methods may further involve recording the methylation levels, risk or prognosis in a tangible medium, reporting the methylation levels, risk or prognosis to the patient, a health care payer, a physician, an insurance agent, or an electronic system, monitoring the ulcerative colitis patient for colorectal dysplasia or cancer, and/or comprising determining or administering a treatment for the patient based on the risk within one hour, one day, one week, one month, one year, two years, three years, four years, five years of the measuring or evaluating or within any intermediate time ranges.

There may be provided methods to perform intensive or frequent surveillance to the patient for colorectal dysplasia or cancer or administering a dysplasia or cancer prevention or treatment if the patient has increased methylation levels. Some further embodiments involve normal surveillance for colorectal dysplasia or cancer or administering a dysplasia or cancer prevention or treatment if the patient does not have increased methylation levels. The treatment may comprise inhibiting or reducing the methylation levels in the gene or any traditional cancer therapies, such as surgery, chemotherapy, radiation, gene therapy, or immunotherapy.

In other embodiments, there may be a series of evaluations performed on a sample, For instance, in some embodiments, the cyst may first undergo cytological examination or evaluation prior to implementing any molecular tests.

In some embodiments, methods will involve determining or calculating a diagnostic or risk score based on data concerning the methylation level of one or more miRNAs, meaning that the methylation level of the one or more miRNAs is at least one of the factors on which the score is based. A diagnostic score will provide information about the biological sample, such as the general probability that the ulcerative colitis is a high risk for developing dysplasia or cancer, that the ulcerative colitis is a low risk for developing dysplasia or cancer, or both.

In some embodiments, the diagnostic score represents the probability that the ulcerative colitis is more likely than not either a high risk ulcerative colitis or a low risk ulcerative colitis or a high or low risk for dysplasia, cancer or metastasis. In certain embodiments, a probability value is expressed as a numerical integer or number that represents a probability of 0% likelihood to 100% likelihood that a patient has a particular category of ulcerative colitis, such as a high risk or low risk ulcerative colitis.

In some embodiments, the probability value is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a particular category of ulcerative colitis, such as at risk for dysplasia, cancer or metastasis. Alternatively, the probability may be expressed generally in percentiles, quartiles, or deciles.

A difference between or among weighted coefficients ore methylation levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the methylation values of biomarkers with differential methylation p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the diagnostic score is calculated using one or more statistically significantly differentially expressed biomarkers (either individually or as difference pairs), including, but not limited to, methylation levels in a gene encoding miR-1, -9, -124, miR-137, miR-34b, miR-34c, or a combination thereof.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to methylation levels in a sample from a patient with ulcerative colitis in a gene encoding miR-1, -9, -137, miR-124 and/or miR-34b/c; and b) determining a difference value in the methylation levels using the information corresponding to the methylation levels compared to a control or reference methylation level for the gene.

In some embodiments, receiving information comprises receiving from a tangible data storage device information corresponding to the methylation levels from a tangible storage device. In additional embodiments the medium further comprises computer-readable code that, when executed by a computer, causes the computer to perform one or more additional operations comprising: sending information corresponding to the difference value to a tangible data storage device, calculating a risk score for the patient of developing dysplasia or cancer or metastasis, performing intensive or frequent surveillance to the patient for colorectal dysplasia or cancer or metastasis or administering a dysplasia or cancer or metastasis prevention or treatment if the patient has increased methylation levels, and/or or performing normal surveillance for colorectal dysplasia or cancer or metastasis or administering a dysplasia or cancer or metastasis prevention or treatment if the patient does not have increased methylation levels.

Also provided are kits containing the disclosed compositions or compositions used to implement the disclosed methods. In some embodiments, kits can be used to evaluate one or more miRNA molecules. In certain embodiments, a kit contains, contains at least, or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or any range and combination derivable therein, miRNA probes or primers including those that may specifically hybridize under stringent conditions to miRNAs disclosed herein. In other embodiments, kits or methods may involve 1, 2, or more miRNA probes or primers, which may be capable of specifically detecting any of genes encoding the following miRNAs: miR-1, -9, -124, miR-137, and/or miR-34b/c.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Introduction

Figures 1A, 1B, 1C:
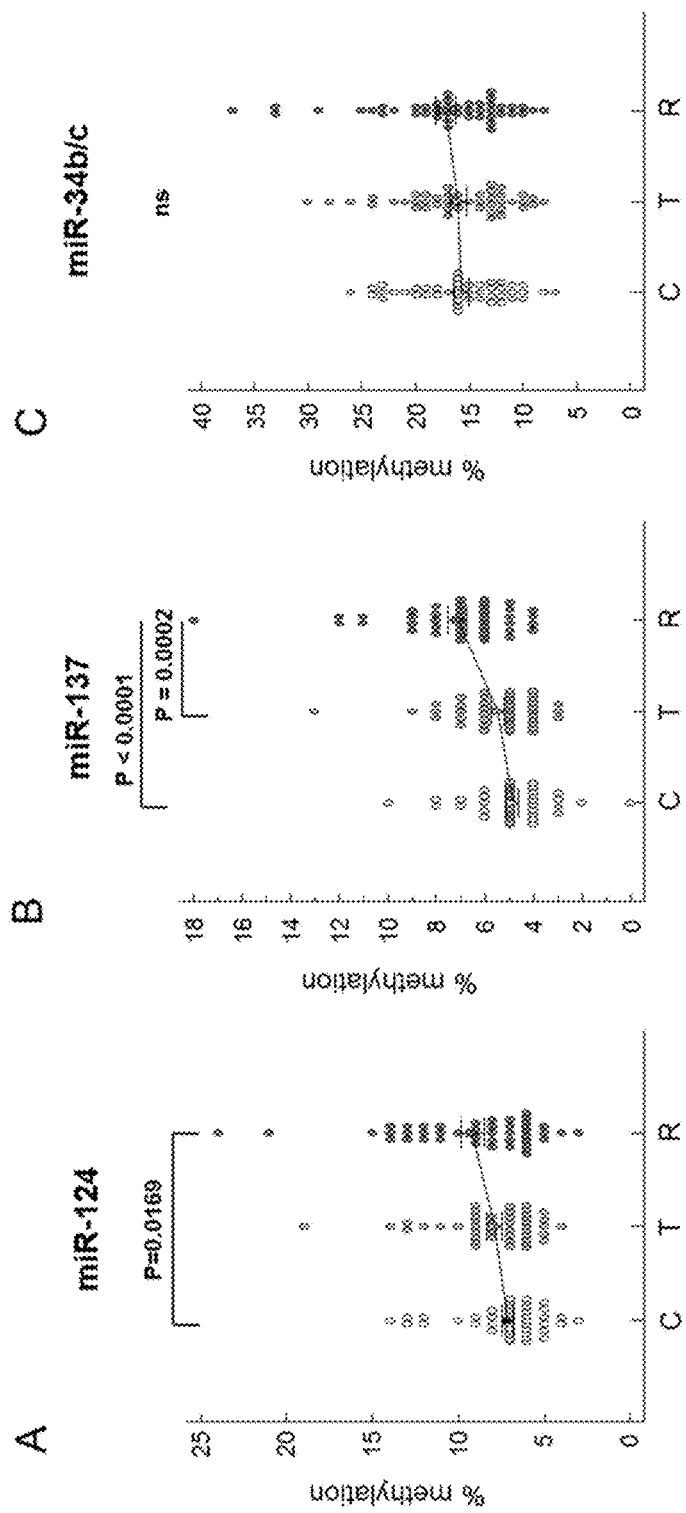
FIG. 1: MiR-124, -137, and -34b/c methylation levels in non-neoplastic UC mucosa. (n=135). (A) Dot plots of miR-124 methylation levels in mucosa at Cecum (C; n=45), Transverse colon (T; n=45) and Rectum (R; n=45). (B) Dot plots of miR-137 methylation levels in mucosa at Cecum (C; n=45), Transverse colon (T; n=45) and Rectum (R; n=45). (C) Dot plots of miR-34b/c methylation levels in mucosa at Cecum (C; n=45), Transverse colon (T; n=45) and Rectum (R; n=45). Statistically significant differences were determined using Mann-Whitney tests and Kruskal-Wallis tests.

In some aspects, the invention generally relates to methods and compositions for evaluation of UC patients or subjects for the risk of developing colon cancer or related diseases or conditions. The methods and compositions may be suitable for treating or monitoring UC subjects at risk for colon cancer or dysplasia with a particular biomarker profile, for example, an increased methylation profile of one or more miRNAs as compared to a reference level or a control sample.

II. Definitions

"Prognosis" refers to as a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis also includes prediction of favorable responses to cancer treatments, such as a conventional cancer therapy.

A neoplasia status may be used to indicate any status related to neoplasia. As used herein, the terms "neoplastic cells" and "neoplasia" may be used interchangeably and refer to cells which exhibit relatively autonomous growth, so that they exhibit an aberrant growth phenotype characterized by a significant loss of control of cell proliferation. Neoplastic cells can be malignant or benign. In particular aspects, a neoplasia includes both dysplasia and cancer. Neoplasms may be benign, pre-malignant (carcinoma in situ or dysplasia) or malignant (cancer). Neoplastic cells may form a lump (i.e., a tumor) or not.

The term "dysplasia" may be used when the cellular abnormality is restricted to the originating tissue, as in the case of an early, in-situ neoplasm. Dysplasia may be indicative of an early neoplastic process. The term "cancer" may refer to a malignant neoplasm, including a broad group of various diseases involving unregulated cell growth.

A neoplasia status that indicates the existence/absence of a neoplasia may be associated with a favorable/poor prognosis, respectively. A favorable or poor prognosis may, for example, be assessed in terms of patient survival, likelihood of disease recurrence or disease metastasis. Patient survival, disease recurrence and metastasis may for example be assessed in relation to a defined time point, e.g. at a given number of years after a cancer treatment (e.g. surgery to remove one or more tumors) or after initial diagnosis. In one embodiment, a favorable or poor prognosis may be assessed in terms of overall survival or disease free survival.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased methylation," ""hypermethylation," "reduced methylation," or "hypomethylation" refers to a methylation level of a biomarker in the subject's sample as compared to a reference level representing the same biomarker or a different biomarker. In certain aspects, the reference level may be a reference level of methylation from a non-cancerous tissue from the same subject. Alternatively, the reference level may be a reference level of methylation from a different subject or group of subjects. For example, the reference level of methylation may be a methylation level obtained from a sample (e.g., a tissue, fluid or cell sample) of a subject or group of subjects without cancer, or a methylation level obtained from a non-cancerous tissue of a subject or group of subjects with cancer. The reference level may be a single value or may be a range of values. The reference level of methylation can be determined using any method known to those of ordinary skill in the art. In some embodiments, the reference level is an average level of methylation determined from a cohort of subjects with cancer or without cancer. The reference level may also be depicted graphically as an area on a graph.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

III. MiRNAs

Recently, methylation of miR-124, -137 and -34b/c was reported to be common in CRCs with "field defects" and to increase with age in non-neoplastic colorectal epithelium (Deng 2011; Balaguer 2010; Lujambio 2007). However, it has never been determined whether the analysis of aging-related miRNA methylation levels in non-neoplastic epithelium can help predict UC-associated CRC. In certain embodiments, microRNAs (abbreviated miRNAs) may be used in methods and compositions for determining the risk of UC patients for having colon cancer or dysplasia. In particular embodiments, the miRNAs may include one, two, or all of miR-1, -9, -124, miR-137, miR-34b, and miR-34c. In certain aspects, the increased methylation level of one or more of these biomarkers indicate a high risk for these patients to have colon cancer or dysplasia.

MiRNAs may be naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression.

There may be three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end.

The cleavage product, the premature miRNA (pre-miRNA) may be about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance toward gaining apoptosis signaling.

In certain embodiments, methods may involve, but not be limited to, next generation sequencing (Lin & Huang 2009; Boerno 2010; Laird 2010; Flusberg 2010; all incorporated herein by reference), single-molecule real-time sequencing (Lin & Huang 2009; Boerno 2010; Laird 2010; Flusberg 2010; all incorporated herein by reference), mass spectrometry (Lin & Huang 2009; Boerno 2010; Laird 2010; Flusberg 2010; all incorporated herein by reference), bisulfite sequencing, combined bisulfite restriction analysis (CO-BRA), Southern blotting, single nucleotide primer extension (SNuPE), methylation-specific PCR (MSPCR), restriction landmark genomic scanning for methylation (RLGS-M), HpaII-tiny fragment enrichment by ligation-mediated PCR (HELP assay), CpG island microarray, ChIP-chip (chromatin immunoprecipitation-on-chip), ChIP-seq (chromatin immunoprecipitation-sequencing), methylated DNA immunoprecipitation (MeDIP), or a microarray-based methylation profiling.

In further embodiments, the methods described herein for methylation detection or single-molecule real-time sequencing methods may further comprise nanopore sequencing (i.e., technologies based on protein nanopores) to detect DNA methylation (Laszlo, et al., 2013; Schreiber, et al., 2013); all incorporated herein by reference).

IV. Ulcerative Colitis

In certain embodiments, subjects or patients are first determined whether they have or are at risk of ulcerative colitis (UC). For example, these subjects or patients are first diagnosed for ulcerative colitis. In further embodiments, if they are determined to have or be at risk for UC, they may be further evaluated for the biological markers, including, but not limited to, methylation levels in a gene encoding miR-1, -9, -124, miR-137, miR-34b, miR-34c, or a combination thereof.

In certain embodiments, ulcerative colitis may be diagnosed with any one or more of the following steps:

A complete blood count is done to check for anemia; thrombocytosis, a high platelet count, is occasionally seen;

Electrolyte studies and renal function tests are done, as chronic diarrhea may be associated with hypokalemia, hypomagnesemia and pre-renal failure;

Liver function tests are performed to screen for bile duct involvement: primary sclerosing cholangitis;

X-ray;

Urinalysis;

Stool culture, to rule out parasites and infectious causes;

Erythrocyte sedimentation rate can be measured, with an elevated sedimentation rate indicating that an inflammatory process is present;

C-reactive protein can be measured, with an elevated level being another indication of inflammation;

Inquiry of risk factors may include: recent cessation of tobacco smoking; recent administration of large doses of iron or vitamin B6; hydrogen peroxide in enemas or other procedures;

Endoscopic;

Histologic.

In particular embodiments, endoscopic diagnosis for UC may include obtaining biopsy sample (H&E stain) that demonstrates marked lymphocytic infiltration (blue/purple) of the intestinal mucosa and architectural distortion of the crypts. In certain aspects, full colonoscopy to the cecum and entry into the terminal ileum may be attempted if diagnosis of UC is unclear. In other aspects, a flexible sigmoidoscopy may be sufficient to support the diagnosis. The physician may elect to limit the extent of the exam if severe colitis is encountered to minimize the risk of perforation of the colon. Endoscopic findings in ulcerative colitis may include the following: Loss of the vascular appearance of the colon; Erythema (or redness of the mucosa) and friability of the mucosa; Superficial ulceration, which may be confluent, and Pseudopolyps. Ulcerative colitis is usually continuous from the rectum, with the rectum almost universally being involved. There is rarely perianal disease, but cases have been reported. The degree of involvement endoscopically ranges from proctitis or inflammation of the rectum, to left sided colitis, to pancolitis, which is inflammation involving the ascending colon.

Biopsies of the mucosa may be taken to definitively diagnose UC and differentiate it from Crohn's disease, which is managed differently clinically. Microbiological samples may be taken at the time of endoscopy. The pathology in ulcerative colitis may involve distortion of crypt architecture, inflammation of crypts (cryptitis), frank crypt abscesses, and hemorrhage or inflammatory cells in the lamina propria. In cases where the clinical picture is unclear, the histomorphologic analysis may be used in determining the diagnosis and thus the management. By contrast, a biopsy analysis may be indeterminate, and thus the clinical progression of the disease may be used to inform its treatment.

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra).

In certain instances, with respect to UC, the variability of symptoms reflect differences in the extent of disease (i.e., the amount of the colon and rectum that are inflamed) and the intensity of inflammation. Disease starts at the rectum and moves "up" the colon to involve more of the organ. UC can be categorized by the amount of colon involved. Typically, patients with inflammation confined to the rectum and a short segment of the colon adjacent to the rectum have milder symptoms and a better prognosis than patients with more widespread inflammation of the colon.

The different types of ulcerative colitis may be classified according to the location and the extent of inflammation. As used herein in reference to UC, the term "clinical subtype" includes a classification of UC defined by a set of clinical criteria that distinguish one classification of UC from another. As non-limiting examples, subjects with UC can be classified as having ulcerative proctitis, proctosigmoiditis, left-sided colitis, pancolitis, fulminant colitis, and combinations thereof. Criteria relating to these subtypes have been described, for example, in Kornbluth et al., 2004.

Ulcerative proctitis is a clinical subtype of UC defined by inflammation that is limited to the rectum. Proctosigmoiditis is a clinical subtype of UC which affects the rectum and the sigmoid colon. Left-sided colitis is a clinical subtype of UC which affects the entire left side of the colon, from the rectum to the place where the colon bends near the spleen and begins to run across the upper abdomen (the splenic flexure). Pancolitis is a clinical subtype of UC which affects the entire colon. Fulminant colitis is a rare, but severe form of pancolitis. Patients with fulminant colitis are extremely ill with dehydration, severe abdominal pain, protracted diarrhea with bleeding, and even shock.

In some embodiments, classification of the clinical subtype of UC may be used in planning an effective course of treatment. While ulcerative proctitis, proctosigmoiditis, and left-sided colitis can be treated with local agents introduced through the anus, including steroid-based or other enemas and foams, pancolitis must be treated with oral medication so that active ingredients can reach all of the affected portions of the colon.

One skilled in the art understands that overlap can exist between clinical subtypes of UC and that a subject having UC can have more than one clinical subtype of UC. Similarly, the biological markers described herein can be associated with more than one clinical subtype of UC.

V. Nucleic Acid Assays

It is contemplated that a number of assays could be employed to analyze miRNA in biological samples. Such assays include, but are not limited to, array hybridization, solution hybridization, nucleic amplification, polymerase chain reaction, quantitative PCR, RT-PCR, in situ hybridization, Northern hybridization, hybridization protection assay (HPA) (GenProbe), digital PCR, ddPCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seq (Tagged-Amplicon deep sequencing) PAP (Pyrophosphorolysis-activation polymerization, branched DNA (bDNA) assay (Chiron), rolling circle amplification (RCA), single molecule hybridization detection (US Genomics), invader assay (ThirdWave Technologies), and/or Oligo Ligation Assay (OLA), hybridization, and array analysis. U.S. patent application Ser. No. 11/141,707, filed May 31, 2005; Ser. No. 11/857,948, filed Sep. 19, 2007; Ser. No. 11/273,640, filed Nov. 14, 2005 and provisional patent application 60/869,295, filed Dec. 8, 2006 are incorporated by reference in their entirety.

A. Isolation of Nucleic Acids

Nucleic acids may be isolated using techniques well known to those of skill in the art, though in particular embodiments, methods for isolating small nucleic acid molecules, and/or isolating RNA molecules can be employed.

Chromatography is a process often used to separate or isolate nucleic acids from protein or from other nucleic acids. Such methods can involve electrophoresis with a gel matrix, filter columns, alcohol precipitation, and/or other chromatography.

If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix may be prepared using polyacrylamide, though agarose can also be used. The gels may be graded by concentration or they may be uniform. Plates or tubing can be used to hold the gel matrix for electrophoresis. For example, one-dimensional electrophoresis may be employed for the separation of nucleic acids. Plates may be used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased.

Methods may involve the use of organic solvents and/or alcohol to isolate nucleic acids, particularly miRNA used in methods and compositions disclosed herein. Some embodiments are described in U.S. patent application Ser. No. 10/667,126, which is hereby incorporated by reference.

In certain aspects, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column may work particularly well for such isolation procedures.

B. Amplification

Many methods exist for evaluating miRNA levels by amplifying all or part of miRNA nucleic acid sequences such as mature miRNA, precursor miRNAs, and/or primary miRNAs. Suitable nucleic acid polymerization and amplification techniques include reverse transcription (RT), polymerase chain reaction (PCR), real-time PCR (quantitative PCR (q-PCR)), digital PCR, ddPCR (digital droplet PCR), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method may be used, such as reverse transcription followed by real time PCR (Chen et al., 2005 and/or U.S. patent application Ser. No. 11/567,082, filed Dec. 5, 2006, which are incorporated herein by reference in its entirety).

An exemplary PCR reaction includes multiple amplification steps, or cycles that selectively amplify target nucleic acid species. An exemplary reaction includes three steps: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Exemplary PCR reactions may include 20 or more cycles of denaturation, annealing, and elongation. In many cases, the annealing and elongation steps can be performed concurrently, in which case the cycle contains only two steps. Since mature miRNAs are single stranded, a reverse transcription reaction (which produces a complementary cDNA sequence) is performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length or any range derivable therein. In additional embodiments, a primer is at least 35 nucleotides in length.

In a further aspect, a forward primer can comprise at least one sequence that anneals to a target miRNA and alternatively can comprise an additional 5' noncomplementary region. In another aspect, a reverse primer can be designed to anneal to the complement of a reverse transcribed miRNA. The reverse primer may be independent of the miRNA sequence, and multiple miRNAs may be amplified using the same reverse primer. Alternatively, a reverse primer may be specific for a miRNA.

In some embodiments, two or more miRNAs or nucleic acids are amplified in a single reaction volume or multiple reaction volumes. In certain aspects, one or more miRNA or nucleic may be used as a normalization control or a reference nucleic acid for normalization. Normalization may be performed in separate or the same reaction volumes as other amplification reactions.

One aspect includes multiplex q-PCR, such as qRT-PCR, which enables simultaneous amplification and quantification of at least one miRNA of interest and at least one reference nucleic acid in one reaction volume by using more than one pair of primers and/or more than one probe. The primer pairs may comprise at least one amplification primer that uniquely binds each nucleic acid, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

A single combined reaction for q-PCR, may be used to: (1) decrease risk of experimenter error, (2) reduce assay-to-assay variability, (3) decrease risk of target or product contamination, and (4) increase assay speed. The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341).

To assess the expression of miRNAs, real-time RT-PCR detection can be used to screen nucleic acids or RNA isolated from samples of interest and a related reference such as, but not limited to a normal adjacent tissue (NAT) samples.

A panel of amplification targets may be chosen for real-time RT-PCR quantification. In one aspect, the panel of targets includes one or more miRNA described herein. The selection of the panel or targets can be based on the results of microarray expression analyses, such as with mirVana™ miRNA Bioarray V1 (Ambion), Human miRNA Microarrays (V3) (Agilent), miRLink™ Arrays (Asuragen), or any other suitable microarray.

One example of a normalization target is 5S rRNA and others can be included. Reverse transcription (RT) reaction components may be assembled on ice prior to the addition of RNA template. Total RNA template may be added and mixed. RT reactions may be incubated in an appropriate PCR System at an appropriate temperature (such as 15-30° C., including all values and ranges there between) for an appropriate time, 15 to 30 minutes or longer, then at a temperature of 35 to 42 to 50° C. for 10 to 30 to 60 minutes, and then at 80 to 85 to 95° C. for 5 minutes, then placed on wet ice. Reverse Transcription reaction components may include nuclease-free water, reverse transcription buffer, dNTP mix, RT Primer, RNase Inhibitor, Reverse Transcriptase, and RNA.

Following assembly of the PCR reaction components a portion of the RT reaction is transferred to the PCR mix. PCR reactions may be incubated in an PCR system at an elevated temperature (e.g., 95° C.) for 1 minute or so, then for a number of cycles of denaturing, annealing, and extension (e.g., 40 cycles of 95° C. for 5 seconds and 60° C. for 30 seconds). Results can be analyzed, for example, with SDS V2.3 (Applied Biosystems). Real-time PCR components may include Nuclease-free water, $MgCl_2$, PCR Buffer, dNTP mix, one or more primers, DNA Polymerase, cDNA from RT reaction and one or more detectable label.

Software tools such as NormFinder (Andersen et al., 2004) may be used to determine targets for normalization with the targets of interest and tissue sample set. For normalization of the real-time RT-PCR results, the cycle threshold ($C_t$) value (a log value) for the microRNA of interest is subtracted from the geometric mean $C_t$ value of normalization targets. Fold change can be determined by subtracting the $dC_t$ normal reference (N) from the corresponding $dC_t$ sample being evaluated (T), producing a $ddC_t$(T-N) value for each sample. The average $ddC_t$(T-N) value across all samples is converted to fold change by $2^{ddCt}$. The representative p-values are determined by a two-tailed paired Student's t-test from the $dC_t$ values of sample and normal reference.

There may be provided methods for using digital PCR. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in the method of measuring nucleic acids amounts, with the former being a more precise method than PCR. PCR carries out one reaction per single sample. dPCR also carries out a single reaction within a sample, however the sample is separated into a large number of partitions and the reaction is carried out in each partition individually. This separation allows a more reliable collection and sensitive measurement of nucleic acid amounts. The method has been demonstrated as useful for studying variations in gene sequences—such as copy number variants and point mutations—and it is routinely used for clonal amplification of samples for "next-generation sequencing."

For example in digital PCR, a sample is partitioned so that individual nucleic acid molecules within the sample are localized and concentrated within many separate regions. (The capture or isolation of individual nucleic acid molecules has been effected in micro well plates, capillaries, the dispersed phase of an emulsion, and arrays of miniaturized chambers, as well as on nucleic acid binding surfaces.) The partitioning of the sample allows one to estimate the number of different molecules by assuming that the molecule population follows the Poisson distribution. As a result, each part will contain "0" or "1" molecules, or a negative or positive reaction, respectively. After PCR amplification, nucleic acids may be quantified by counting the regions that contain PCR end-product, positive reactions. In conventional PCR, the number of PCR amplification cycles is proportional to the starting copy number. dPCR, however, is not dependent on the number of amplification cycles to determine the initial sample amount, eliminating the reliance on uncertain exponential data to quantify target nucleic acids and therefore provides absolute quantification.

C. Nucleic Acid Arrays

Certain aspects concern the preparation and use of miRNA arrays or miRNA probe arrays, which are ordered macroarrays or microarrays of nucleic acid molecules (probes) that are fully or nearly complementary or identical to a plurality of miRNA molecules or precursor miRNA molecules and are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO 0138580; WO 0168255; WO 03020898; WO 03040410; WO 03053586; WO 03087297; WO 03091426; WO 03100012; WO 04020085; WO 04027093; EP 373 203; EP 785 280; EP 799 897 and UK 8 803 000; the disclosures of which are all herein incorporated by reference. Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

Some embodiments involve the preparation and use of miRNA arrays or miRNA probe arrays, which are ordered macroarrays or microarrays of nucleic acid molecules (probes) that are fully or nearly complementary or identical to a plurality of miRNA molecules or precursor miRNA molecules and that are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass, metal, plastic, and silicon. Such arrays may vary in a number of different ways, including average probe length, sequence or types of probes, nature of bond between the probe and the array surface, e.g. covalent or non-covalent, and the like. The labeling and screening methods are not limited by with respect to any parameter except that the probes detect miRNA; consequently, methods and compositions may be used with a variety of different types of miRNA arrays.

Representative methods and apparatuses for preparing a microarray have been described, for example, in U.S. Pat. Nos. 5,143,854; 5,202,231; 5,242,974; 5,288,644; 5,324, 633; 5,384,261; 5,405,783; 5,412,087; 5,424,186; 5,429, 807; 5,432,049; 5,436,327; 5,445,934; 5,468,613; 5,470, 710; 5,472,672; 5,492,806; 5,525,464; 5,503,980; 5,510, 270; 5,525,464; 5,527,681; 5,529,756; 5,532,128; 5,545, 531; 5,547,839; 5,554,501; 5,556,752; 5,561,071; 5,571, 639; 5,580,726; 5,580,732; 5,593,839; 5,599,695; 5,599, 672; 5,610;287; 5,624,711; 5,631,134; 5,639,603; 5,654, 413; 5,658,734; 5,661,028; 5,665,547; 5,667,972; 5,695, 940; 5,700,637; 5,744,305; 5,800,992; 5,807,522; 5,830, 645; 5,837,196; 5,871,928; 5,847,219; 5,876,932; 5,919, 626; 6,004,755; 6,087,102; 6,368,799; 6,383,749; 6,617, 112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000, which are each herein incorporated by reference.

It is contemplated that the arrays can be high density arrays, such that they contain 2, 20, 25, 50, 80, 100, or more, or any integer derivable therein, different probes. It is contemplated that they may contain 1000, 16,000, 65,000, 250,000 or 1,000,000 or more, or any integer or range derivable therein, different probes. The probes can be directed to targets in one or more different organisms or cell types. In some embodiments, the oligonucleotide probes may range from 5 to 50, 5 to 45, 10 to 40, 9 to 34, or 15 to 40 nucleotides in length. In certain embodiments, the oligonucleotide probes are 5, 10, 15, 20, 25, 30, 35, 40 nucleotides in length, including all integers and ranges there between.

Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed herein or may be found in, for example, WO 9743450; WO 03023058; WO 03022421; WO 03029485; WO 03067217; WO 03066906; WO 03076928; WO 03093810; WO 03100448A1, all of which are specifically incorporated by reference.

D. Hybridization

After an array or a set of miRNA probes is prepared and the miRNA in the sample is labeled, the population of target nucleic acids may be contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in many embodiments is the use of stringent conditions during hybridization. Stringent conditions are known to those of skill in the art.

E. Labels and Labeling Techniques

In some embodiments, methods concern miRNA that are directly or indirectly labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments, the label is non-radioactive. Generally, nucleic acids may be labeled by adding labeled nucleotides (one-step process) or adding nucleotides and labeling the added nucleotides (two-step process).

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides may be catalytically added to a miRNA, and the unlabeled nucleotide is modified with a chemical moiety that enables it to be subsequently labeled. In some embodiments, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNA is how to label the already existing molecule. In some methods, embodiments concern the use of an enzyme capable of using a di- or tri-phosphate ribonucleotide or deoxyribonucleotide as a substrate for its addition to a miRNA. Moreover, in specific embodiments, it involves using a modified di- or tri-phosphate ribonucleotide, which is added to the 3' end of a miRNA. The source of the enzyme is not limiting. Examples of sources for the enzymes include yeast, gram-negative bacteria such as *E. coli, Lactococcus lactis*, and sheep pox virus.

Enzymes capable of adding such nucleotides include, but are not limited to, poly(A) polymerase, terminal transferase, and polynucleotide phosphorylase. In specific embodiments, a ligase is contemplated as not being the enzyme used to add the label, and instead, a non-ligase enzyme is employed. Terminal transferase catalyzes the addition of nucleotides to the 3' terminus of a nucleic acid. Polynucleotide phosphorylase can polymerize nucleotide diphosphates without the need for a primer.

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phycoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

A number of techniques for visualizing or detecting labeled nucleic acids are readily available. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acid. Furthermore, a person of ordinary skill in the art is well aware of ways of visualizing, identifying, and characterizing labeled nucleic acids, and accordingly, such protocols may be used as part of some embodiments. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

VI. Methylation Determination

In certain aspects, there may be provided methods for determining methylation information of one or more methylation biomarkers in a sample of cells from a subject with cancer. The methylation information may be obtained by testing cancer samples by a lab, a technician, a device, or a clinician or may be determined by any method known in the art.

A. Determining Methylation

Any method for detecting DNA methylation can be used. In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Patent Publication No. 2004/0132048. Alternatively, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and Ser. No. 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al. (1996); DeGraves et al. (2003); Deiman et al. (2002). Amplifications may be monitored in "real time."

Additional methods for detecting DNA methylation can involve genomic sequencing before and after treatment of the DNA with bisulfite. See, e.g., Frommer et al. (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby (1996); Xiong & Laird (1997).

In some embodiments, a MethyLight assay is used alone or in combination with other methods to detect DNA methylation (see, Eads et al., 1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, 1997). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA. See, Herman et al. (1996); U.S. Pat. No. 5,786,146.

Additional methylation detection methods include, but are not limited to, methylated CpG island amplification (see, Toyota et al., 1999) and those described in, e.g., U.S. Patent Publication 2005/0069879; Rein et al. (1998); Olek et al. (1997); and PCT Publication No. WO 00/70090.

Additional embodiments may include methods for measuring nucleic acids, including digital PCR, ddPCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seg (Tagged-Amplicon deep sequencing) PAP (Pyrophosphorolysis-activation polymerization, B. Determining Gene and Protein Expression It is well known that methylation of genomic DNA can affect expression (transcription and/or translation) of nearby gene sequences. Therefore, in some embodiments, the methods include the step of correlating the methylation status of at least one cytosine in a DNA region of the methylation biomarkers as described above with the expression of nearby coding sequences. For example, expression of gene sequences within about 1.0 kb, 1.5 kb, 2.0 kb, 2.5 kb, 3.0 kb, 3.5 kb or 4.0 kb in either the 3' or 5' direction from the cytosine of interest in the DNA region can be detected. In some embodiments, the gene or protein expression of one or more methylation biomarkers is compared to a control, for example, the methylation status in the DNA region and/or the expression of a nearby gene sequence from a sample from an individual known to be negative for cancer or known to be positive for cancer, or to an expression level that distinguishes between cancer and noncancer states. Such methods, like the methods of detecting methylation described herein, are useful in providing diagnosis, prognosis, etc., of cancer. Methods for measuring transcription and/or translation of a particular gene sequence are well known in the art. See, for example, Ausubel, *Current Protocols in Molecular Biology*, 1987-2006, John Wiley & Sons; and Sambrook and Russell, *Molecular Cloning: A Laboratory Manual*, 3rd Edition, 2000.

In some embodiments, the methods further comprise the step of correlating the methylation status and expression of one or more of the gene regions of the one or more methylation biomarkers as describe above.

Certain aspects of the present invention thus provides for detection of gene (e.g. RNA) and/or protein expression to detect cancer, particularly brain cancer. RNA or protein expression from the genomic regions described herein can be compared to a reference level or otherwise normal expression (e.g., expression for normal, non-cancerous tissue) to detect cancer, particularly brain cancer. In some embodiments, methylation biomarker expression is detected and compared to a reference value or otherwise normal expression (i.e., expression for normal, non-cancerous tissue) of methylation biomarker.

Any method of detecting RNA or protein expression can be used in the methods of certain aspects of the invention. In some embodiments, the presence of cancer is evaluated by determining the level of expression of mRNA encoding a protein of interest. Methods of evaluating RNA expression of a particular gene are well known to those of skill in the art, and include, inter alia, hybridization and amplification based assays.

Methods of detecting and/or quantifying the level of gene transcripts of interest (mRNA or cDNA made therefrom) using nucleic acid hybridization techniques are known to those of skill in the art. For example, one method for evaluating the presence, absence, or quantity of polynucleotides involves a northern blot. Gene expression levels can also be analyzed by techniques known in the art, e.g., dot blotting, in situ hybridization, RNase protection, probing DNA microchip arrays, and the like.

In another embodiment, amplification-based assays are used to measure the expression level of a gene of interest. In such an assay, the nucleic acid sequences act as a template in an amplification reaction (e.g., Polymerase Chain Reaction, or PCR). In a quantitative amplification, the amount of amplification product will be proportional to the amount of template in the original sample (e.g., can from a reverse transcription reaction of the target RNA). Comparison to appropriate controls provides a measure of the level of expression of the gene of interest in the sample. Methods of quantitative amplification are well known to those of skill in the art. Detailed protocols for quantitative PCR are provided, e.g., in Innis et al. (1990). The nucleic acid sequences provided herein are sufficient to enable one of skill to select primers to amplify any portion of the gene and/or encoded RNA.

In one non-limiting embodiment, a TaqMan™ based assay is used to quantify the cancer-associated polynucleotides. TaqMan™ based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan™ probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

Other suitable amplification methods include, but are not limited to, ligase chain reaction (LCR) (see, Wu and Wallace, 1989; Landegren et al., 1988; and Barringer et al., 1990; transcription amplification (Kwoh et al., 1989), self-sustained sequence replication (Guatelli et al., 1990), dot PCR, and linker adapter PCR, etc.

Polypeptides encoded by the genes described herein can be detected and/or quantified by any methods known to those of skill in the art from samples as described herein. In some embodiments, antibodies can also be used to detect polypeptides encoded by the genes described herein. Antibodies to these polypeptides can be produced using well known techniques (see, e.g., Harlow & Lane, 1988 and Harlow & Lane, 1999; Coligan, 1991; Goding, 1986; and Kohler & Milstein, 1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., 1989; Ward et al., 1989).

Once specific antibodies are available, binding interactions with the proteins of interest can be detected by a variety of immunoassay methods. For a review of immunological and immunoassay procedures, see *Basic and Clinical Immunology* (1991). Moreover, the immunoassays of certain aspects of the present invention can be performed in any of several configurations, which are reviewed extensively in *Enzyme Immunoassay* (1980); and Harlow & Lane, supra).

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide or a labeled antibody that binds the protein of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., 1973; Akerstrom et al., 1985). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., 1986).

VII. Therapy and Therapeutic Monitoring for UC Patients

In certain embodiments, after evaluation of risks for developing colon dysplasia or cancer based on one or more biological markers described above have been made for the UC patients (or subjects determined to have high risk for UC), a course of therapy or therapeutic monitoring may be recommended, prescribed, or provided to the patients or subjects based on the evaluation outcome.

In certain instances, when the UC patients or subjects are determined to have low risk for having colon dysplasia or cancer, conventional surveillance for colon cancer and/or a therapeutically effective amount of a UC therapeutic agent useful for treating one or more symptoms associated with UC may be recommended, prescribed, or provided. For therapeutic applications, the UC therapeutic agent can be administered alone or co-administered in combination with one or more additional UC therapeutic agents and/or one or more drugs that reduce the side-effects associated with the therapeutic agent. Examples of UC therapeutic agents include, but are not limited to, biologic agents, conventional drugs, and combinations thereof.

In further aspects, when the UC patients or subjects are determined to have high risk for having colon dysplasia or cancer, additional intensive surveillance for colon cancer and/or therapeutically effective amount of a colon cancer or dysplasia therapeutic agent useful for treating one or more symptoms associated with colon cancer or dysplasia may be recommended, prescribed, or provided.

As such, certain aspects of the present invention advantageously enables a clinician to practice "personalized medicine" by guiding treatment decisions and informing therapy selection for UC patients or subjects such that the right drug is given to the right patient at the right time.

A. Treatment and Therapeutic Agents

"Treatment" and "treating" refer to administration or application of a therapeutic agent or regimen to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

UC or colorectal therapeutic agents can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that a therapeutic agent is administered at the same time, just prior to, or just after the administration of a second drug (e.g., another therapeutic agent, a drug useful for reducing the side-effects of the first therapeutic agent, etc.).

A therapeutically effective amount of a therapeutic agent may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, forms, or the like, preferably in unit dosage forms suitable for simple administration of precise dosages.

As used herein, the term "unit dosage form" includes physically discrete units suitable as unitary dosages for human subjects and other mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the therapeutic agent.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a therapeutic agent, any of the following: a diluent such as lactose, sucrose, dicalcium phosphate, and the like; a disintegrant such as starch or derivatives thereof a lubricant such as magnesium stearate and the like; and a binder such a starch, gum acacia, polyvinylpyrrolidone, gelatin, cellulose and derivatives thereof. A therapeutic agent can also be formulated into a suppository disposed, for example, in a polyethylene glycol (PEG) carrier.

Liquid dosage forms can be prepared by dissolving or dispersing a therapeutic agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A therapeutic agent can also be formulated into a retention enema.

For topical administration, the therapeutically effective dose can be in the form of emulsions, lotions, gels, foams, creams, jellies, solutions, suspensions, ointments, and transdermal patches. For administration by inhalation, a therapeutic agent can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of UC or colon cancer dysplasia or a clinical subtype thereof, a therapeutic agent can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of UC or colon cancer dysplasia symptoms, and the UC or colon cancer dysplasia therapeutic agent being employed. For example, dosages can be empirically determined considering the type and severity of UC or colon cancer dysplasia symptoms in an individual classified as having a particular clinical subtype of UC or colon cancer dysplasia according to the methods described herein. The dose administered to an individual may be sufficient to affect a beneficial therapeutic response in the individual over time. The size of the dose can also be determined by the existence, nature, and extent of any adverse side-effects that accompany the administration of a particular UC or colon cancer dysplasia therapeutic agent in an individual. Determination of the proper dosage for a particular situation is within the skill of the practitioner. Generally, treatment is initiated with smaller dosages which are less than the optimum dose of the UC or colon cancer dysplasia therapeutic agent. Thereafter, the dosage is increased by small increments until the optimum effect under circumstances is reached. For convenience, the total daily dosage may be divided and administered in portions during the day, if desired.

B. Colon Cancer Therapeutic Regimen

In certain aspects of the invention, colon cancer therapy or intensive monitoring for colon cancer therapy may be prescribed, provided or recommended for UC patients or subjects.

1. Monitoring

For example, the biomarker-based method may be combined with one or more other colon cancer diagnosis or screening tests at increased frequency if the patient is determined to be at high risk for colon dysplasia or cancer based on the methylation profile of the biomarkers described above.

The colon monitoring may include any methods known in the art. In particular, the monitoring include obtaining a sample and testing the sample for diagnosis. For example, the colon monitoring may include colonoscopy or coloscopy, which is the endoscopic examination of the large bowel and the distal part of the small bowel with a CCD camera or a fiber optic camera on a flexible tube passed through the anus. It can provide a visual diagnosis (e.g. ulceration, polyps) and grants the opportunity for biopsy or removal of suspected colorectal cancer lesions. Thus, colonoscopy or coloscopy can be used for treatment.

In further aspects, the monitoring diagnosis may include sigmoidoscopy, which is similar to colonoscopy—the difference being related to which parts of the colon each can examine. A colonoscopy allows an examination of the entire colon (1200-1500 mm in length). A sigmoidoscopy allows an examination of the distal portion (about 600 mm) of the colon, which may be sufficient because benefits to cancer survival of colonoscopy have been limited to the detection of lesions in the distal portion of the colon. A sigmoidoscopy is often used as a screening procedure for a full colonoscopy, often done in conjunction with a fecal occult blood test (FOBT). About 5% of these screened patients are referred to colonoscopy.

In additional aspects, the monitoring diagnosis may include virtual colonoscopy, which uses 2D and 3D imagery reconstructed from computed tomography (CT) scans or from nuclear magnetic resonance (MR) scans, as a totally non-invasive medical test.

The monitoring include the use of one or more screening tests for colon cancer including, but not limited to fecal occult blood testing, flexible sigmoidoscopy and colonoscopy. Of the three, only sigmoidoscopy cannot screen the right side of the colon where 42% of malignancies are found. Virtual colonoscopy via a CT scan appears as good as standard colonoscopy for detecting cancers and large adenomas but is expensive, associated with radiation exposure, and cannot remove any detected abnormal growths like standard colonoscopy can. Fecal occult blood testing (FOBT) of the stool is typically recommended every two years and can be either guaiac based or immunochemical. Annual FOBT screening results in a 16% relative risk reduction in colorectal cancer mortality, but no difference in all-cause mortality. The M2-PK test identifies an enzyme in colorectal cancers and polyps rather than blood in the stool. It does not require any special preparation prior to testing. M2-PK is sensitive for colorectal cancer and polyps and is able to detect bleeding and non-bleeding colorectal cancer and polyps. In the event of a positive result people would be asked to undergo further examination e.g. colonoscopy.

2. Surgery

For people with localized cancer, the preferred treatment is complete surgical removal with adequate margins, with the attempt of achieving a cure. This can either be done by an open laparotomy or sometimes laparoscopically. If there are only a few metastases in the liver or lungs they may also be removed. Sometimes chemotherapy is used before surgery to shrink the cancer before attempting to remove it. The two most common sites of recurrence of colorectal cancer is in the liver and lungs.

3. Chemotherapy Agents

In both cancer of the colon and rectum, chemotherapy may be used in addition to surgery in certain cases. In rectal cancer, chemotherapy may be used in the neoadjuvant setting.

If cancer has entered the lymph nodes, adding the chemotherapy agents fluorouracil or capecitabine increases life expectancy. If the lymph nodes do not contain cancer, the benefits of chemotherapy are controversial. If the cancer is widely metastatic or unresectable, treatment is then palliative. For example, a number of different chemotherapy medications may be used. Chemotherapy agents for this condition may include capecitabine, fluorouracil, irinotecan, leucovorin, oxaliplatin and UFT. Another type of agent that is sometimes used are the epidermal growth factor receptor inhibitors.

4. Radiation Agents

While a combination of radiation and chemotherapy may be useful for rectal cancer, its use in colon cancer is not routine due to the sensitivity of the bowels to radiation. Just as for chemotherapy, radiotherapy can be used in the neo-adjuvant and adjuvant setting for some stages of rectal cancer.

5. Other Treatment Options

In people with incurable colorectal cancer, treatment options including palliative care can be considered for improving quality of life. Surgical options may include non-curative surgical removal of some of the cancer tissue, bypassing part of the intestines, or stent placement. These procedures can be considered to improve symptoms and reduce complications such as bleeding from the tumor, abdominal pain and intestinal obstruction. Non-operative methods of symptomatic treatment include radiation therapy to decrease tumor size as well as pain medications C. UC Therapeutic Regimen UC therapeutic regimen may be used for any UC patients, including any UC therapeutic agents or options, such as surgical options. As used herein, the term "UC therapeutic agent" includes all pharmaceutically acceptable forms of a drug that is useful for treating one or more symptoms associated with UC.

For example, the UC therapeutic agent can be in a racemic or isomeric mixture, a solid complex bound to an ion exchange resin, or the like. In addition, the UC therapeutic agent can be in a solvated form. The term is also intended to include all pharmaceutically acceptable salts, derivatives, and analogs of the UC therapeutic agent being described, as well as combinations thereof. For example, the pharmaceutically acceptable salts of a therapeutic agent include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of a UC or colon cancer dysplasia therapeutic agent is suitable, e.g., a pharmaceutically acceptable salt of a UC or colon cancer dysplasia therapeutic agent, a free base of a UC or colon cancer dysplasia therapeutic agent, or a mixture thereof. Examples of suitable UC or colon cancer dysplasia therapeutic agents include, but are not limited to, biologic agents, conventional drugs, and combinations thereof.

Examples of conventional UC drugs include, without limitation, aminosalicylates (e.g., mesalazine, sulfasalazine, and the like), corticosteroids (e.g., prednisone), thiopurines (e.g., azathioprine, 6-mercaptopurine, and the like), methotrexate, free bases thereof, pharmaceutically acceptable salts thereof, derivatives thereof, analogs thereof, and combinations thereof.

For example, sulfasalazine has been a major agent in the therapy of mild to moderate UC for over 50 years. Since 1977, many 5-ASA compounds have been developed with the aim of maintaining efficacy but reducing the common side effects associated with the sulfapyridine moiety in sulfasalazine.

UC therapeutic biologic agents include, e.g., anti-cytokine and chemokine antibodies such as anti-tumor necrosis factor alpha (TNFα) antibodies. Non-limiting examples of anti-TNFα antibodies include: chimeric monoclonal antibodies such as infliximab (Remicade®) (Centocor, Inc.; Horsham, Pa.), which is a chimeric IgG1 anti-TNFα monoclonal antibody; humanized monoclonal antibodies such as CDP571 and the PEGylated CDP870; fully human monoclonal antibodies such as adalimumab (Humira®) (Abbott Laboratories; Abbott Park, Ill.); p75 fusion proteins such as etanercept (Enbrel®) (Amgen; Thousand Oaks, Calif.; Wyeth Pharmaceuticals Inc.; Collegeville, Pa.), small molecules (e.g., MAP kinase inhibitors); and combinations thereof. See, Ghosh, 2004.

Other UC therapeutic biologic agents include, e.g., anti-cell adhesion antibodies such as natalizumab (Tysabri®) (Elan Pharmaceuticals, Inc.; Dublin, Ireland; Biogen Idec; Cambridge, Mass.), which is a humanized monoclonal antibody against the cellular adhesion molecule α4-integrin, and MLN-02 (Millennium Pharmaceuticals; Cambridge, Mass.), which is a humanized IgG1 anti-α4β7-integrin monoclonal antibody; anti-T cell agents; anti-CD3 antibodies such as visilizumab (Nuvion®) (PDL BioPharma; Incline Village, Nev.), which is a humanized IgG2M3 anti-CD3 onoclonal antibody; anti-CD4 antibodies such as priliximab (cM-T412) (Centocor, Inc.; Horsham, Pa.), which is a chimeric anti-CD4 monoclonal antibody; anti-IL-2 receptor alpha (CD25) antibodies such as daclizumab Zenapax®) (PDL BioPharma; Incline Village, Nev.; Roche; Nutley, N.J.), which is a humanized IgG1 anti-CD25 monoclonal antibody, and basiliximab (Simulect®) (Novartis; Basel, Switzerland), which is a chimeric IgG1 anti-CD25 monoclonal antibody; and combinations thereof.

In addition to the foregoing biological agents, miRs or inhibitors of miRs may be useful. As such, in certain embodiments, treatment of UC may include introducing into or providing to a UC patient an effective amount of i) an miRNA inhibitor molecule or ii) a miRNA molecule. One useful formulation for the delivery of miRs are liposomes. Liposomes and emulsions are well-known examples of delivery vehicles that may be used to deliver nucleic acids. A nucleic acid can be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly (L-lysine).

One skilled in the art will know of additional UC therapeutic agents suitable for use (see, e.g., Sands, 2006; Danese et al., 2006; Domenech, 2006; Nakamura et al., 2006; Gionchetti et al., 2006).

In certain aspects, the gastrointestinal aspect ulcerative colitis can be cured by surgical removal of the large intestine, also known as a colectomy, which can be a therapeutic agent for UC. This procedure is necessary in the event of: exsanguinating hemorrhage, frank perforation or documented or strongly suspected carcinoma. Surgery is also indicated for patients with severe colitis or toxic megacolon. Patients with symptoms that are disabling and do not respond to drugs may wish to consider whether surgery would improve the quality of life.

Another surgical option for ulcerative colitis that is affecting most of the large bowel is called the ileo-anal pouch procedure. This procedure is a two- to three-step procedure in which the large bowel is removed, except for the rectal stump and anus, and a temporary ileostomy is made. The next part of the surgery can be done in one or two steps and is usually done at six to twelve month intervals from each prior surgery. In the next step of the surgery an internal pouch may be made of the patients' own small bowel and this pouch is then hooked back up internally to the rectal stump so that patient can once again have a reasonably functioning bowel system, all internal. The temporary ileostomy can be reversed at this time so that the patient is now internalized for bowel functions, or in another step to the procedure, the pouch and rectal stump anastomosis can be left inside the patient to heal for some time, while the patient still uses the ileostomy for bowel function. Then on a subsequent surgery the ileostomy may be reversed and the patient has internalized bowel function again.

An individual can also be monitored at periodic time intervals to assess the efficacy of a certain therapeutic regimen once diagnostic and/or predictive information has been obtained from the individual's sample. For example, the presence or level of certain markers may change based on the therapeutic effect of a treatment such as a drug. In certain embodiments, the patient can be monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

VIII. Pharmaceutical Compositions

In certain aspects, the compositions or agents for use in the methods are suitably contained in a pharmaceutically acceptable carrier. The carrier is non-toxic, biocompatible and is selected so as not to detrimentally affect the biological activity of the agent. The agents in some aspects of the invention may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the invention also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Clinical Significance of Tissue miR-124 Methylation in Sporadic and Ulcerative Colitis-Associated Colorectal Cancer Growing evidence indicates that the expression of several miRNAs can be epigenetically regulated through methylation of their promoter CpG sequences. MiR-124 is one such tumor suppressive miRNA, which is expressed at lower levels in various human cancers due to methylation of its promoter region. The present study aimed to determine miR-124 methylation status and determine its clinical significance in sporadic and ulcerative colitis-associated colorectal cancer (CRC).

579 colorectal tissues were analyzed, which included 176 sporadic CRC and the corresponding adjacent normal colonic mucosa (NC), 57 colorectal adenomas and 20 normal colonic mucosae from non-cancer patients (NN). In addition, 135 normal mucosae (N-UC), 12 dysplasia (D-UC) and 12 colitic cancers (C-UC) from UC patients were also examined. Quantitative bisulfite pyrosequencing analysis was performed to determine miR-124 promoter methylation levels.

MiR-124 methylation rate was significantly higher in CRCs and adenomas compared to NC or NN ($P<0.0001$, CRC vs. NC; $P<0.0001$, CRC vs. NN). Receiver operating characteristic (ROC) analysis revealed that methylation levels of miR-124 can robustly discriminate patients with CRC (AUC=0.977) and adenomas (AUC=0.985) from healthy controls. Kaplan-Meier survival analysis showed that patients with high miR-124 methylation demonstrated poor overall survival ($p=0.001$), and high miR-124 methylation was an independent prognostic factor of sporadic CRC ($p=0.028$). Similarly, miR-124 methylation was significantly higher in C-UC and D-UC compared to N-UC ($p<0.0001$).

ROC analysis showed that miR-124 methylation can successfully discriminate C-UC (AUC=0.978) and D-UC (AUC=0.884) from N-UC. Interestingly, high levels of miR-124 methylation in rectal specimens were an independent predictor for the development of UC-associated CRC.

Example 2

Figure 6:
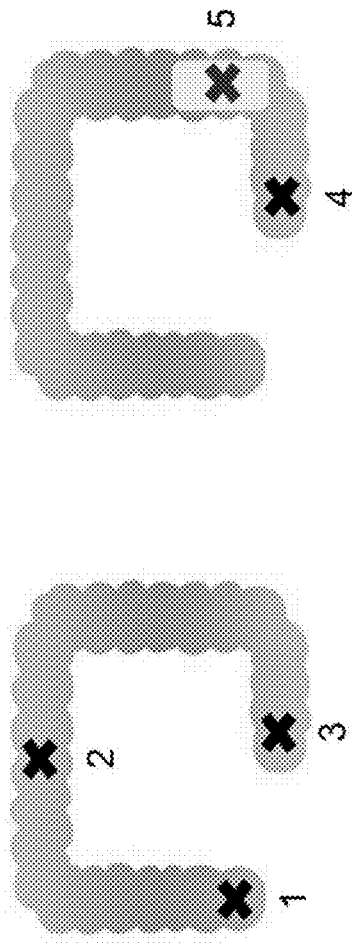
FIG. 6: Flow chart for current methylation analysis in UC. Sample 1, 2 and 3 mean tissues in Cecum, Transverse colon and Rectum from UC patients without neoplasia, respectively. Sample 4 and 5 mean tissues in rectum and neoplasia from UC patients with neoplasia, respectively.

MicroRNA-124, -137 and -34b/c Methylation Predicts Development of UC-associated Neoplasia Here, to clarify whether analysis of miR-124, -137 and -34b/c methylation in non-neoplastic epithelium can help predict UC-associated CRC, the inventors systematically investigated incidence of methylation of 3 miRNAs in UC (FIG. 6). First, it was determined whether these 3 miRNAs have a pattern of age- and location-related methylation in multiple UC mucosae without neoplasia. Next, it was investigated whether methylation patterns in these miRNAs are cancer-dependent, using non-neoplastic mucosa and neoplasia from UC. Finally, a "field defect" in methylation of these miRNAs was assessed using non-neoplastic rectal mucosa from UC patients with and without neoplasia, and evaluated whether "field defect" was predictive for inflammation-induced neoplasia in UC patients.

Characteristics of UC patients. Clinicopathologic features of the 70 patients with UC are shown in Table 1. Patients with UC and with or without neoplasia showed no significantly difference of gender, age at onset, age at surgery, extent of disease and inflammatory degree. However, median disease durations were significantly longer in patients with dysplasia (8 years: 1-28) and cancer (12 years: 1-24) than in patients without neoplasia (6 years: 1-28). (P=0.029; Table 1.)

TABLE 1

Patient characteristics

| Characteristic | | Patients with non-neoplasia (n = 45) | Patients with dysplasia (n = 12) | Patients with cancer (n = 13) | P |
|---|---|---|---|---|---|
| Gender | Male | 25 | 6 | 10 | 0.31 |
| | Female | 20 | 6 | 3 | |

TABLE 1-continued

Patient characteristics

| Characteristic | | Patients with non-neoplasia (n = 45) | Patients with dysplasia (n = 12) | Patients with cancer (n = 13) | P |
|---|---|---|---|---|---|
| Age at diagnosis of UC in years (range) | | 29 (9-61) | 30.5 (20-38) | 29 (17-55) | 0.68 |
| Age at surgery for UC in years (range) | | 36 (11-62) | 36.5 (27-56) | 39 (28-74) | 0.43 |
| Extent of disease | Total colitis | 33 | 8 | 8 | 0.69 |
| | Left-side colitis | 12 | 4 | 5 | |
| Duration of disease in years (range) | | 6 (1-28) | 8 (1-28) | 12 (1-24) | 0.029 |
| Degree of inflammation | Mild | 20 | 5 | 9 | 0.5 |
| | Moderate | 23 | 6 | 4 | |
| | Severe | 2 | 1 | 0 | |

UC: Ulcerative colitis

Methylation levels of miR-124, -137 and -34b/c in non-neoplastic UC tissues are significantly associated with age, disease duration and colorectal location. Associations between miR-124, -137 and 34b/c methylation levels in neoplastic mucosa from UC were evaluated and clinicopathological findings subdivided by location in the colorectum (n=135). MiR-124 and -137 methylation levels showed stepwise increases from cecum to rectum; both rectal methylation levels were significantly higher than in the cecum (miR-124: 7.16±2.43% vs. 9.18±4.24%, P=0.0169; miR-137: 4.87±1.62% vs. 7.13±2.59%, P<0.0001); methylation of miR-34b/c also tended to increase (miR-34b/c: 15.8±4.61% vs. 17.24±6.41%, P=0.46) (FIG. 1A-C). Furthermore, rectal miR-124 and -137 methylation levels were significantly associated with age at diagnosis (miR-124: P=0.04; miR-137: P=0.02), age at surgery (miR-124: P=0.003; miR-137: P=0.003) and long disease duration (miR-124: P=0.014; miR-137: P=0.04) (Tables 6 and 7). In contrast, there was no association between miR-34b/c methylation and clinicopathological findings (Table 8). Collectively, miR-124 and -137 could be age-related methylation in non-neoplastic rectum; rectal methylation in both miRNAs showed higher levels compared to proximal colon.

TABLE 6

Association between miR-124 methylation levels in UC mucosa without neoplasia and clinical findings, subdivided by location

| | | miR-124 methylation levels (mean ± SD) | | | | | |
|---|---|---|---|---|---|---|---|
| Category | | Cecum | p | Transverse | p | Rectum | p |
| Gender | Male | 7.0 ± 2.5 | 0.88 | 7.8 ± 3.3 | 0.39 | 9.1 ± 4.0 | 0.8 |
| | Female | 7.4 ± 2.4 | | 8.0 ± 2.2 | | 9.3 ± 4.6 | |
| Age at diagnosis | ≤29 yr* | 6.7 ± 2.5 | 0.2 | 7.5 ± 3.3 | 0.08 | 8.6 ± 5.2 | 0.04 |
| | >29 yr* | 7.6 ± 2.4 | | 8.3 ± 2.4 | | 9.7 ± 3.0 | |
| Age at operation | ≤38 yr* | 7.0 ± 2.3 | 0.66 | 7.5 ± 3.3 | 0.051 | 7.6 ± 3.5 | 0.003 |
| | >38 yr* | 7.4 ± 2.6 | | 8.3 ± 2.4 | | 11.0 ± 4.4 | |
| Disease duration | ≤6 yr* | 6.7 ± 1.9 | 0.24 | 7.3 ± 3.0 | 0.012 | 7.5 ± 2.6 | 0.014 |
| | >6 yr* | 7.7 ± 2.8 | | 8.6 ± 2.6 | | 10.9 ± 5.0 | |
| Inflammation degree | Mild | 7.5 ± 3.0 | 0.69 | 8.0 ± 3.4 | 0.28 | 10.1 ± 5.4 | 0.84 |
| | Moderate/severe | 6.7 ± 2.0 | | 7.8 ± 2.4 | | 8.7 ± 2.9 | |
| Colitis type | Left side | 7.2 ± 2.6 | 0.87 | 7.6 ± 2.7 | 0.74 | 9.1 ± 3.2 | 0.71 |
| | Total | 7.2 ± 2.4 | | 8.0 ± 2.9 | | 9.2 ± 4.6 | |

*The median age at onset, median age at surgery and median disease duration are 29, 38, and 6 years, respectively.

TABLE 7

Association between miR-137 methylation levels in UC mucosa without neoplasia and clinical findings, subdivided by location.

| | | miR-137 methylation levels (mean ± SD) | | | | | |
| --- | --- | --- | --- | --- | --- | --- | --- |
| Category | | Cecum | p | Transverse | p | Rectum | p |
| Gender | Male | 4.8 ± 1.7 | 0.45 | 5.5 ± 2.2 | 0.42 | 6.7 ± 2.4 | 0.13 |
| | Female | 4.9 ± 1.6 | | 5.5 ± 1.3 | | 7.7 ± 2.8 | |
| Age at diagnosis | ≤29 yr* | 4.5 ± 1.5 | 0.07 | 4.8 ± 1.4 | 0.01 | 6.5 ± 2.9 | 0.02 |
| | >29 yr* | 5.3 ± 1.6 | | 6.1 ± 2.0 | | 7.7 ± 2.2 | |
| Age at operation | ≤38 yr* | 4.6 ± 1.6 | 0.45 | 5.1 ± 1.5 | 0.2 | 6.0 ± 1.4 | 0.003 |
| | >38 yr* | 5.1 ± 1.6 | | 5.9 ± 2.1 | | 8.4 ± 3.1 | |
| Disease duration | ≤6 yr* | 4.5 ± 1.9 | 0.09 | 5.1 ± 1.4 | 0.19 | 6.4 ± 1.8 | 0.04 |
| | >6 yr* | 5.2 ± 1.3 | | 5.9 ± 2.2 | | 7.9 ± 3.1 | |
| Inflammation degree | Mild | 4.8 ± 1.7 | 0.91 | 5.3 ± 1.4 | 0.88 | 7.4 ± 3.3 | 0.56 |
| | Moderate/severe | 4.9 ± 1.6 | | 5.7 ± 2.2 | | 7.0 ± 1.9 | |
| Colitis type | Left side | 4.6 ± 2.3 | 0.84 | 5.2 ± 1.7 | 0.21 | 7.3 ± 2.2 | 0.59 |
| | Total | 5.0 ± 1.3 | | 5.6 ± 2.0 | | 7.1 ± 2.7 | |

*The median age at onset, median age at surgery and median disease duration are 29, 38, and 6 years, respectively.

TABLE 8

Association between miR-34b/c methylation in UC mucosa without neoplasia and clinical findings subdivided by location.

| | | miR-34b/c methylation levels (mean ± SD) | | | | | |
| --- | --- | --- | --- | --- | --- | --- | --- |
| Category | | Cecum | p | Transverse | p | Rectum | p |
| Gender | Male | 15.4 ± 4.8 | 0.62 | 17.5 ± 6.0 | 0.07 | 17.4 ± 7.0 | 0.81 |
| | Female | 16.3 ± 4.5 | | 14.3 ± 3.0 | | 17.1 ± 5.7 | |
| Age at diagnosis | ≤29 yr* | 16.5 ± 5.1 | 0.34 | 15.6 ± 5.7 | 0.43 | 17.7 ± 8.0 | 0.82 |
| | >29 yr* | 15.0 ± 4.0 | | 16.5 ± 4.7 | | 16.8 ± 4.5 | |
| Age at operation | ≤38 yr* | 15.8 ± 5.4 | 0.84 | 15.3 ± 5.3 | 0.2 | 16.6 ± 6.7 | 0.45 |
| | >38 yr* | 15.8 ± 3.9 | | 17.0 ± 4.9 | | 18.0 ± 6.3 | |
| Disease duration | ≤6 yr* | 16.4 ± 5.1 | 0.44 | 16.0 ± 5.1 | 0.99 | 16.2 ± 6.0 | 0.1 |
| | >6 yr* | 15.1 ± 4.1 | | 16.1 ± 5.3 | | 18.3 ± 6.8 | |
| Inflammation degree | Mild | 16.9 ± 4.7 | 0.27 | 16.8 ± 6.2 | 0.95 | 17.8 ± 8.1 | 0.5 |
| | Moderate/severe | 14.2 ± 3.9 | | 15.4 ± 4.3 | | 16.8 ± 5.0 | |
| Colitis type | Left side | 17.1 ± 5.4 | 0.4 | 16.0 ± 5.7 | 0.72 | 15.9 ± 4.7 | 0.21 |
| | Total | 15.3 ± 4.3 | | 16.1 ± 5.0 | | 17.7 ± 6.9 | |

*The median age at onset, median age at surgery and median disease duration are 29, 38, and 6 years, respectively.

Figures 2A, 2B, 2C:
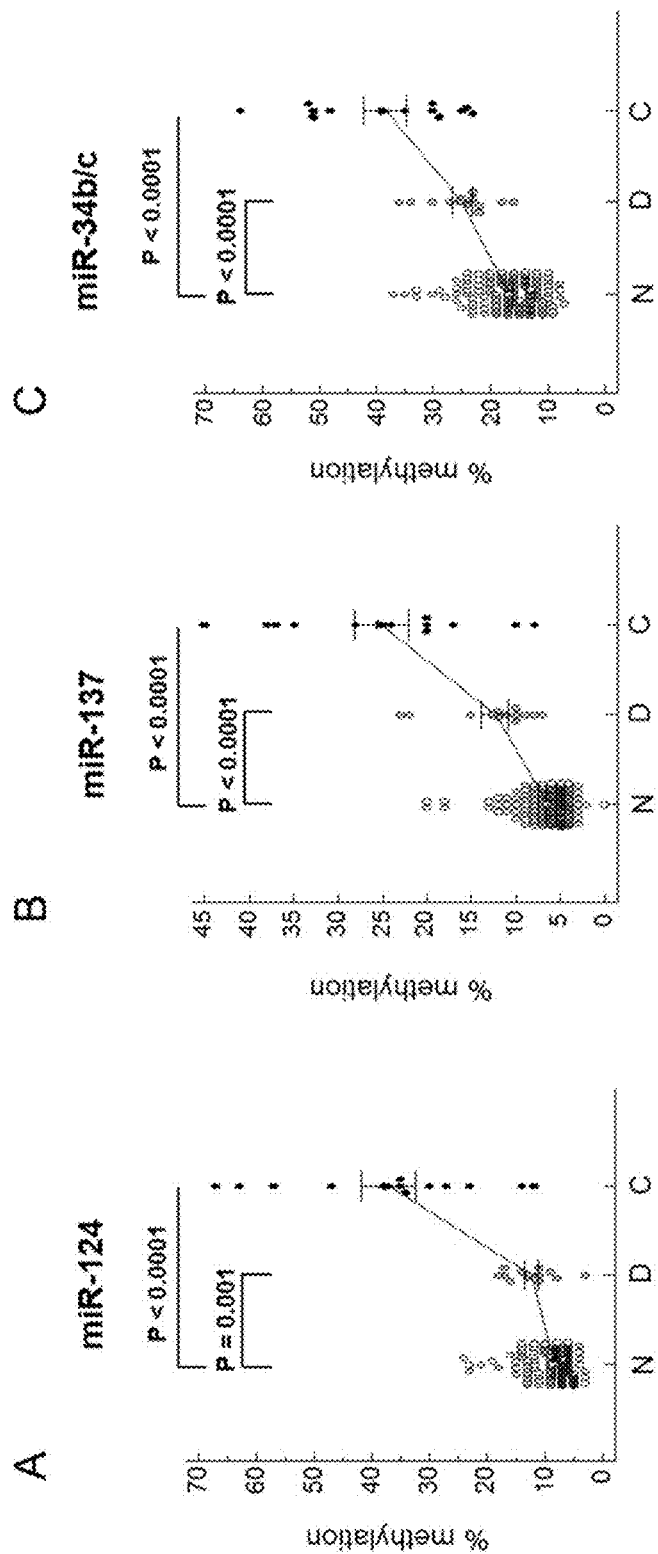
FIG. 2: MiR-124, -137, -34b/c methylation levels in UC mucosa by disease status (n=185). (A) Dot plots of miR-124 methylation levels in non-neoplastic UC mucosa (N; n=160), Dysplasia (D; n=12) and Cancer (C; n=13). (B) Dot plots of miR-137 methylation levels in non-neoplastic UC mucosa (N; n=135), Dysplasia (D; n=12) and Cancer (C; n=13). (C) Dot plots of miR-34b/c methylation levels in non-neoplastic UC mucosa (N; n=135), Dysplasia (D; n=12) and Cancer (C; n=13). Statistically significant differences were determined using Mann-Whitney tests.
Figures 3A, 3B, 3C, 3D, 3E, 3F:
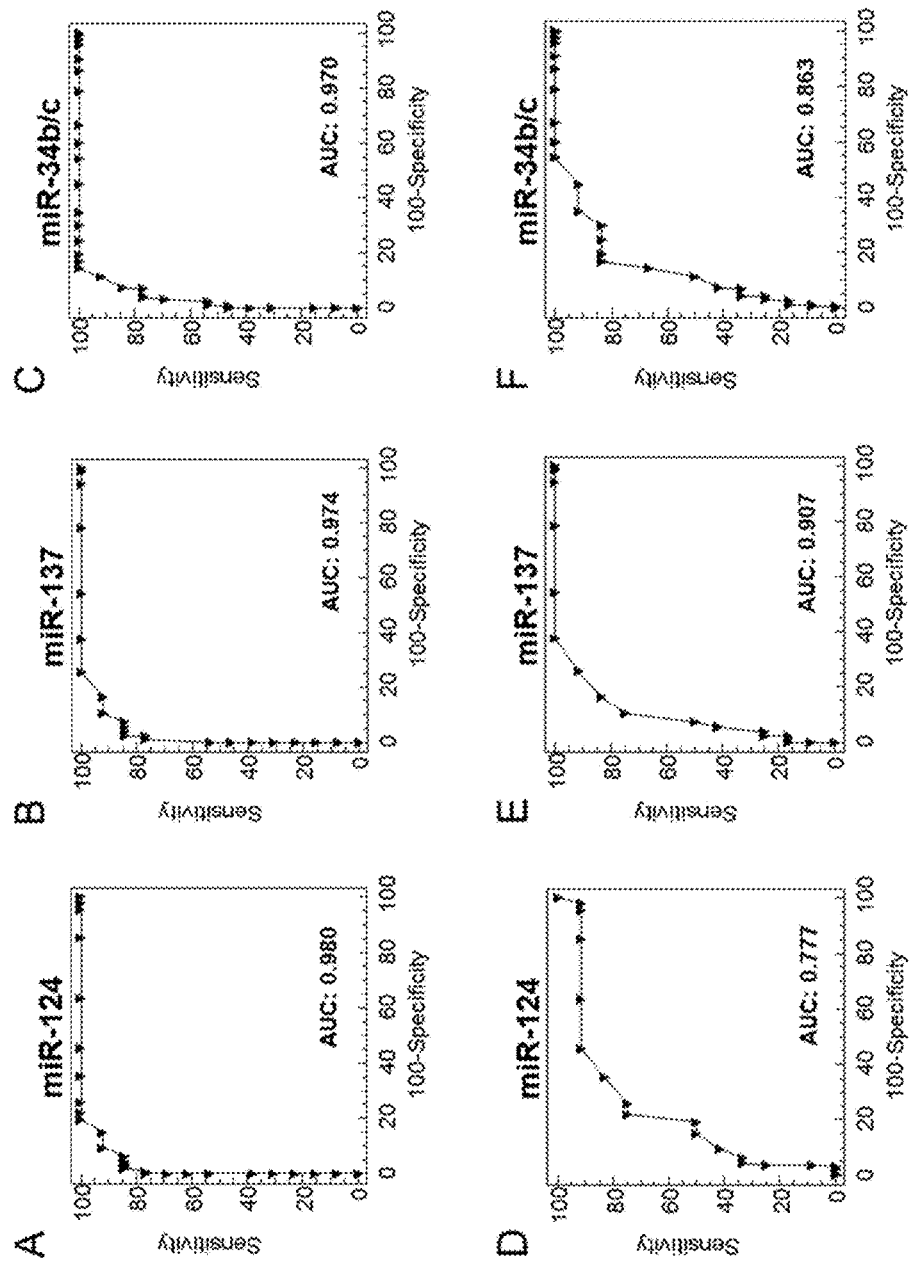
FIG. 3: ROC curve analysis of miR-124, -137, and -34b/c methylation, distinguishing UC-associated neoplasms from non-neoplastic UC mucosa. (A) MiR-124 methylation levels yielded an AUC value of 0.980 (95% CI: 0.946-0.995), with 92.3% sensitivity and 90.6% specificity in distinguishing cancer from non-neoplastic UC mucosa. (B) For miR-137, AUC value of 0.974 (95% CI: 0.937-0.992), with 84.6% sensitivity and 97.5% specificity. (C) For miR-34b/c, AUC value of 0.974 (95% CI: 0.937-0.992), with 84.6% sensitivity and 97.5% specificity. (D) MiR-124 methylation levels yielded an AUC value of 0.777 (95% CI: 0.708-0.837), with 75.0% sensitivity and 78.1% specificity in distinguishing dysplasia from non-neoplastic UC mucosa. (E) For miR-137, AUC value of 0.907 (95% CI: 0.853-0.910), with 83.3% sensitivity and 83.7% specificity. (F) For miR-34b/c, AUC value of 0.863 (95% CI: 0.802-0.910), with 83.3% sensitivity and 83.1% specificity.

Methylation levels of miR-124, -137, and -34b/c in neoplastic tissues are significantly higher than those in non-neoplastic UC tissues. Next, to evaluate the diagnostic potential of miR-124, -137 and -34b/c methylation, a total of 185 tissue samples, including those with non-neoplasia (n=160), dysplasia (n=12) and cancer (n=13), from patients with UC were examined. Compared to non-neoplasia, methylation levels of miR-124, -137 and -34b/c were associated with increased cancer, (miR-124: P<0.0001; miR-137: P<0.0001; miR-34b/c: P<0.0001; FIG. 2A-C). Methylation levels of all 3 miRNAs in dysplasia were also significantly increased compared to non-neoplasia (miR-124: P=0.001; miR-137: P<0.0001; miR-34b/c: P<0.0001; FIG. 2A-C). Our ROC analyses revealed that miR-124, -137 and miR-34b/c methylation levels were robust in discriminating cancer from non-neoplasia, with AUC values of 0.980 (95% CI: 0.946-0.995), 0.974 (95% CI: 0.937-0.992) and 0.970 (95% CI: 0.932-0.990), respectively (FIG. 3A-C). Even more important from a diagnostic perspective, all 3 miRNAs methylation levels could reliably differentiate dysplasia from non-neoplasia, as evidenced by AUC values of 0.777 (95% CI: 0.708-0.837), 0.907 (95% CI: 0.853-0.910) and 0.863 (95% CI: 0.802-0.910), respectively (FIG. 3D-F). Collectively, these results suggest that methylation of these miRNAs occur early in the dysplasia-carcinoma sequence in UC and could be the basis of a method of diagnosing UC-associated neoplasia.

MiR-124, -137, and -34b/c methylation levels in non-neoplastic rectal tissues are biomarkers for patients with UC-associated neoplasia. To assess the potential usefulness of miR-124, -137 and -34b/c methylation levels as biomarkers for early diagnosis of UC-associated neoplasia, the methylation levels of miR-124, -137 and -34b/c were compared in non-neoplastic rectal samples between patients with neoplasia and without. The results showed that all 3 rectal miRNA methylation levels were significantly higher in patients with cancer than in those without (miR-124: 13.4±5.9 vs. 9.2±4.5, P=0.008; miR-137: 11.5±5.1 vs. 7.1±4.5, P=0.001; miR-34b/c: 20.8±5.8 vs. 17.2±6.4, P=0.02; Table 2). Additionally, only miR-137 methylation levels in non-neoplastic tissues from patients with neoplasia (dysplasia and cancer) were significantly higher than from patients without (miR-137: 7.1±2.6 vs. 9.9±4.1, P=0.0003; Table 2). These results can explain the miR-124, -137 and -34b/c methylation "field defect" in UC mucosa.

TABLE 2

Methylation levels of miR-124, -137, -34b/c in non-neoplastic rectal tissue of patients who have ulcerative colitis, with and without neoplasia.

| Category | Patients without cancer (n = 45) | Patients with cancer (n = 13) | P | Patients without neoplasia (n = 45) | Patients with neoplasia (n = 25) | P |
|---|---|---|---|---|---|---|
| miR-124 methylation (mean ± SD) | 9.2 ± 4.5 | 13.4 ± 5.9 | 0.008 | 9.2 ± 4.5 | 10.5 ± 5.4 | 0.33 |
| miR-137 methylation (mean ± SD) | 7.1 ± 2.6 | 11.5 ± 5.1 | 0.001 | 7.1 ± 2.6 | 9.9 ± 4.1 | 0.0003 |
| miR-34b/c methylation (mean ± SD) | 17.2 ± 6.4 | 20.8 ± 5.8 | 0.02 | 17.2 ± 6.4 | 18.3 ± 5.4 | 0.23 |

SD: Standard deviation

Figures 4A, 4B, 4C, 4D, 4E, 4F:
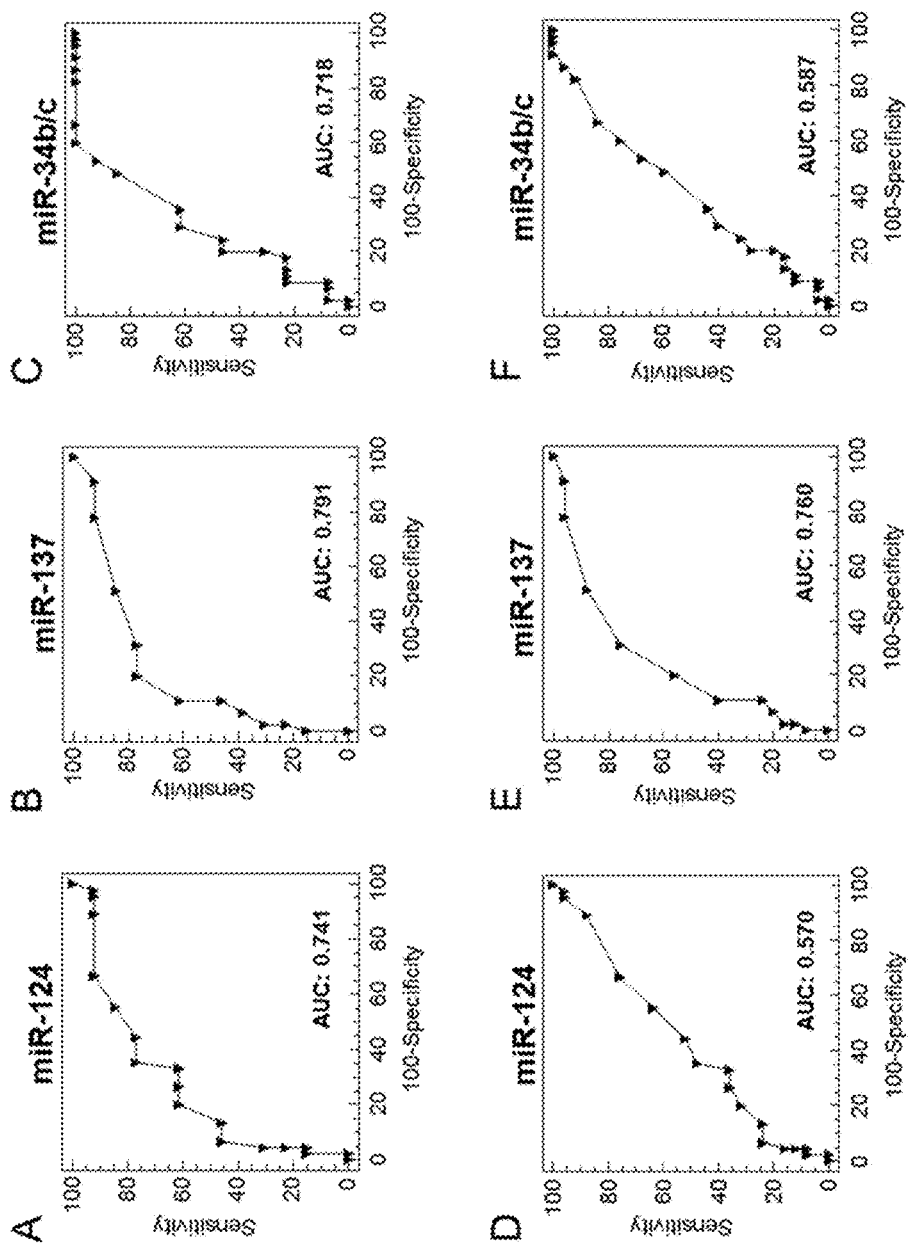
FIG. 4: ROC curve analysis of miR-124, -137, and -34b/c methylation in non-neoplastic rectal mucosa to distinguish patients with UC-associated neoplasms from those without. (A) MiR-124 methylation levels yielded an AUC value of 0.741 (95% CI: 0.609-0.847), with 61.5% sensitivity and 80.0% specificity in distinguishing patients with cancer from patients without. (B) For miR-137, AUC value of 0.791 (95% CI: 0.665-0.887), with 76.9% sensitivity and 80.0% specificity. (C) For miR-34b/c, AUC value of 0.718 (95% CI: 0.584-0.827), with 84.6% sensitivity and 97.5% specificity. (D) MiR-124 methylation levels yielded an AUC value of 0.570 (95% CI: 0.446-0.668), with 75.0% sensitivity and 78.1% specificity in distinguishing patients with UC-associated neoplasia including cancer and dysplasia from patients without. (E) For miR-137, AUC value of 0.760 (95% CI: 0.643-0.854), with 76.0% sensitivity and 68.9% specificity. (F) For miR-34b/c, AUC value of 0.587 (95% CI: 0.463-0.704), with 84.0% sensitivity and 33.3% specificity.

Next, ROC curves were generated to assess the possibility of using miR-124, -137 and -34b/c methylation in non-neoplastic rectum as biomarkers for patients with UC-associated neoplasia. The ROC analyses revealed that miR-124, -137 and -34b/c methylation levels robustly discriminated UC patients with cancer from those without cancer, with AUC values of 0.741 (95% CI: 0.609-0.847), 0.791 (95% CI: 0.665-0.887) and 0.718 (95% CI: 0.584-0.827), respectively (FIG. 4A-C). More importantly from a screening perspective, only miR-137 methylation levels could differentiate UC patients with neoplasia (even dysplasia) from those without neoplasia, as evidenced by AUC value of 0.760 (95% CI: 0.643-0.854), with sensitivity and specificity of 76.0% and 68.9%, respectively (FIG. 4E-F). These results were further strengthened by univariate logistic regression analysis showing that miR-137 methylation levels >7 (OR: 7.01, 95% CI: 1.84-26.80, P=0.004), miR-124 methylation levels >14 (OR: 4.4, 95% CI: 1.00-19.58, P=0.05) and disease duration >8 years (OR: 3.96 95% CI: 1.33-11.77, P=0.01) can be used as biomarkers for patients with UC-associated neoplasia (Table 3). Moreover, multivariate logistic analysis show high miR-137 methylation levels can be an independent diagnostic marker for UC patients with neoplasia (OR: 5.55, 95% CI: 1.40-22.05, P=0.0148; Table 3).

TABLE 3

Univariate and multivariate analyses of factors predictive of neoplasia in patients with ulcerative colitis.

| Variables | Univariate analysis | | | Multivariate analysis | | |
|---|---|---|---|---|---|---|
| | OR | 95% CI | P | OR | 95% CI | P |
| Age at onset (>29 yr vs. ≤29)* | 1.04 | 0.39-2.76 | 0.94 | | | |
| Age at surgery (>38 yr vs. ≤38 yr)* | 1.45 | 0.54-3.89 | 0.46 | | | |
| Disease duration (>8 yr vs. ≤8 yr)* | 3.96 | 1.33-11.77 | 0.01 | 2.7 | 0.81-9.04 | 0.11 |
| Extent of disease (total colitis vs. left-side colitis) | 0.65 | 0.23-1.85 | 0.42 | | | |
| Inflammation score (mild vs. middle/severe) | 0.57 | 0.21-1.54 | 0.27 | | | |
| miR-124 methylation levels in rectum (>14 vs. ≤14)† | 4.4 | 1.00-19.58 | 0.05 | 2.07 | 0.40-10.64 | 0.38 |
| miR-137 methylation levels in rectum (>7 vs. ≤7)† | 7.0145 | 1.84-26.80 | 0.004 | 5.55 | 1.40-22.05 | 0.0148 |
| miR-34b/c methylation levels in rectum (>13 vs. ≤13)† | 2.625 | 0.76-9.03 | 0.1259 | | | |

OR: odds ratio;
CI: confidence interval;
rectum: non-neoplastic mucosa in rectum
*The median age at onset, median age at surgery and median disease duration are 29, 38, and 8 years, respectively.
†For miR-124, miR-137, and miR-34b/c, the cutoff values are 14, 7 and 13, respectively.

Figures 5A, 5B, 5C, 5D, 5E, 5F:
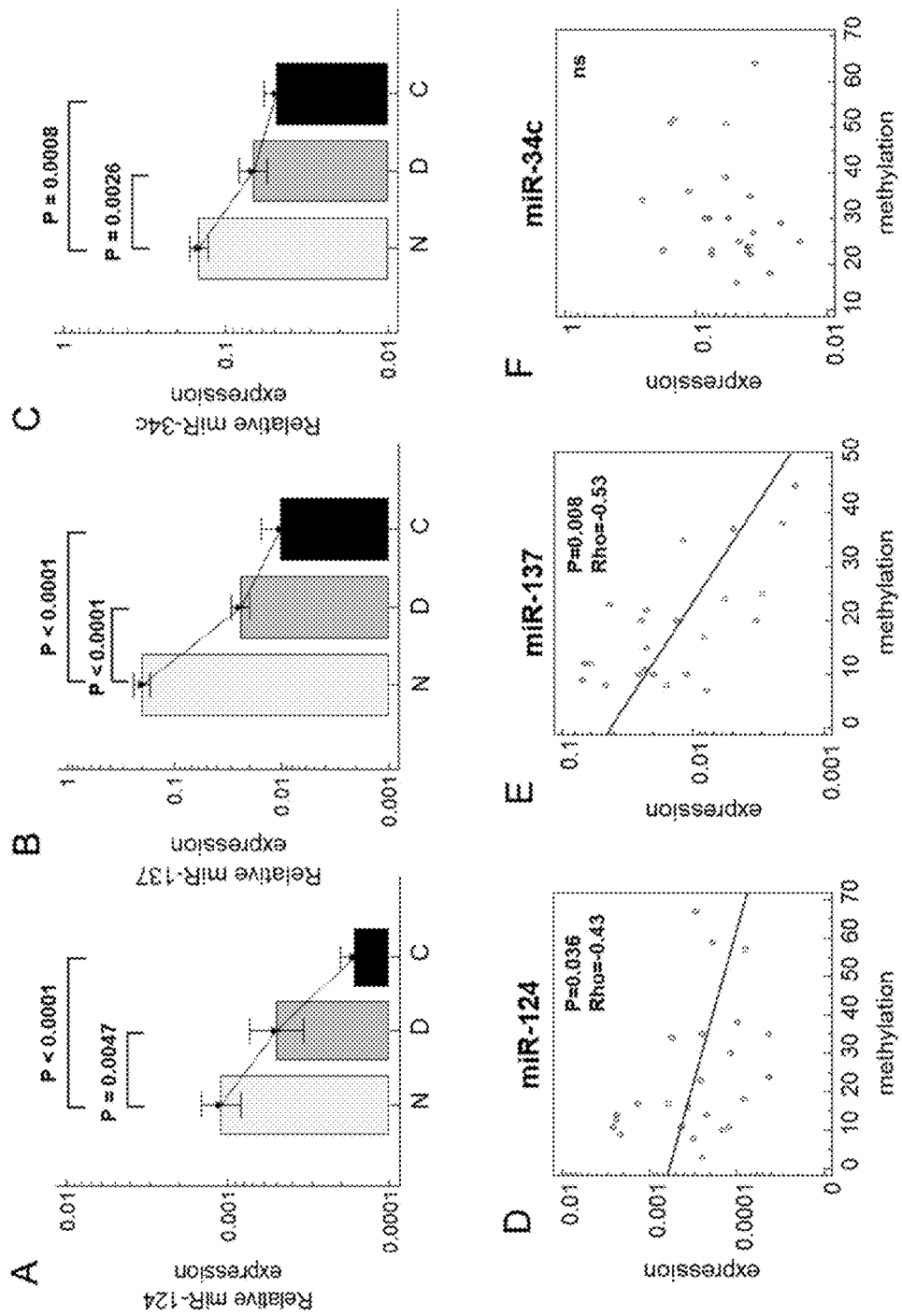
FIG. 5: Expression of miR-124, -137, and -34c in tissues from UC patients. (A) MiR-124 expression levels in non-neoplastic UC mucosa (N; n=20), Dysplasia (D; n=12) and Cancer (C; n=13). (B) miR-137 expression levels in non-neoplastic UC mucosa (N; n=20) Dysplasia (D; n=12) and Cancer (C; n=13). (C) miR-34c expression levels in non-neoplastic UC mucosa (N; n=20), Dysplasia (D; n=12) and Cancer (C; n=13). Y-axis represents relative expression of miRNAs normalized to miR-16 expression. Statistically significant differences were determined using Mann-Whitney tests. Scatter plots of miR-124 (D), -137 (E) and -34c (F) showing correlations between expression levels (Y-axis: Log 10 scale) and methylation levels (X-axis) in samples obtained from 25 UC patients with neoplasia. Negative correlations were found for miR-124 and miR-137 by Spearman correlation (miR-124; $\rho=-0.43$, $P=0.036$, miR-137; $\rho=-0.53$, $P=0.008$).

Inverse correlation between miR-124, -137, and -34b/c methylation and expression levels. To determine whether methylation of miR-124, -137 and -34b/c at a CpG island in the promoter region silences expression in UC tissue, expression levels of miR-124, -137 and -34c were quantified in dysplastic, and cancerous and non-neoplastic UC mucosa. As expected, compared to non-neoplastic mucosa, expression levels of all 3 miRNAs demonstrated stepwise decreases in dysplasia (miR-124: P=0.0047; miR-137: P<0.0001; miR-34c: P=0.0005) and cancer (miR-124: P<0.0001; miR-137: P<0.0001; miR-34c: P<0.0001) (FIG. 5A-C). Methylation and expression of miR-124 and miR-137 were significantly inversely correlated with UC-associated neoplasia (miR-124; ρ=−0.43, P=0.036, miR-137; ρ=−0.53, P=0.008: FIG. 5D, E). In contrast, a similar significant inverse relationship between miR-34b/c methylation and expression and UC-associated neoplasia was not recognized (FIG. 5F).

Example 3

Materials and Methods

Patient and samples. 185 colorectal epithelia samples were studied, including with 160 non-neoplastic and 25 neoplastic tissues, from 70 patients with UC. Diagnosis of UC was based on medical history, endoscopic findings, histological examination, laboratory tests and clinical disease presentation. Extent of disease was characterized as left-side colitis or total colitis; inflammatory severity was classified as "mild," "moderate" or "severe," based on clinical, endoscopic and histological findings. Patients with right-sided colitis, segmental colitis and proctitis, acute fulminating UC, or who were presenting with their first attacks were excluded from evaluation. Twenty-five patients had neoplasia (Table 4); 45 patients had no neoplasia. In non-neoplastic patients, multiple samples were taken from 3 regions (cecum, transverse colon and rectum); 2 regions (neoplastic tissue and rectum without neoplasia) were sampled from patients with neoplasia (FIG. 6). All samples were retrieved from colectomy specimens, which were resected at Mie University Hospital between 2005 and 2010. Specimen collection and studies were approved by the Institutional Review Broad (IRB) at the Mie University Hospital in Japan and Baylor Medical Center at Dallas in USA. All participants provided written consent and willingness to donate their tissue samples for research.

DNA extraction from formalin-fixed paraffin-embedded (FFPE) samples. FFPE samples were cut serially at 10 μM. Based on histological findings, the tissue of each region was microdissected; DNA was extracted using the QIAmp DNA FFPE tissue kit (Qiagen, Valencia, Calif., USA) according to the manufacturer's protocol.

Figure 7A:
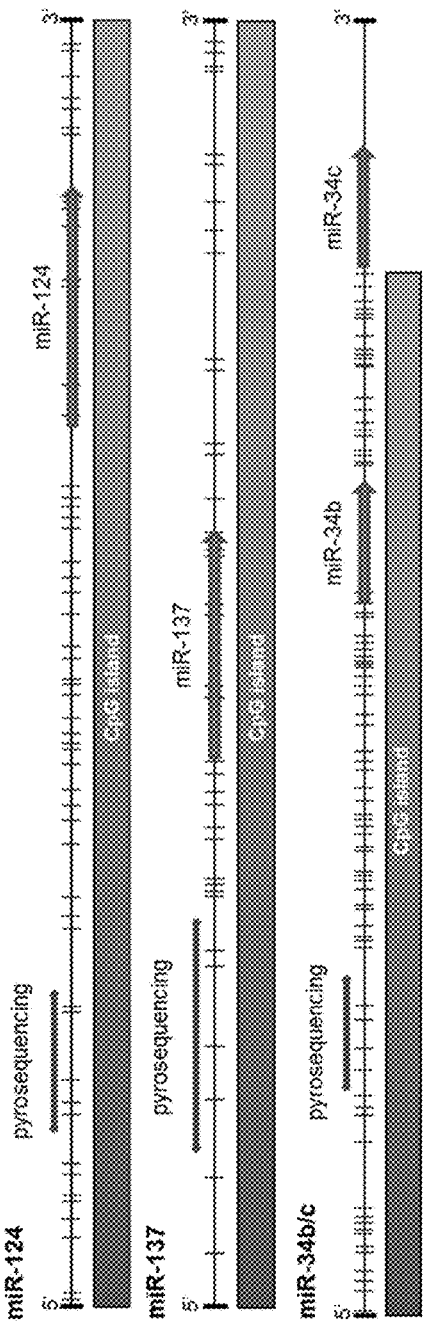
FIG. 7: Methylation analysis of miR-124, -137, -34b/c CpG islands. (A) Maps of miR-124, -137 and -34b/c CpG islands and positions of miR-124, -137 and -34b and -34c sequences and PCR products used for bisulfite pyrosequencing analysis. Orange box: CpG island; vertical tick marks: CpG sites. (B) Results of bisulfite pyrosequencing miR-124, -137 and -34b/c. Methylation percentages of some CpG sites (marked in gray vertical boxes) are shown in the pyrogram.
Figure 7B:
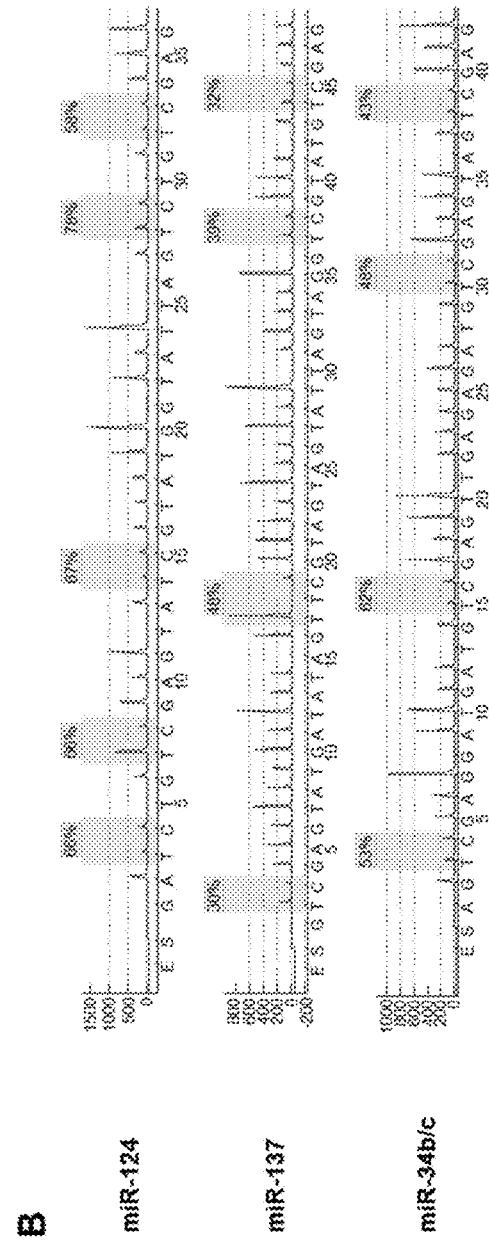
Figure 8:
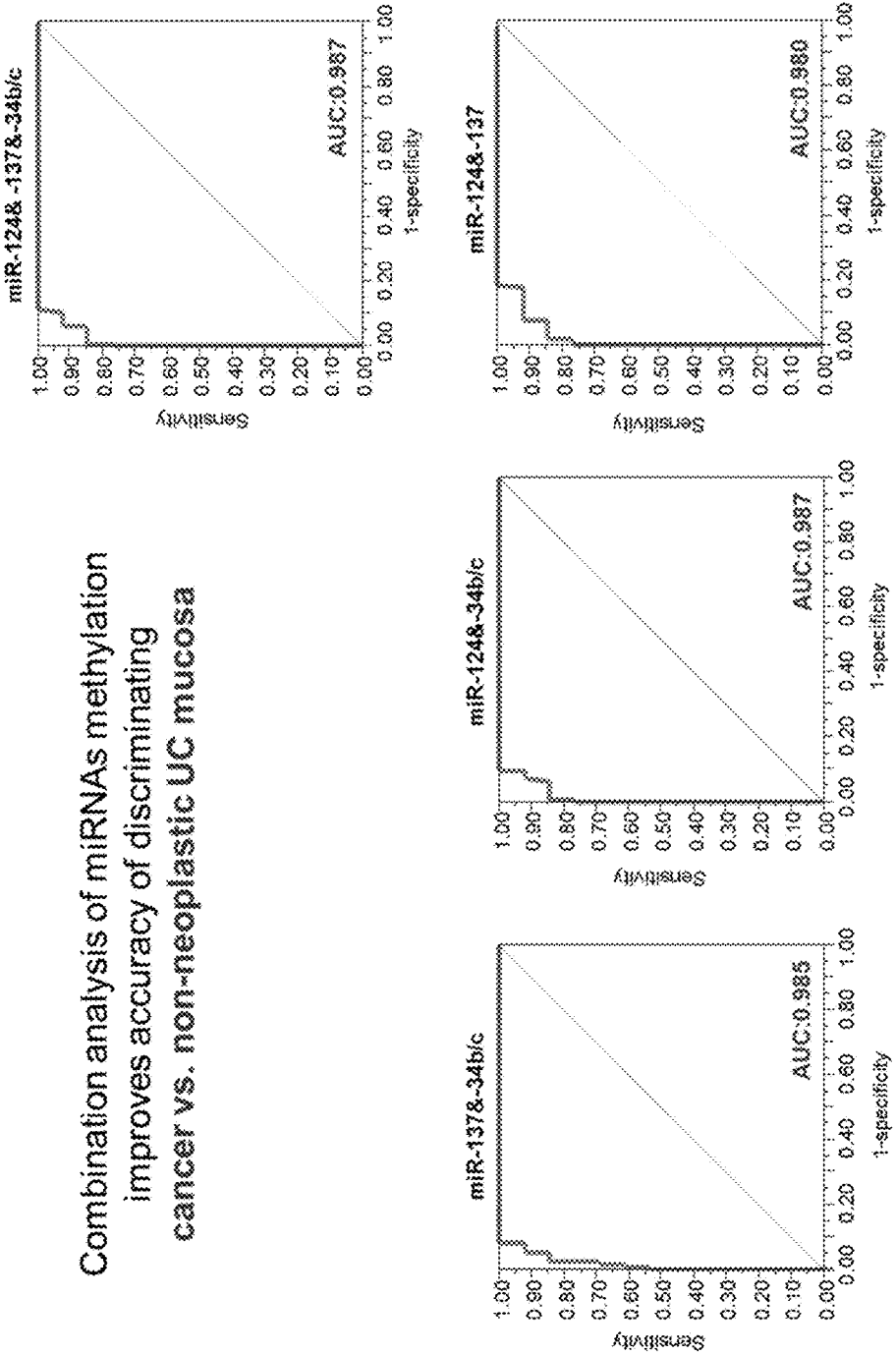
FIG. 8: Discrimination accuracy of cancer vs. non-neoplastic UC mucosa by combination analysis of miRNA methylation.
Figure 9:
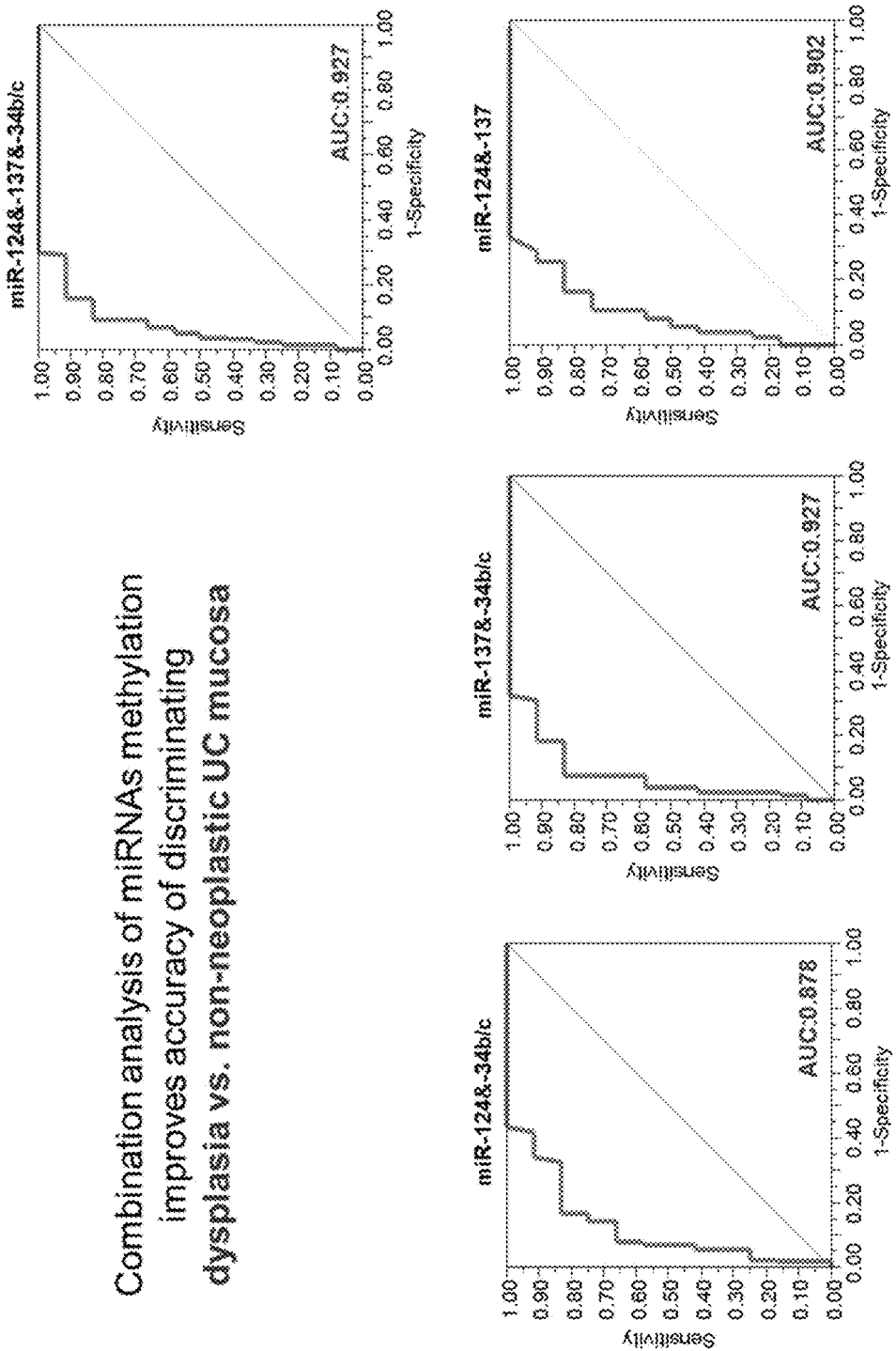
FIG. 9: Discrimination accuracy of dysplasia vs. non-neoplastic UC mucosa by combination analysis of miRNA methylation.
Figure 10:
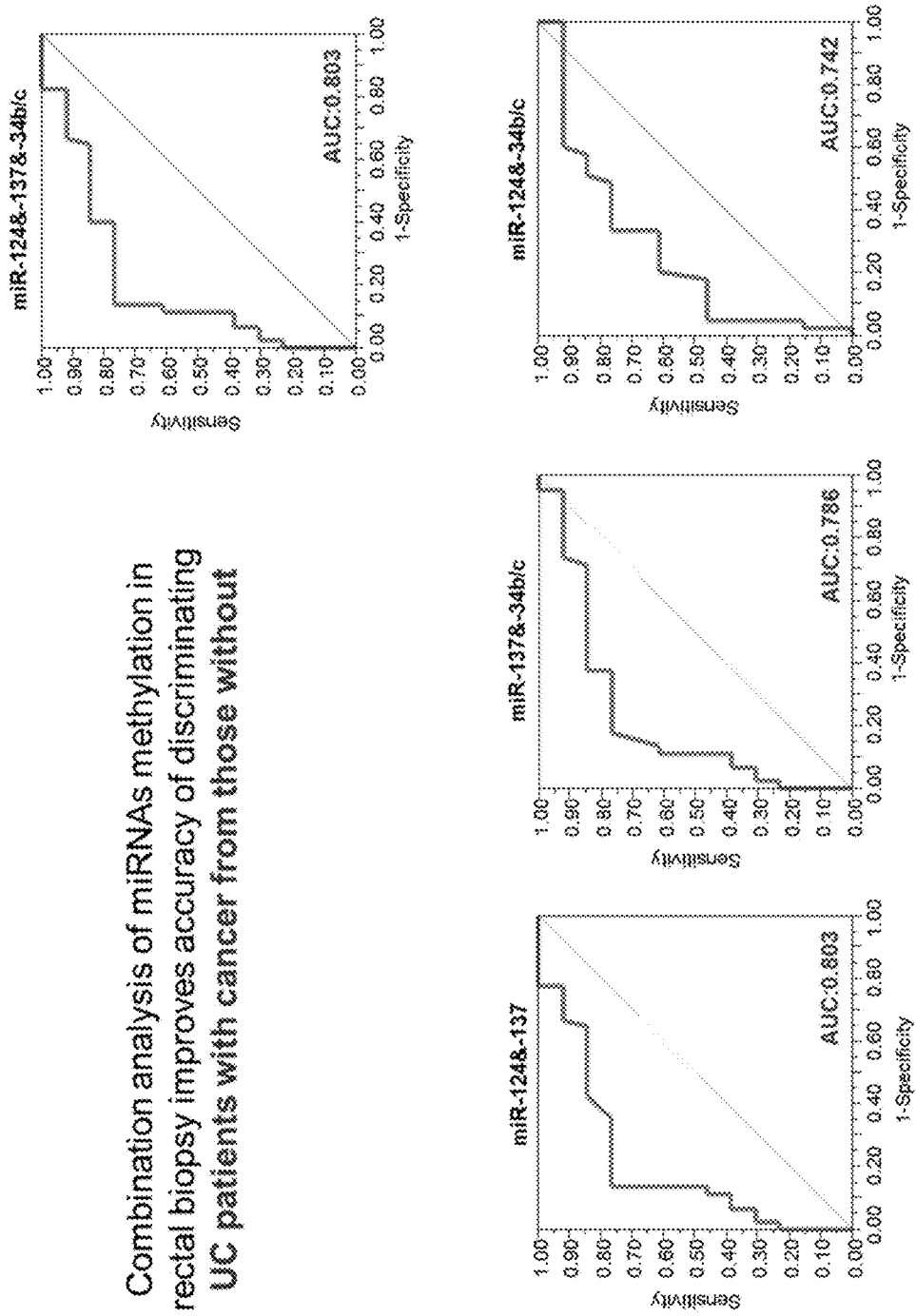
FIG. 10: Discrimination accuracy of cancerous vs. non-cancerous UC mucosa by combination analysis of miRNA methylation.
Figure 11:
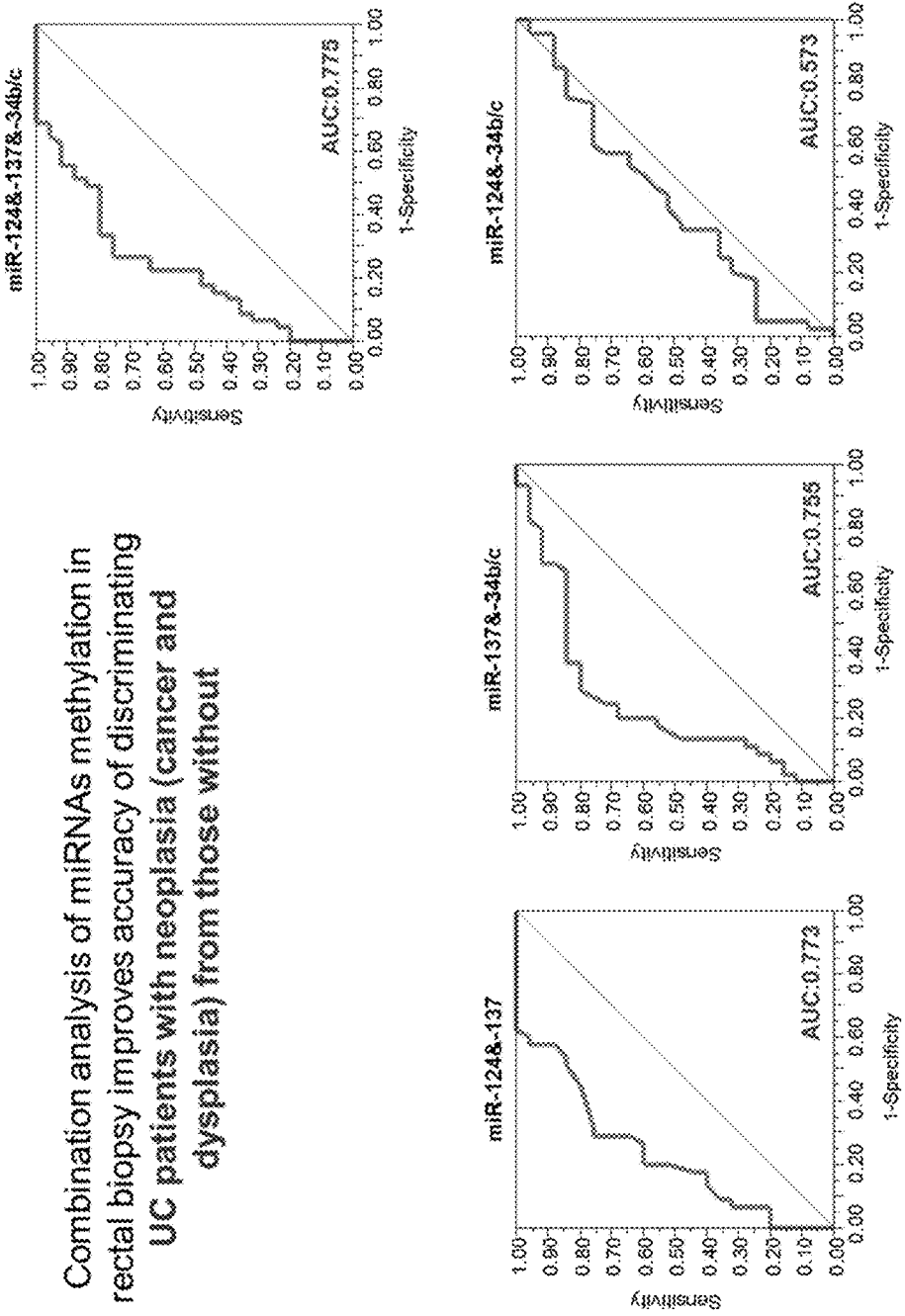
FIG. 11: Discrimination accuracy of neoplasia (cancer and dysplasia) vs. non-neoplastic UC mucosa by combination analysis of miRNA methylation.
Figure 12:
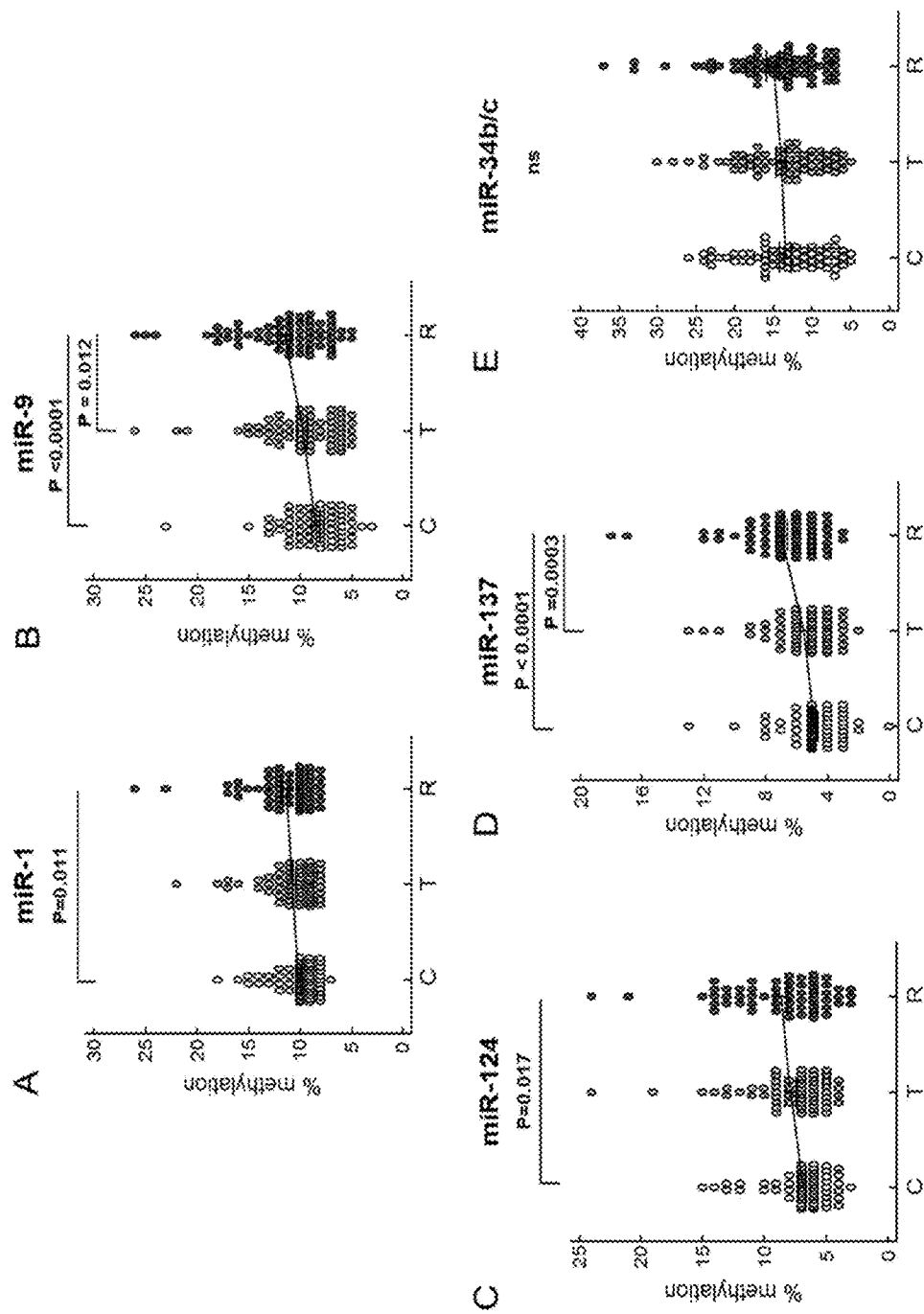
FIG. 12: MiR-1, -9, -124, -137 and -34b/c methylation levels in non-neoplastic UC mucosa. (n=186). Dot plots of miRNAs methylation levels in mucosa at Cecum (C; n=62), Transverse colon (T; n=62) and Rectum (R; n=62) (miR-1 (A), -9 (B), -124 (C), -137 (D), and -34b/c (E), respectively). Statistically significant differences were determined using Mann-Whitney tests and Kruskal-Wallis tests.
Figure 13:
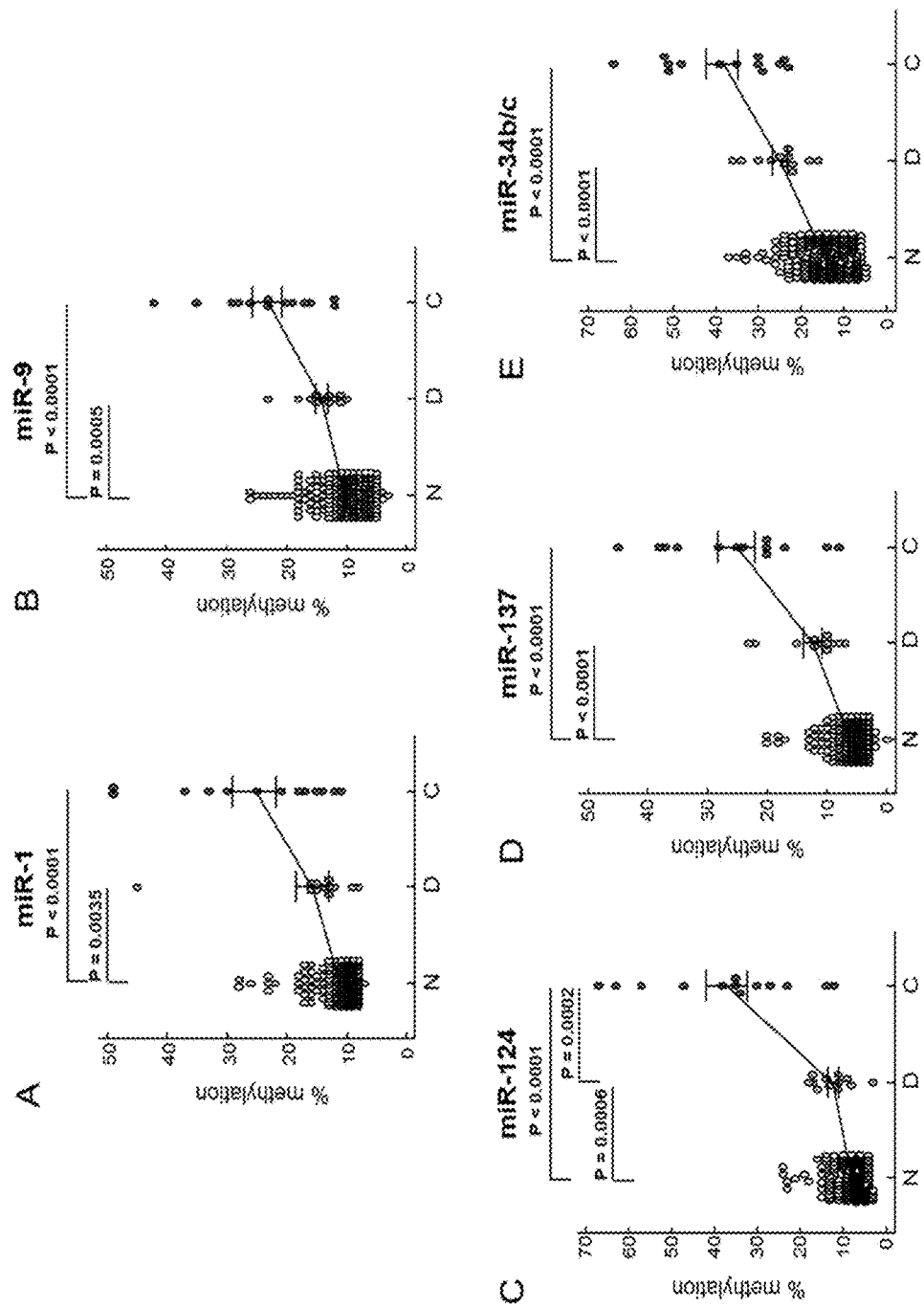
FIG. 13: MiR-1, -9, -124, -137 and -34b/c methylation levels in UC mucosa by disease status (n=236). (A) Dot plots of miR-1 methylation levels in non-neoplastic UC mucosa (N; n=211), Dysplasia (D; n=12) and Cancer (C; n=13). (B) Dot plots of miR-9 methylation levels in non-neoplastic UC mucosa (N; n=211), Dysplasia (D; n=12) and Cancer (C; n=13). (C) Dot plots of miR-124 methylation levels in non-neoplastic UC mucosa (N; n=211), Dysplasia (D; n=12) and Cancer (C; n=13). (D) Dot plots of miR-137 methylation levels in non-neoplastic UC mucosa (N; n=211), Dysplasia (D; n=12) and Cancer (C; n=13). (C) Dot plots of miR-34b/c methylation levels in non-neoplastic UC mucosa (N; n=211), Dysplasia (D; n=12) and Cancer (C; n=13). Statistically significant differences were determined using Mann-Whitney tests.

DNA methylation analysis. DNA was bisulfite modified using the EZ DNA methylation Gold Kit (Zymo Research, Irvine, Calif., USA). Methylation of putative miR-124, miR-137 and miR-34b/c promoter regions were quantified by bisulfite pyrosequencing (PSQ HS 96A pyrosequencing system, Qiagen). Primers are shown in Table 5. Methylation levels of some CpG sites were analyzed. Methylation levels of each sample are represented as the mean value of methylation levels of some CpG sites in each microRNA promoter regions (FIG. 7).

TABLE 4

Histological data of UC patients with neoplasia

| Cancer patients | | | | | Dysplasia Patients | |
|---|---|---|---|---|---|---|
| Patient No. | TNM | | | Histological Differentiation | Patient No. | Degree of Dysplasia |
| 1 | T1 | N0 | M0 | Moderate | 1 | LGD |
| 2 | T4 | N1 | M0 | Poor | 2 | LGD |
| 3 | T2 | N0 | M0 | Well | 3 | LGD |
| 4 | T3 | N0 | M0 | Well | 4 | LGD |
| 5 | T1 | N0 | M0 | Poor | 5 | LGD |
| 6 | T3 | N0 | M0 | Well | 6 | LGD |
| 7 | T3 | N0 | M0 | Moderate | 7 | HGD |
| 8 | T3 | N0 | M0 | Well | 8 | LGD |
| 9 | Tis | N0 | M0 | Well | 9 | LGD |
| 10 | T3 | N0 | M0 | Well | 10 | LGD |
| 11 | Tis | N0 | M0 | Moderate | 11 | HGD |
| 12 | Tis | N0 | M0 | Well | 12 | HGD |
| 13 | T4 | N1 | M1 | Poor | | |

LGD: Low Grade Dysplasia,
HGD: High Grade Dysplasia

TABLE 5

Pyrosequencing Primers

| | Forward | SEQ ID NO. | Reverse | SEQ ID NO. |
|---|---|---|---|---|
| miR-124 | GGGTGTTTTAGTTTTAGGA | 1 | 5'-biotin-CCACACTTCTCCCCTTT | 6 |
| miR-124-seq | | | CCACACTTCTCCCCTT | 7 |
| miR-137 | TGGATTTTTTTTGAAAT | 2 | 5'-biotin-CCACCAAAACTCTTACTACTC | 8 |
| miR-137-seq | ATTTTTTTTTAGGGAAAT | 3 | | |
| miR-34b/c | GAAGGGGAAAGGAAAAG | 4 | 5'-biotin-CCCAAAAATACCAAACCTC | 9 |
| miR-34b/c-seq | GAAGGGGAAAGGAAAA | 5 | | |

Seq: sequence primer

RNA isolation and qRT-PCT from FFPE tissues. Total RNA was isolated from FFPE samples using the RecoverAll Total Nucleic Acid Isolation Kit (Ambion Inc., Austin, Tex.). Briefly, tissue sections were microdissected to enrich for neoplastic cells, followed by deparaffinization and RNA extraction using the manufacturer's protocol. Total RNA was eluted in the appropriate buffer, and quantified using a NanoDrop Spectrophotometer (NanoDrop Technologies, Wilmington, Del.). Reverse transcription reactions were carried out using the TaqMan MicroRNA Reverse Transcription Kit (Applied Biosystems, Foster City, Calif.) in a total reaction volume of 15 uL. MiR-124, miR-137, miR-34c and miR-16 were quantified in duplicate by qRT-PCR, using MicroRNA Assay Kits (Applied Biosystems). qRT-PCR was performed on an Applied Biosystems 7000 Sequence Detection System, with the following cycling conditions: 95° C. for 10 min, followed by 45 cycles of 95° C. for 15 s and 60° C. for 1 min. Cycle threshold (Ct) values were calculated with SDS 1.4 software (Applied Biosystems).

Calculation of miRNA expression. Expression levels of tissue miRNAs were normalized against miR-16 using the $2^{-\Delta Ct}$ method. Differences between the groups are presented as ΔCt, indicating differences between Ct values of miRNAs of interest and Ct values of normalizer miRNAs.

Statistical analyses. Statistical differences in tissue miRNA methylation and expression levels were determined using Mann-Whitney U or Kruskal-Wallis tests as appropriate. Receiver operating characteristic (ROC) curves were established to distinguish UC with neoplasia or from UC with non-neoplasia. Predictive accuracy was determined by measuring area under ROC curve (AUC), specificity and sensitivity. A predictive model with AUC of >0.7 was considered to show good discrimination; AUC of 0.5 is equivalent to a "coin toss." Logistic regression analysis was performed to select categories associated with UC patients with neoplasia. All P-values are two-sided; P≤0.05 was considered significant. All statistical analyses were carried out using Medcalc 12.3 (Broekstraat 52, 9030, Mariakerke, Belgium).

Example 4

Materials and Methods

Figure 16:
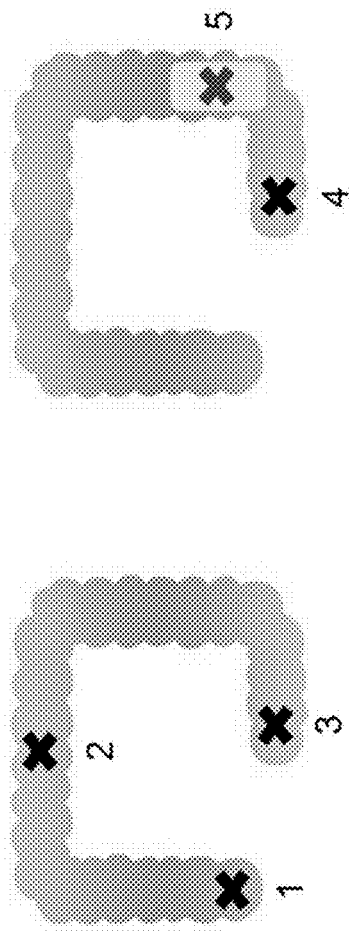
FIG. 16: Flow chart for current methylation analysis in UC. Sample 1, 2 and 3 mean tissues in Cecum, Transverse colon and Rectum from UC patients without neoplasia, respectively. Sample 4 and 5 mean tissues in rectum and neoplasia from UC patients with neoplasia, respectively.

Patients and samples. We studied 236 colorectal epithelia samples, including with 211 non-neoplastic and 25 neoplastic tissues, from 87 patients with UC. Diagnosis of UC was based on medical history, endoscopic findings, histological examination, laboratory tests and clinical disease presentation. Extent of disease was characterized as left-side colitis or total colitis; inflammatory severity was classified as "mild," "moderate" or "severe," based on clinical, endoscopic and histological findings. Patients with right-sided colitis, segmental colitis and proctitis, acute fulminating UC, or who were presenting with their first attacks were excluded from evaluation. Twenty-five patients had neoplasia (Table 9); 62 patients had no neoplasia. In non-neoplastic patients, multiple samples were taken from 3 regions (cecum, transverse colon and rectum); 2 regions (neoplastic tissue and rectum without neoplasia) were sampled from patients with neoplasia (FIG. 16). All samples were retrieved from colectomy specimens, which were resected at Mie University Hospital between 2005 and 2011. Specimen collection and studies were approved by the Institutional Review Broad (IRB) at the Mie University Hospital in Japan and Baylor Medical Center at Dallas in USA. All participants provided written consent and willingness to donate their tissue samples for research.

TABLE 9

Histological data of UC patients with neoplasia

| Cancer Patients | | | | Dysplasia Patients | |
|---|---|---|---|---|---|
| Patient No. | TNM | | Histological Differentiation | Patient No. | Degree of Dysplasia |
| 1 | T1 | N0 M0 | moderate | 1 | LGD |
| 2 | T4 | N1 M0 | poor | 2 | LGD |
| 3 | T2 | N0 M0 | well | 3 | LGD |
| 4 | T3 | N0 M0 | well | 4 | LGD |
| 5 | T1 | N0 M0 | poor | 5 | LGD |
| 6 | T3 | N0 M0 | well | 6 | LGD |
| 7 | T3 | N0 M0 | moderate | 7 | HGD |
| 8 | T3 | N0 M0 | well | 8 | LGD |
| 9 | Tis | N0 M0 | well | 9 | LGD |
| 10 | T3 | N0 M0 | well | 10 | LGD |
| 11 | Tis | N0 M0 | moderate | 11 | HGD |
| 12 | Tis | N0 M0 | well | 12 | HGD |
| 13 | T4 | N1 M1 | poor | | |

LGD: Low Grade Dysplasia,
HGD: High Grade Dysplasia

DNA extraction from formalin-fixed paraffin-embedded (FFPE) samples. FFPE samples were cut serially at 10 μM. Based on histological findings, the tissue of each region was microdissected; DNA was extracted using the QIAmp DNA FFPE tissue kit (Qiagen, Valencia, Calif., USA) according to the manufacturer's protocol.

Figure 17:
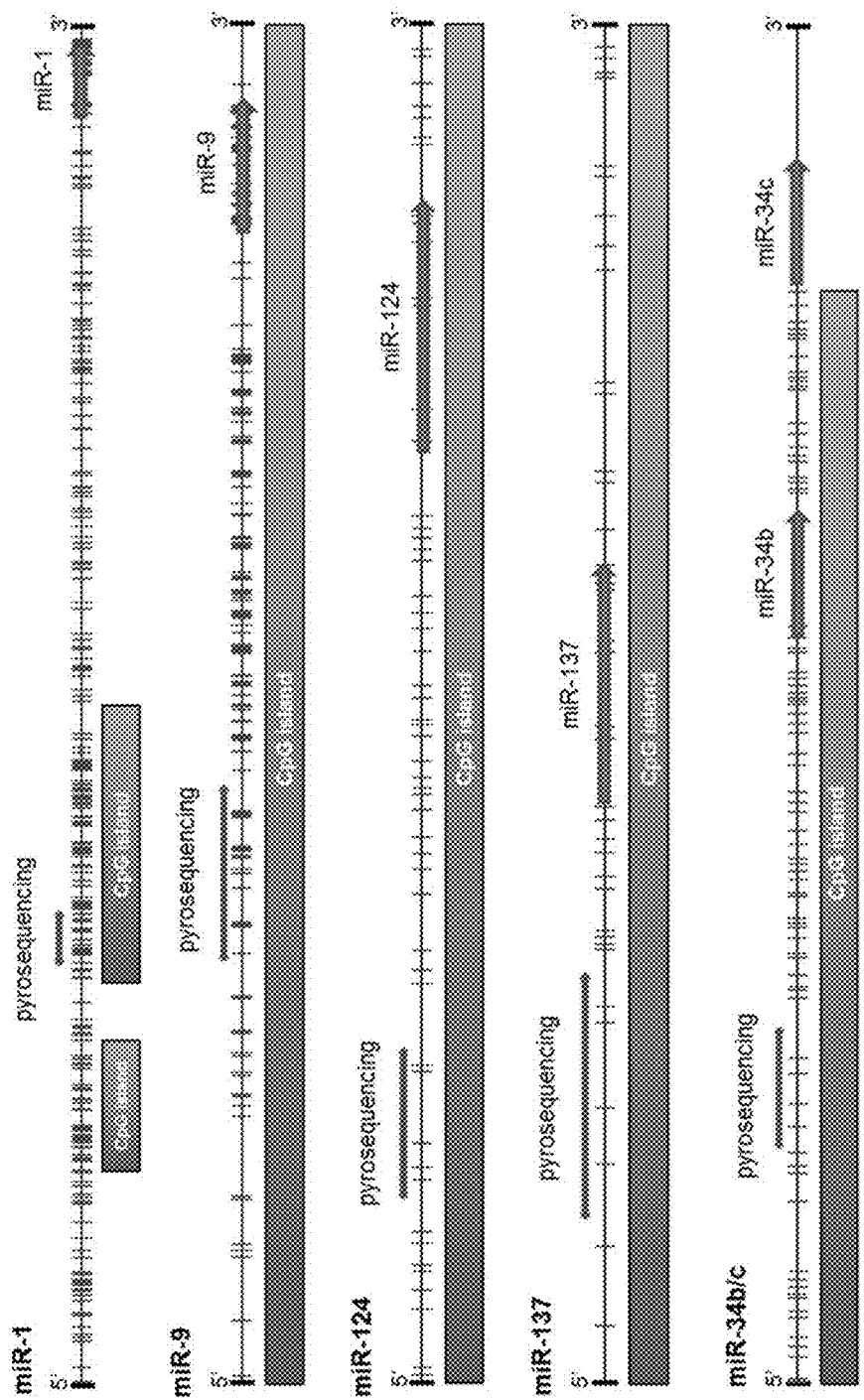
FIG. 17: Methylation analysis of miR-1, -9, -124, -137 and -34b/c CpG islands. Maps of miR-1, -9, -124, -137 and -34b/c CpG islands and positions of miR-1, -9, -124, -137, -34b and -34c sequences and PCR products used for bisulfite pyrosequencing analysis. Orange box: CpG island; vertical tick marks: CpG sites.
Figure 18:
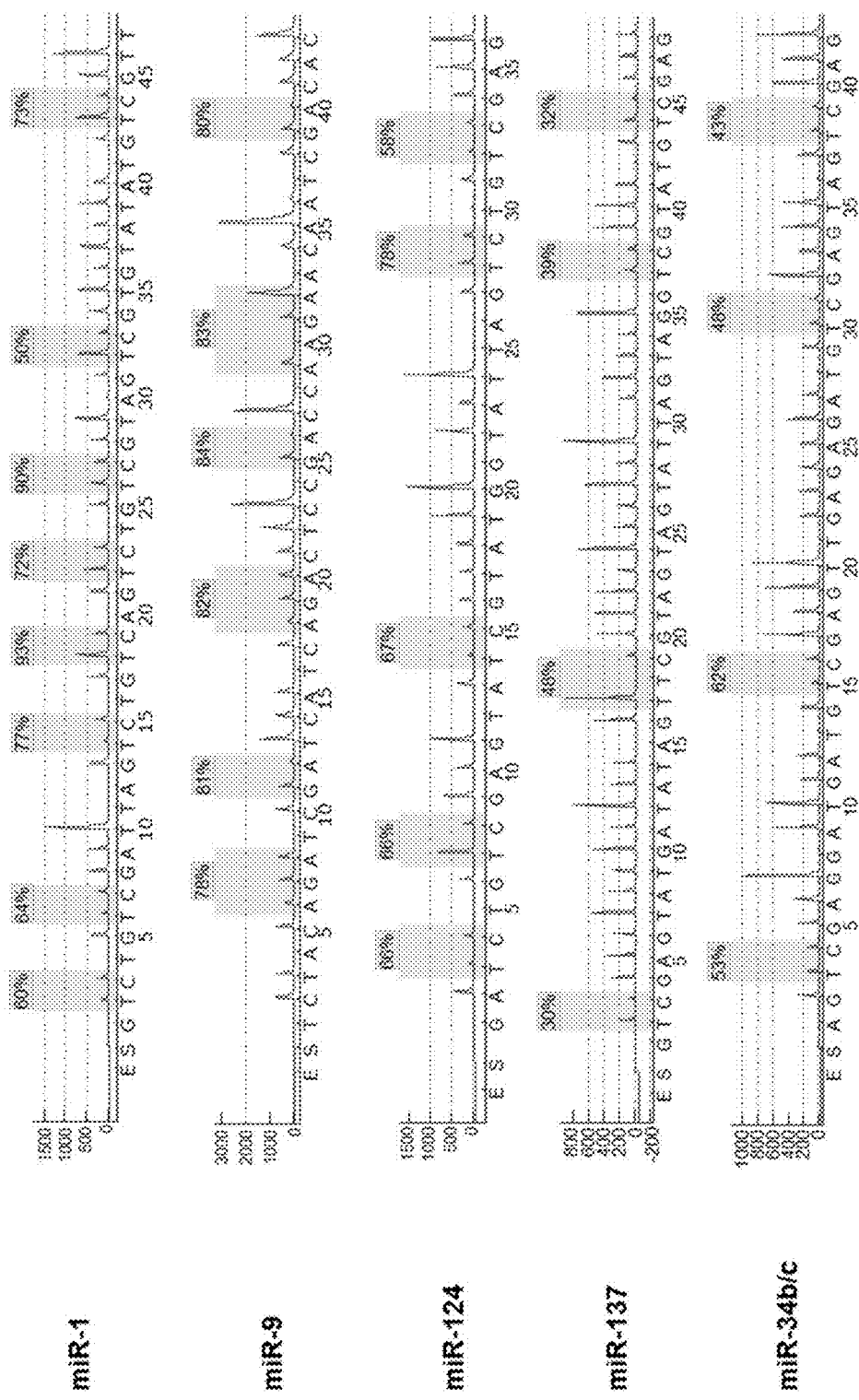
FIG. 18: Results of bisulfite pyrosequencing miR-1, -9, -124, -137 and -34b/c. Methylation percentages of some CpG sites (marked in gray vertical boxes) are shown in the pyrogram.

DNA methylation analysis. DNA was bisulfite modified using the EZ DNA methylation Gold Kit (Zymo Research, Irvine, Calif., USA). Methylation of putative miR-1, -9, -124, miR-137 and miR-34b/c promoter regions were quantified by bisulfite pyrosequencing (PSQ HS 96A pyrosequencing system, Qiagen). Primers are shown in Table 10. Methylation levels of some CpG sites were analyzed. Methylation levels of each sample are represented as the mean value of methylation levels of some CpG sites in each microRNA promoter regions (FIG. 17 and FIG. 18).

TABLE 10

Pyrosequencing primers

| | Forward | SEQ ID NO: | Reverse | SEQ ID NO: |
|---|---|---|---|---|
| miR-1 | TTYGGAGGAGGTGGTTGGTGTTGT | 10 | AAACACCCCTAAACCRAACTAATAAC | 20 |
| miR-1-seq | TGTAGTATTTTTTAGGGAGT | 11 | | |
| miR-9 | 5'-biotin-GGTTTTTGAGGGTAGAGG | 12 | CACCACCCAACCTTACAA | 21 |
| miR-9-seq | CACCCAACCTTACAATAAC | 13 | | |
| miR-124 | GGGTGTTTTAGTTTTAGGA | 14 | 5'-biotin-CCACACTTCTCCCCTTT | 22 |
| miR-124-seq | CCACACTTCTCCCCTT | 15 | | |
| miR-137 | TGGATTTTTTTTAGGGAAAT | 16 | 5'-biotin-CCACCAAAACTCTTACTACTC | 23 |
| miR-137-seq | ATTTTTTTTAGGGAAAT | 17 | | |

TABLE 10-continued

Pyrosequencing primers

| | Forward | SEQ ID NO: | Reverse | SEQ ID NO: |
|---|---|---|---|---|
| miR-34b/c | GAAGGGGAAAGGAAAAG | 18 | 5'-biotin-CCCAAAAATACCAAACCTC | 24 |
| miR-34b/c-seq | GAAGGGGAAAGGAAAA | 19 | | | seq: sequence primer

RNA isolation and qRT-PCR from FFPE tissues. Total RNA was isolated from FFPE samples using the RecoverAll Total Nucleic Acid Isolation Kit (Ambion Inc., Austin, Tex.). Briefly, tissue sections were microdissected to enrich for neoplastic cells, followed by deparaffinization and RNA extraction using the manufacturer's protocol. Total RNA was eluted in the appropriate buffer, and quantified using a NanoDrop Spectrophotometer (NanoDrop Technologies, Wilmington, Del.). Reverse transcription reactions were carried out using the TaqMan MicroRNA Reverse Transcription Kit (Applied Biosystems, Foster City, Calif.) in a total reaction volume of 15 uL. MiR-1, -9, -124, miR-137, miR-34c and miR-16 were quantified in duplicate by qRT-PCR, using MicroRNA Assay Kits (Applied Biosystems). qRT-PCR was performed on an Applied Biosystems 7000 Sequence Detection System, with the following cycling conditions: 95° C. for 10 min, followed by 45 cycles of 95° C. for 15 s and 60° C. for 1 min. Cycle threshold (Ct) values were calculated with SDS 1.4 software (Applied Biosystems).

Calculation of miRNA expression. Expression levels of tissue miRNAs were normalized against miR-16 using the $2^{-\Delta Ct}$ method. Differences between the groups are presented as ΔCt, indicating differences between Ct values of miRNAs of interest and Ct values of normalizer miRNAs.

Statistical analyses. Statistical differences in tissue miRNA methylation and expression levels were determined using Mann-Whitney U or Kruskal-Wallis tests as appropriate. Differences between categorized groups were estimated by the Pearson's $\chi^2$-test. Results are expressed as means±S.D. The Spearman rank correlation test was conducted for statistical correlations. Receiver operating characteristic (ROC) curves were established to distinguish UC with neoplasia or from UC with non-neoplasia. Predictive accuracy was determined by measuring area under ROC curve (AUC), specificity and sensitivity. A predictive model with AUC of >0.7 was considered to show good discrimination; AUC of 0.5 is equivalent to a "coin toss." Logistic regression analysis was performed to select categories associated with UC patients with neoplasia. After univariate analysis, variables with a P-value<0.05 were selected for multivariate analysis using logistic regression analysis. All P-values are two-sided; P<0.05 was considered significant. All statistical analyses were carried out using Medcalc 12.7 (Broekstraat 52, 9030, Mariakerke, Belgium).

Characteristics of UC patients. Clinicopathologic features of the 87 patients with UC are shown in Table 11. Patients with UC and with or without neoplasia showed no significantly difference of gender, age at onset, age at surgery, extent of disease and inflammatory degree. However, median disease durations were significantly longer in patients with dysplasia (8 years: 1-28) and cancer (12 years: 1-24) than in patients without neoplasia (6 years: 1-28). (P=0.024; Table 11).

TABLE 11

Patient Characteristics

| Characteristic | | Patients with non-neoplasia (n = 62) | Patients with dysplasia (n = 12) | Patients with cancer (n = 13) | P |
|---|---|---|---|---|---|
| Gender | Male | 34 | 6 | 10 | 0.29 |
| | Female | 28 | 6 | 3 | |
| Age at diagnosis of UC in years (range) | | 27 (5-61) | 30.5 (20-38) | 29 (17-55) | 0.48 |
| Age at surgery for UC in years (range) | | 34 (7-62) | 36.5 (27-56) | 39 (28-74) | 0.31 |
| Extent of disease | Total colitis | 45 | 8 | 8 | |
| | Left-side colitis | 17 | 4 | 5 | 0.7 |
| Duration of disease in years (range) | | 6(1-28) | 8 (1-28) | 12 (1-24) | 0.024 |
| Degree of inflammation | Mild | 26 | 5 | 9 | |
| | Moderate | 30 | 6 | 4 | 0.43 |
| | Severe | 6 | 1 | 0 | |

Methylation levels of miR-1, -9, -124, -137 and 34b/c in non-neoplastic UC tissues are significantly associated with age, disease duration and colorectal location. We evaluated associations between miR-1, -9, -124, -137 and 34b/c methylation levels in non-neoplastic mucosa from UC and clinicopathological findings subdivided by location in the colorectum (n=186). MiR-1, -9, -124 and -137 methylation levels showed stepwise increases from cecum to rectum; rectal methylation levels of all of these miRNAs were significantly higher than in the cecum (miR-1: 10.16±2.17% vs. 11.42±3.33%, P=0.011; miR-9: 8.5±3.13% vs. 11.58±4.66%, P<0.0001; miR-124: 6.92±2.52% vs. 8.65±4.12%, P=0.017; miR-137: 4.86±1.97% vs. 6.97±2.81%, P<0.0001); methylation of miR-34b/c also tended to increase (miR-34b/c: 13.45±5.52% vs. 15.05±6.63%, P=0.24) (FIG. 12A-12E). Furthermore, miR-1, -9, -124 and -137 methylation levels, which methylation levels revealed the significant correlation with location dependent-manner, were significantly associated with age at diagnosis (miR-1:P=0.001; miR-9:P=0.002; miR-124: P=0.001; miR-137: P=0.0009), age at operation (miR-1: P=0.001; miR-9:P=0.002; miR-124: P=0.002; miR-137: P=0.0004) and long disease duration (miR-1:P=0.011; miR-9:P=0.026; miR-124: P=0.008; miR-137: P=0.009) in non-neoplastic tissues from rectal mucosa (Tables 12, 13, 14, and 15). In contrast, there was no association between miR-34b/c methylation and clinicopathological findings (Table 16). Collectively, miR-1, -9, -124 and -137 could be age-related methylation in non-neoplastic rectum; rectal methylation in both miRNAs showed higher levels compared to proximal colon in UC patients.

TABLE 12

Association between miR-1 methylation levels in UC mucosa without neoplasia and clinical findings, subdivided by location

| | | miR-1 methylation levels (mean ± SD) | | | | | |
|---|---|---|---|---|---|---|---|
| | Category | Cecum | P | Transverse | P | Rectum | P |
| Gender | Male | 10.2 ± 2.3 | 0.85 | 10.9 ± 3.2 | 0.59 | 11.6 ± 3.3 | 0.54 |
| | Female | 10.1 ± 2.0 | | 10.6 ± 1.9 | | 11.1 ± 3.4 | |
| Age at diagnosis | ≤27 yr* | 10.3 ± 2.5 | 0.86 | 10.2 ± 2.7 | 0.02 | 10.3 ± 2.3 | 0.001 |
| | >27 yr* | 10.1 ± 1.8 | | 11.3 ± 2.6 | | 12.5 ± 3.8 | |
| Age at operation | ≤34 yr* | 10.2 ± 2.3 | 0.92 | 10.3 ± 2.7 | 0.06 | 10.3 ± 2.2 | 0.001 |
| | >34 yr* | 10.2 ± 2.0 | | 11.3 ± 2.7 | | 12.6 ± 3.9 | |
| disease duration | ≤6 yr* | 9.5 ± 1.4 | 0.05 | 9.7 ± 1.2 | 0.002 | 10.4 ± 2.2 | 0.011 |
| | >6 yr* | 10.8 ± 2.6 | | 11.9 ± 3.3 | | 12.5 ± 4.0 | |
| inflammation degree | mild | 10.4 ± 2.0 | 0.16 | 10.6 ± 2.3 | 0.99 | 10.9 ± 2.1 | 0.82 |
| | moderate/severe | 10.0 ± 2.3 | | 10.9 ± 3.0 | | 11.8 ± 3.9 | |
| colitis type | left side | 10.2 ± 1.6 | 0.61 | 10.6 ± 2.1 | 0.89 | 11.3 ± 2.4 | 0.69 |
| | total | 10.2 ± 2.4 | | 10.8 ± 2.9 | | 11.5 ± 3.6 | |

*The median age at onset, median age at surgery and median disease duration are 27, 34, and 6 years, respectively.

TABLE 13

Association between miR-9 methylation levels in UC mucosa without neoplasia and clinical findings, subdivided by location.

| | | miR-9 methylation levels (mean ± SD) | | | | | |
|---|---|---|---|---|---|---|---|
| | Category | Cecum | P | Transverse | P | Rectum | P |
| Gender | Male | 8.2 ± 3.6 | 0.16 | 10.1 ± 4.9 | 0.86 | 11.6 ± 4.7 | 0.86 |
| | Female | 8.9 ± 2.5 | | 9.3 ± 3.2 | | 11.5 ± 4.7 | |
| Age at diagnosis | ≤27 yr* | 8.3 ± 3.7 | 0.09 | 9.1 ± 4.9 | 0.01 | 10.2 ± 4.7 | 0.002 |
| | >27 yr* | 8.7 ± 2.5 | | 10.5 ± 3.3 | | 13.0 ± 4.3 | |
| Age at operation | ≤34 yr* | 8.4 ± 3.7 | 0.22 | 9.3 ± 4.9 | 0.07 | 9.9 ± 4.0 | 0.002 |
| | >34 yr* | 8.6 ± 2.5 | | 10.2 ± 3.4 | | 13.2 ± 4.8 | |
| disease duration | ≤6 yr* | 7.5 ± 2.2 | 0.006 | 8.6 ± 2.7 | 0.04 | 10.1 ± 3.5 | 0.026 |
| | >6 yr* | 9.6 ± 3.6 | | 11.0 ± 5.1 | | 13.1 ± 5.3 | |
| inflammation degree | mild | 8.0 ± 2.6 | 0.22 | 8.0 ± 2.7 | 0.005 | 10.8 ± 4.3 | 0.2 |
| | moderate/severe | 8.9 ± 3.4 | | 10.9 ± 4.6 | | 12.1 ± 4.9 | |
| colitis type | left side | 8.4 ± 2.2 | 0.86 | 8.5 ± 2.6 | 0.22 | 11.7 ± 3.3 | 0.47 |
| | total | 8.5 ± 3.4 | | 10.2 ± 4.6 | | 11.5 ± 5.1 | |

*The median age at onset, median age at surgery and median disease duration are 27, 34, and 6 years, respectively.

TABLE 14

Association between miR-124 methylation levels in UC mucosa without neoplasia and clinical findings, subdivided by location.

| | | miR-124 methylation levels (mean ± SD) | | | | | |
|---|---|---|---|---|---|---|---|
| | Category | Cecum | P | Transverse | P | Rectum | P |
| Gender | Male | 6.6 ± 2.4 | 0.51 | 7.6 ± 3.4 | 0.28 | 8.6 ± 4.0 | 0.93 |
| | Female | 7.3 ± 2.7 | | 8.2 ± 3.8 | | 8.7 ± 4.4 | |
| Age at diagnosis | ≤27 yr* | 6.4 ± 2.3 | 0.1 | 7.0 ± 3.2 | 0.008 | 7.6 ± 4.8 | 0.001 |
| | >27 yr* | 7.4 ± 2.7 | | 8.7 ± 3.7 | | 9.7 ± 3.0 | |
| Age at operation | ≤34 yr* | 6.6 ± 2.3 | 0.36 | 7.2 ± 3.2 | 0.04 | 7.3 ± 3.7 | 0.002 |
| | >34 yr* | 7.2 ± 2.7 | | 8.6 ± 3.8 | | 10.0 ± 4.1 | |
| disease duration | ≤6 yr* | 6.3 ± 1.8 | 0.05 | 6.6 ± 1.8 | 0.008 | 7.2 ± 3.0 | 0.008 |
| | >6 yr* | 7.6 ± 3.0 | | 9.2 ± 4.4 | | 10.2 ± 4.7 | |
| inflammation degree | mild | 7.1 ± 3.0 | 0.82 | 6.9 ± 2.2 | 0.09 | 8.7 ± 4.6 | 0.96 |
| | moderate/severe | 6.8 ± 2.2 | | 8.5 ± 4.1 | | 8.6 ± 3.8 | |
| colitis type | left side | 7.4 ± 3.0 | 0.55 | 8.4 ± 4.7 | 0.92 | 8.9 ± 3.3 | 0.38 |
| | total | 6.7 ± 2.3 | | 7.7 ± 3.0 | | 8.6 ± 4.4 | |

*The median age at onset, median age at surgery and median disease duration are 27, 34, and 6 years, respectively.

TABLE 15

Association between miR-137 methylation levels in UC mucosa
without neoplasia and clinical findings, subdivided by location.

| | | miR-137 methylation levels (mean ± SD) | | | | | |
|---|---|---|---|---|---|---|---|
| Category | | Cecum | P | Transverse | P | Rectum | P |
| Gender | Male | 4.6 ± 1.8 | 0.13 | 5.4 ± 2.4 | 0.21 | 6.4 ± 2.3 | 0.11 |
| | Female | 5.2 ± 2.2 | | 5.7 ± 1.8 | | 7.6 ± 3.2 | |
| Age at diagnosis | ≤27 yr* | 4.5 ± 1.7 | 0.09 | 5.1 ± 2.3 | 0.02 | 6.1 ± 2.8 | 0.0009 |
| | >27 yr* | 5.3 ± 2.1 | | 5.9 ± 1.9 | | 7.8 ± 2.6 | |
| Age at operation | ≤34 yr* | 4.6 ± 1.8 | 0.45 | 5.2 ± 2.3 | 0.15 | 5.8 ± 1.8 | 0.0004 |
| | >34 yr* | 5.1 ± 2.2 | | 5.8 ± 2.0 | | 8.2 ± 3.2 | |
| disease duration | ≤6 yr* | 4.3 ± 1.7 | 0.01 | 5.0 ± 1.4 | 0.08 | 6.1 ± 1.8 | 0.009 |
| | >6 yr* | 5.5 ± 2.1 | | 6.1 ± 2.6 | | 7.9 ± 3.3 | |
| inflammation degree | mild | 5.0 ± 2.4 | 0.74 | 5.2 ± 1.4 | 0.69 | 7.5 ± 3.6 | 0.58 |
| | moderate/severe | 4.8 ± 1.7 | | 5.7 ± 2.5 | | 6.6 ± 2.1 | |
| colitis type | left side | 5.2 ± 2.9 | 0.79 | 5.6 ± 2.2 | 0.97 | 7.8 ± 3.2 | 0.13 |
| | total | 4.7 ± 1.5 | | 5.5 ± 2.1 | | 6.6 ± 2.6 | |

*The median age at onset, median age at surgery and median disease duration are 27, 34, and 6 years, respectively.

TABLE 16

Association between miR-34b/c methylation levels in UC mucosa
without neoplasia and clinical findings subdivided by location

| | | miR-34bc methylation levels (mean ± SD) | | | | | |
|---|---|---|---|---|---|---|---|
| Category | | Cecum | P | Transverse | P | Rectum | P |
| Gender | Male | 13.2 ± 5.5 | 0.71 | 15.0 ± 6.7 | 0.28 | 15.1 ± 7.3 | 0.59 |
| | Female | 13.8 ± 5.6 | | 12.7 ± 3.9 | | 15.0 ± 5.9 | |
| Age at diagnosis | ≤27 yr* | 13.5 ± 6.3 | 0.81 | 13.1 ± 5.7 | 0.15 | 14.5 ± 8.0 | 0.1 |
| | >27 yr* | 13.4 ± 4.7 | | 14.9 ± 5.6 | | 15.6 ± 5.0 | |
| Age at operation | ≤34 yr* | 13.3 ± 5.9 | 0.68 | 13.3 ± 5.7 | 0.31 | 14.3 ± 6.9 | 0.24 |
| | >34 yr* | 13.6 ± 5.2 | | 14.6 ± 5.7 | | 15.8 ± 6.4 | |
| disease duration | ≤6 yr* | 13.7 ± 6.1 | 0.86 | 13.7 ± 5.8 | 0.62 | 14.0 ± 6.3 | 0.17 |
| | >6 yr* | 13.2 ± 4.9 | | 14.3 ± 5.7 | | 16.2 ± 6.9 | |
| inflammation degree | mild | 14.5 ± 5.8 | 0.23 | 14.1 ± 6.3 | 0.89 | 15.2 ± 7.3 | 0.94 |
| | moderate/severe | 12.7 ± 5.3 | | 13.9 ± 5.3 | | 15.0 ± 6.2 | |
| colitis type | left side | 14.3 ± 6.3 | 0.57 | 14.0 ± 5.9 | 0.96 | 14.5 ± 4.6 | 0.93 |
| | total | 13.1 ± 5.2 | | 14.0 ± 5.7 | | 15.3 ± 7.3 | |

*The median age at onset, median age at surgery and median disease duration are 27, 34, and 6 years, respectively.

Figure 14:
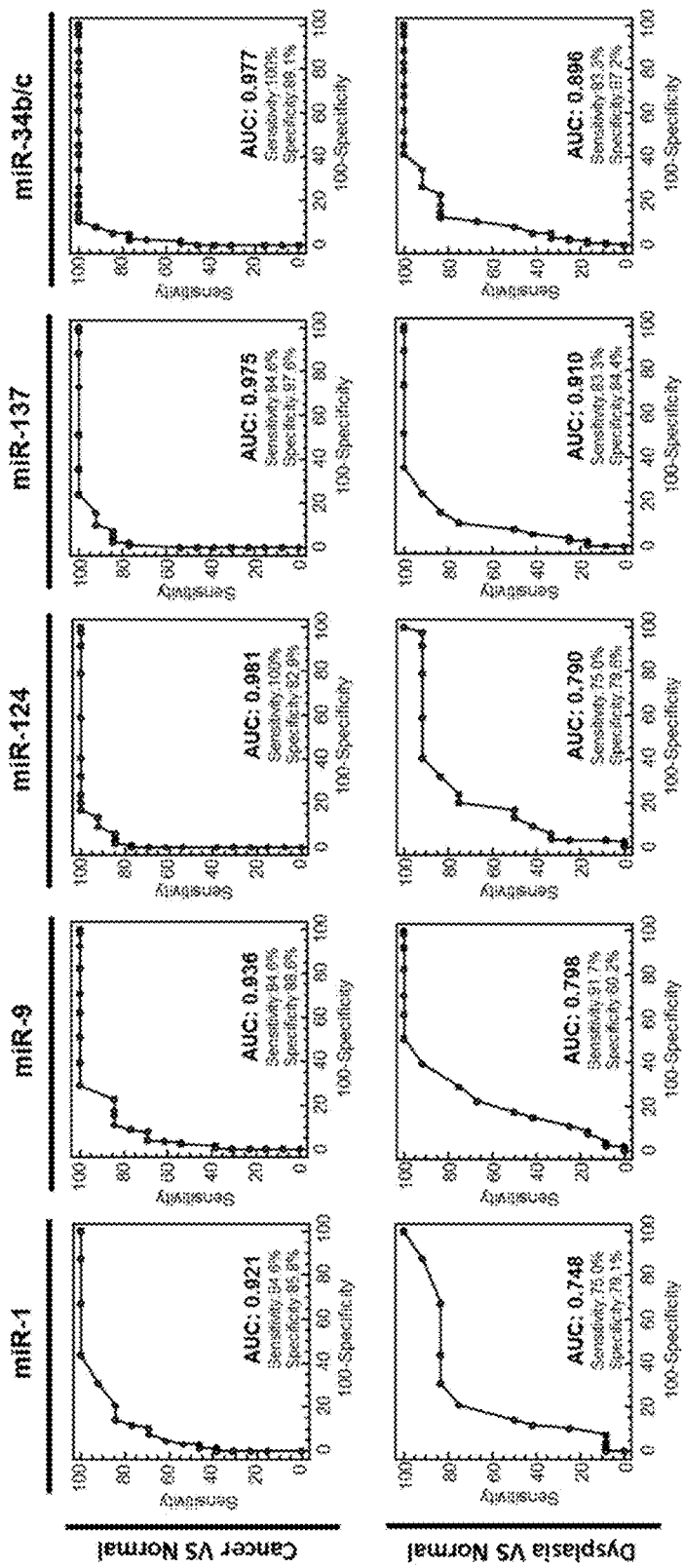
FIG. 14: ROC curve analysis of miR-1, -9, -124, -137 and -34b/c methylation, distinguishing UC-associated neoplasms from non-neoplastic UC mucosa. ROC curve analyses demonstrated that all 5 miRNAs methylation levels were robust in discriminating cancer from non-neoplastic UC mucosa, with AUC values of 0.921 (95% CI: 0.878-0.953), 0.936 (95% CI: 0.896-0.964), 0.981 (95% CI: 0.953-0.995), 0.975 (95% CI: 0.945-0.991) and 0.977 (95% CI: 0.948-0.992), respectively (Upper panels). Lower panels represented ROC curve analysis of these miRNAs methylation differentiating dysplasia from non-neoplastic UC mucosa, with AUC values of 0.748 (95% CI: 0.685-0.803), 0.798 (95% CI: 0.739-0.849), 0.790 (95% CI: 0.730-0.841), 0.910 (95% CI: 0.864-0.944) and 0.896 (95% CI: 0.848-0.933), respectively.

Methylation levels of miR-1, -9, -124, -137 and -34b/c in neoplastic tissues are significantly higher than those in non-neoplastic UC tissues. Next, to evaluate the diagnostic potential of miR-1, -9, -124, -137 and -34b/c methylation, a total of 236 tissue samples, including those with non-neoplasia (n=211), dysplasia (n=12) and cancer (n=13), from patients with UC were examined. Compared to non-neoplasia, methylation levels of all of these miRNAs were increased in cancerous tissues compared with normal epithelium of UC patients (miR-1: P<0.0001; miR-9: P<0.0001; miR-124: P<0.0001; miR-137: P<0.0001; miR-34b/c: P<0.0001; FIG. 13A-13E). Methylation levels of these miRNAs in dysplasia were also significantly increased compared to non-neoplastic UC mucosa (miR-1: P=0.0035; miR-9: P=0.0005; miR-124: P=0.0006; miR-137: P<0.0001; miR-34b/c: P<0.0001; FIG. 13A-13E). Our ROC analyses revealed that all 5 miRNAs methylation levels were robust in discriminating cancer from non-neoplasia, with AUC values of 0.921 (95% CI: 0.878-0.953), 0.936 (95% CI: 0.896-0.964), 0.981 (95% CI: 0.953-0.995), 0.975 (95% CI: 0.945-0.991) and 0.977 (95% CI: 0.948-0.992), respectively (FIG. 14). Even more important from a diagnostic perspective, all 5 miRNAs methylation levels could reliably differentiate dysplasia from non-neoplasia, as evidenced by AUC values of 0.748 (95% CI: 0.685-0.803), 0.798 (95% CI: 0.739-0.849), 0.790 (95% CI: 0.730-0.841), 0.910 (95% CI: 0.864-0.944) and 0.896 (95% CI: 0.848-0.933), respectively (FIG. 14). Collectively, these results suggest that methylation of these miRNAs occur early in the dysplasia-carcinoma sequence in UC and could be the basis of a method of diagnosing UC-associated neoplasia.

MiR-1, -9, -124, -137 and -34b/c methylation levels in non-neoplastic rectal tissues are biomarkers for patients with UC-associated neoplasia. To assess the potential usefulness of miR-1, -9, -124, -137 and -34b/c methylation levels as biomarkers for early diagnosis of UC-associated neoplasia, we first compared the methylation levels of these miRNAs in non-neoplastic rectal samples between patients with neoplasia and without. The results showed that all 5 miRNA methylation levels in non-neoplastic rectal tissues were significantly higher in patients with cancer than in those without (miR-1: 17.6±6.2 vs. 11.4±3.3, P=0.0001; miR-9: 14.3±4.7 vs. 11.6±4.7, P=0.027; miR-124: 13.4±5.9 vs. 8.6±4.1, P=0.003; miR-137: 11.5±5.1 vs. 7.0±2.8, P=0.0006; miR-34b/c: 20.8±5.5 vs. 15.0±6.6, P=0.0008; Table 17). Additionally, miR-1, -137 and -34b/c methylation levels in non-neoplastic tissues from patients with neoplasia (dysplasia and cancer) were significantly higher than from patients without (miR-1: 14.4±5.5 vs. 11.4±3.3, P=0.003; miR-137: 9.9±4.1 vs. 7.0±2.8, P<0.0001; miR-34b/c: 18.3±5.4 vs. 15.0±6.6, P=0.005; Table 17). These results can explain these miRNAs methylation "field defect" in UC mucosa.

TABLE 17

Methylation levels of miR-1, -9, -124, -137, and -34b/c in non-neoplastic rectal tissue of patients who have ulcerative colitis, with and without neoplasia.

| Category | Patients without cancer (n = 62) | Patients with cancer (n = 13) | P | Patients without neoplasia (n = 62) | Patients with neoplasia (n = 25) | P |
|---|---|---|---|---|---|---|
| miR-1 methylation (mean ± SD) | 11.4 ± 3.3 | 17.6 ± 6.2 | 0.0001 | 11.4 ± 3.3 | 14.4 ± 5.6 | 0.003 |
| miR-9 methylation (mean ± SD) | 11.6 ± 4.7 | 14.3 ± 4.7 | 0.027 | 11.6 ± 4.7 | 13.0 ± 4.0 | 0.05 |
| miR-124 methylation (mean ± SD) | 8.6 ± 4.1 | 13.4 ± 5.9 | 0.003 | 8.6 ± 4.1 | 10.5 ± 5.4 | 0.13 |
| miR-137 methylation (mean ± SD) | 7.0 ± 2.8 | 11.5 ± 5.1 | 0.0006 | 7.0 ± 2.8 | 9.9 ± 4.1 | <0.0001 |
| miR-34b/c methylation (mean ± SD) | 15.0 ± 6.6 | 20.8 ± 5.5 | 0.0008 | 15.0 ± 6.6 | 18.3 ± 5.4 | 0.005 |

SD: Standard deviation

Figure 15:
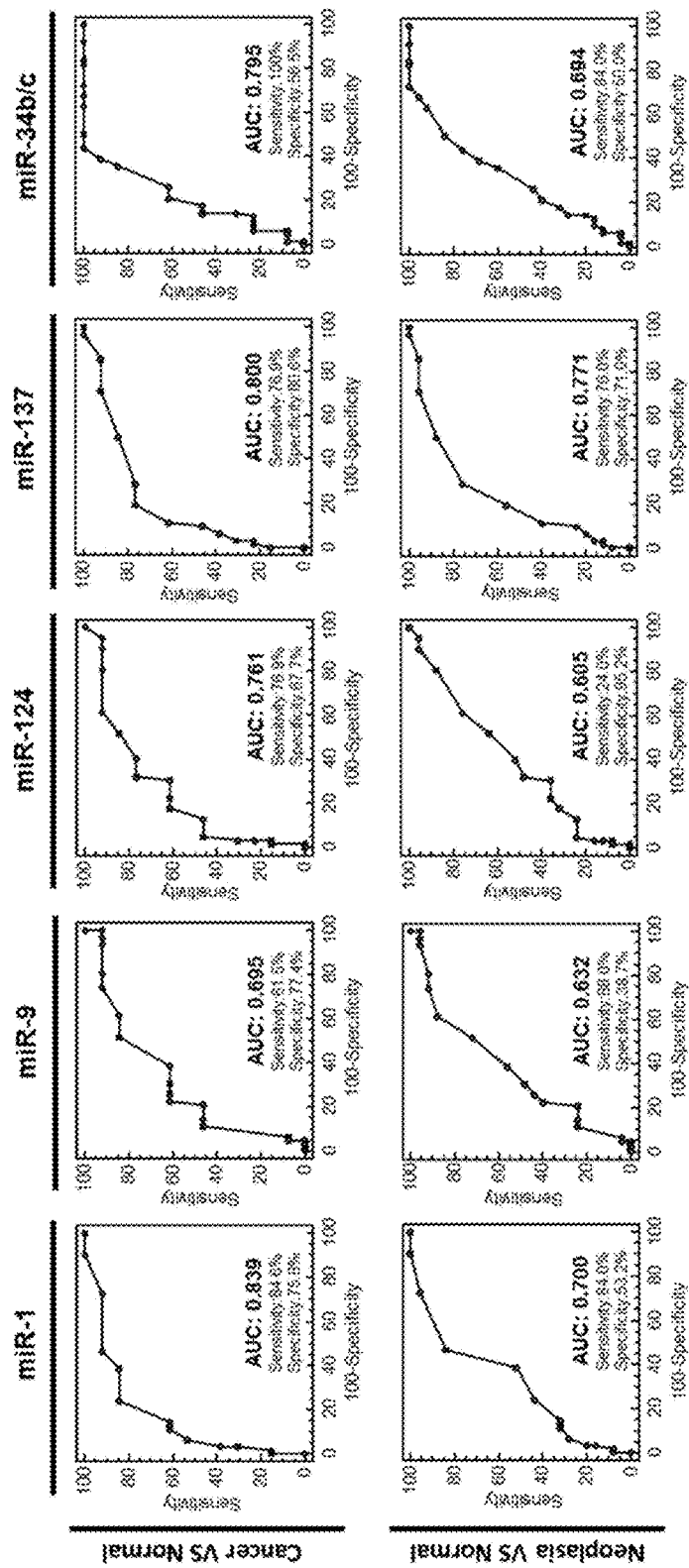
FIG. 15: ROC curve analysis of miR-1, -9, -124, -137 and -34b/c methylation in non-neoplastic rectal mucosa to distinguish patients with UC-associated neoplasms from those without. Upper panels represented ROC curve analysis of these miRNAs methylation discriminating UC patients with cancer from those without cancer, with AUC values of 0.839 (95% CI: 0.736-0.914), 0.695 (95% CI: 0.578-0.796), 0.761 (95% CI: 0.648-0.852), 0.800 (95% CI: 0.692-0.884) and 0.795 (95% CI: 0.686-0.880), respectively. Lower panels demonstrated ROC curve analysis of these miRNAs methylation differentiating UC patients with neoplasia (combined cancer with dysplasia) from those without neoplasia, with AUC values of 0.700 (95% CI: 0.592-0.794), 0.632 (95% CI: 0.522-0.733), 0.605 (95% CI: 0.494-0.708), 0.771 (95% CI: 0.669-0.855) and 0.694 (95% CI: 0.586-0.788), respectively.

Next, we generated ROC curves to assess the possibility of using miR-1, -9, -124, -137 and -34b/c methylation in non-neoplastic rectum as biomarkers for patients with UC-associated neoplasia. Our ROC analyses revealed that methylation levels of these miRNAs robustly discriminated UC patients with cancer from those without cancer, with AUC values of 0.839 (95% CI: 0.736-0.914), 0.695 (95% CI: 0.578-0.796), 0.761 (95% CI: 0.648-0.852), 0.800 (95% CI: 0.692-0.884) and 0.795 (95% CI: 0.686-0.880), respectively 71.0%, respectively (FIG. 15). These results are further strengthened by univariate logistic regression analysis showing that methylation levels of all of these miRNAs and disease duration >8 years could be used as biomarkers for patients with UC-associated neoplasia (Table 18). Moreover, multivariate logistic analysis show high miR-137 methylation levels in rectal mucosa can be an independent predictive marker for UC patients harboring neoplasia (OR: 5.66, 95% CI: 1.37-23.47, P=0.0168; Table 18).

TABLE 18

Univariate and multivariate analyses of factors predictive of neoplasia in patients with ulcerative colitis

| Variables | Univariate analysis | | | Multivariate analysis | | |
|---|---|---|---|---|---|---|
| | OR | 95% CI | P | OR | 95% CI | P |
| Gender (Male vs Female) | 1.46 | 0.56-3.81 | 0.43 | | | |
| Age at onset (>29 yr vs. <29 yr)* | 1.23 | 0.49-3.12 | 0.66 | | | |
| Age at surgery (>38 yr vs. <38 yr)* | 1.65 | 0.65-4.21 | 0.29 | | | |
| Disease duration (>8 yr vs. <8 yr)* | 4.1 | 1.44-11.69 | 0.008 | 3.62 | 0.91-14.34 | 0.07 |
| Extent of disease (total colitis vs. left-side colitis) | 0.67 | 0.25-1.81 | 0.43 | | | |
| Inflammation score (mild vs. middle/severe) | 0.53 | 0.21-1.36 | 0.19 | | | |
| miR-1 methylation levels in rectum (>10 vs. <10)† | 2.93 | 1.07-8.00 | 0.036 | 0.44 | 0.10-2.06 | 0.3 |
| miR-9 methylation levels in rectum (>9 vs. <9)† | 4.63 | 1.25-17.17 | 0.022 | 1.78 | 0.36-8.79 | 0.48 |
| miR-124 methylation levels in rectum (>14 vs. <14)† | 6.21 | 1.41-27.26 | 0.016 | 1.93 | 0.33-11.19 | 0.47 |
| miR-137 methylation levels in rectum (>7 vs. <7)† | 7.74 | 2.66-22.55 | 0.0002 | 5.66 | 1.37-23.47 | 0.0168 |
| miR-34b/c methylation levels in rectum (>13 vs. <13)† | 5.25 | 1.61-17.08 | 0.006 | 3.11 | 0.80-12.08 | 0.1 |

OR: odds ratio;
CI: confidence interval;
rectum: non-neoplastic mucosa in rectum
*The median age at onset, median age at surgery and median disease duration are 29, 38, and 8 years, respectively.
†For miR-1, -9, -124, -137, and miR-34b/c, the cutoff values are 10, 9, 14, 7 and 13, respectively.

Figure 19:
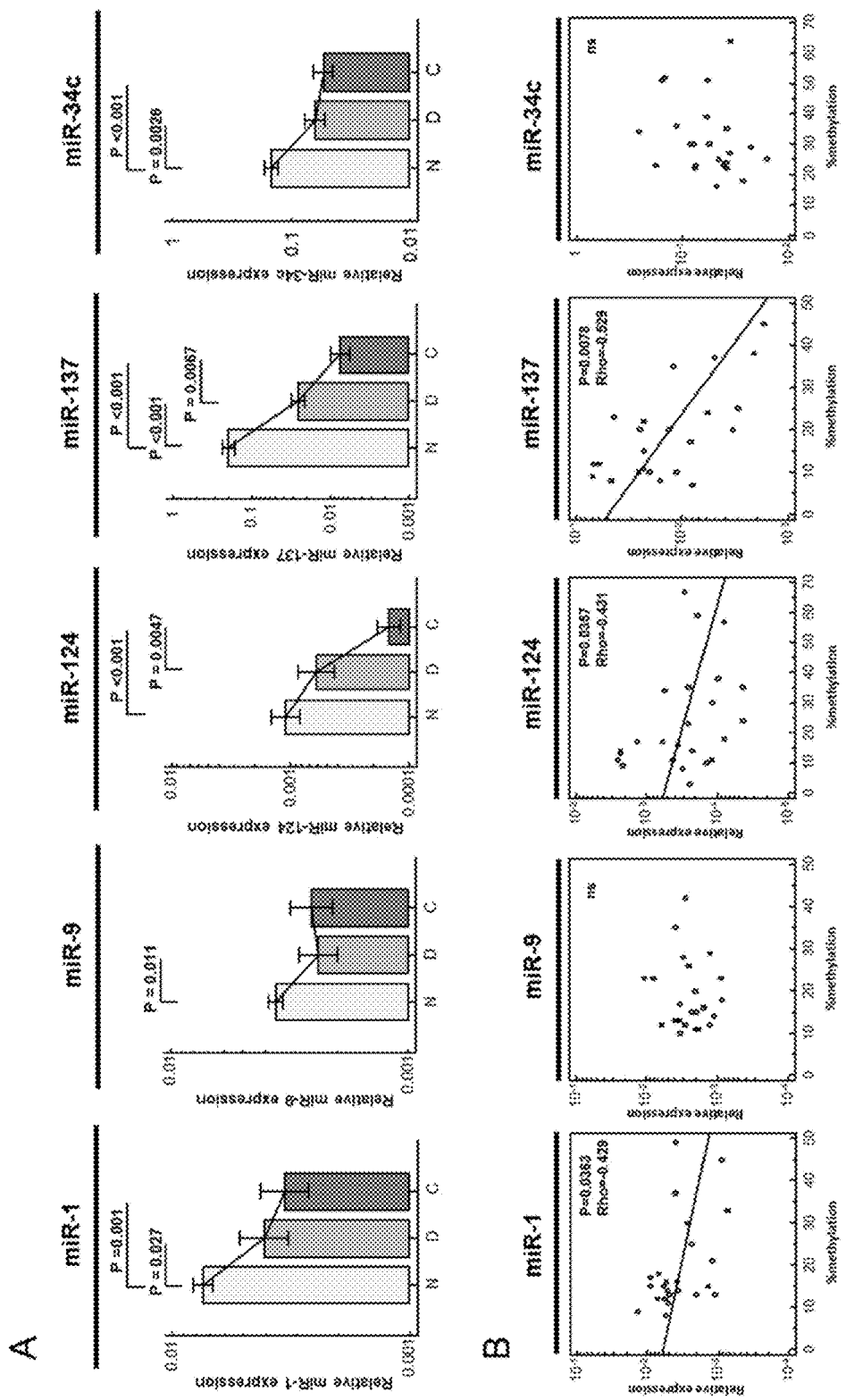
FIG. 19: Expression of miR-1, -9, -124, -137 and -34c in tissues from UC patients. (A) Expression levels of age-associated miRNAs in non-neoplastic UC mucosa (N; n=20), Dysplasia (D; n=12) and Cancer (C; n=13). Y-axis represents relative expression of miRNAs normalized to miR-16 expression. Statistically significant differences were determined using Mann-Whitney tests. (B) Scatter plots of miR-1, -9, -124, -137 and -34c showing correlations between expression levels (Y-axis: Log 10 scale) and methylation levels (X-axis) in samples obtained from UC patients with neoplasia. Negative correlations were found for miR-1, -124 and miR-137 by Spearman correlation (miR-1; $\rho=-0.43$, $P=0.036$, miR-124; $\rho=-0.43$, $P=0.036$, miR-137; $\rho=-0.53$, $P=0.008$).
Figure 20:
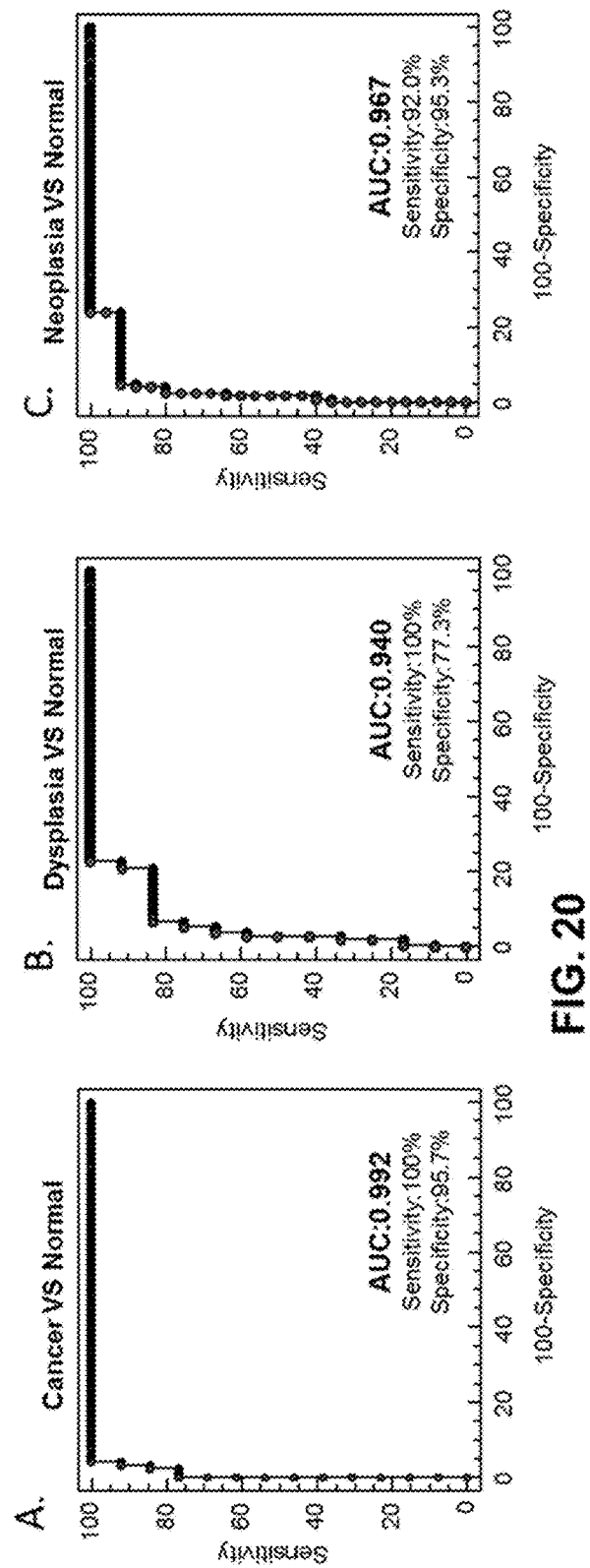
FIG. 20: Combination analysis of miR-1, -9, -124, -137, and -34b/c methylation levels discriminating cancer/dysplasia/neoplasia from non-neoplastic UC mucosa. Combine ROC analyses of methylation levels revealed an elevated AUC of 0.992 (95% CI: 0.970-0.999) with 100% sensitivity and 95.7% specificity in discriminating UC associated cancer (A), 0.940 (95% CI: 0.900-0.967) with 100% sensitivity and 77.3% specificity in discriminating UC associated dysplasia (B), and 0.967 (95% CI: 0.935-0.986) with 92.0% sensitivity and 95.3% specificity in discriminating UC associated neoplasia (C).
Figure 21:
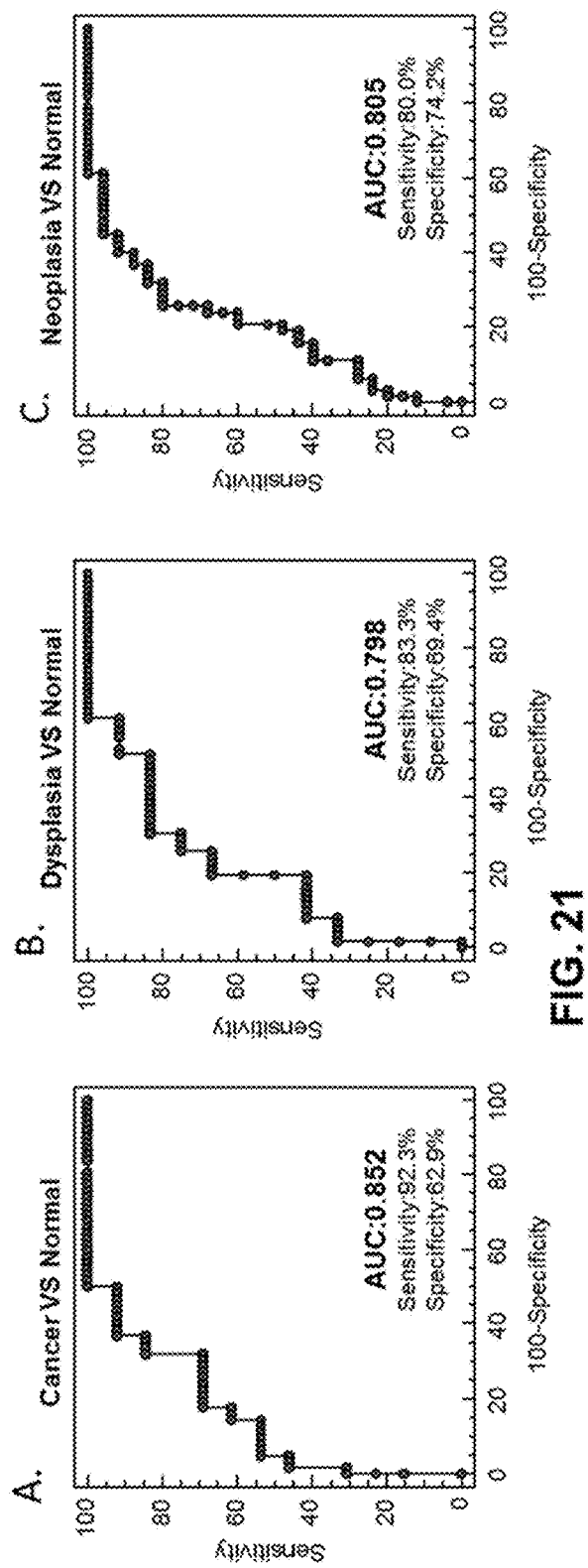
FIG. 21: Combination analysis of miR-1, -9, -124, -137, and -34b/c methylation levels in rectal non-neoplastic mucosa discriminating UC patients with cancer/dysplasia/neoplasia from those without. Combine ROC analyses of methylation levels revealed an elevated AUC of 0.852 (95% CI: 0.752-0.924) with 92.3% sensitivity and 62.9% specificity in discriminating UC associated cancer (A), 0.798 (95% CI: 0.689-0.883) with 83.3% sensitivity and 69.4% specificity in discriminating UC associated dysplasia (B), and 0.805 (95% CI: 0.706-0.882) with 80.0% sensitivity and 74.2% specificity in discriminating UC associated neoplasia (C).

(FIG. 15). More importantly from a screening perspective, only miR-137 methylation levels could differentiate UC patients with neoplasia (even dysplasia) from those without neoplasia, as evidenced by AUC value of 0.771 (95% CI: 0.669-0.855), with sensitivity and specificity of 76.0% and Inverse correlation between miR-1, -9, -124, -137 and -34b/c methylation and expression levels. To determine whether methylation of these miRNAs at a CpG island in the promoter region silences expression in UC tissue, we quantified expression levels of miR-1, -9, -124, -137 and -34c in dysplastic, and cancerous and non-neoplastic UC mucosa. As expected, compared to non-neoplastic mucosa, expression levels of all 5 miRNAs demonstrated stepwise decreases in dysplasia (miR-1: P=0.027; miR-9: P=0.011; miR-137: P<0.001; miR-34c: P=0.0026) and/or cancer (miR-1: P=0.001; miR-124: P<0.001; miR-137: P<0.001; miR-34c: P<0.001) (FIG. 19A). Methylation and expression of miR-1, -124, and -137 are significantly inversely correlated with UC-associated neoplasia (miR-1; ρ=−0.429, P=0.0363, miR-124; ρ=−0.431, P=0.0357, miR-137; ρ=−0.529, P=0.0078: FIG. 19B). In contrast, we cannot recognize a similar significant inverse relationship between miR-9 or miR-34b/c methylation levels and expression status in UC-associated neoplasia.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agirre, et al., *Cancer Res.* 69:4443-53, 2009.
Balaguer, et al., *Cancer Res.* 70:6609-18, 2010.
Boerno, et al., *Epigenomics.* 2(2):199-207, 2010.
Brentnall, et al., *Gastroenterology.* 107:369-78, 1994.
Calin, et al., *Nat Rev Cancer.* 6:857-66, 2006.
Danese et al., *Mini Rev Med Chem.* 6:771-784, 2006.
Deng, et al., *Oncol Lett.* 2:175-180, 2011.
Domenech, *Digestion.* 73 (Suppl. 1):67-76, 2006.
Eaden, et al., *Gut.* 48:526-35, 2001.
Flusberg, et al., *Nature Methods.* 7(6): 461-67, 2010.
Fujii, et al., *J Gastroenterol.* 38:1117-25, 2003.
Fujii, *Gut.* 54:1287-92, 2005.
Ghosh, *Novartis Found Symp.* 263:193-205 (2004.
Gionchetti et al., *World J Gastroenterol.* 12:3306-3313 (2006.
Hata, et al., *Br J Cancer.* 89:1232-6, 2003.
Hsieh, et al., *Cancer Res.* 58:3942-5, 1998.
Iorio, et al., *J Clin Oncol.* 27:5848-56, 2009.
Issa, *Crit Rev Oncol Hematol.* 32:31-43, 1999.
Issa, et al., *Cancer Res.* 61:3573-7, 2001.
Issa, et al., *Nat Genet.* 7:536-40, 1994.
Itzkowitz, et al., *Am J Physiol Gastrointest Liver Physiol.* 287:G7-17, 2004.
Kanaan, et al., *Hum Mutat.* 33:551-60, 2012.
Kornbluth et al., *Am J Gastroenterol.* 99:1371-85, 2004.
Kornbluth, et al., *Am J Gastroenterol.* 99:1371-85, 2004.
Kozaki, et al., *Cancer Res.* 68:2094-105, 2008.
Laird, *Nature Rev.* 11:191-203, 2010.
Laszlo, et al. *Proc Natl Acad Sci USA.* 110:18904-18909, 2013.
Lin & Huang, *Epigenomics.* 1(2): 331-45, 2009
Liu, et al., *Int J Cancer.* 128:1269-79, 2011.
Lu, et al., *Nature.* 435:834-8, 2005.
Lujambio, et al., *Cancer Res.* 67:1424-9, 2007.
Lujambio, et al., *Proc Natl Acad Sci USA.* 105:13556-61, 2008.
Nakamura et al., *World J Gastroenterol.* 12:4628-4635 (2006.
Risques, et al., *Gastroenterology.* 135:410-8, 2008.
Sands, *Surg Clin North Am.* 86:1045-1064 (2006.
Sato, et al., *Cancer Res.* 62:1148-51, 2002.
Schreiber, et al. *Proc Natl Acad Sci USA.* 110:18910-18915, 2013.
Tominaga, et al., *Clin Cancer Res.* 11:8880-5, 2005.
Toyota, et al., *Cancer Res.* 68:4123-32, 2008.
Toyota, et al., *Proc Natl Acad Sci USA.* 96:8681-6, 1999.
Ullman, et al., *Inflamm Bowel Dis.* 15:630-8, 2009.
Velayos, et al., *Gastroenterology.* 139:1511-8, 2010.
Vogelstein, et al., *N Engl J Med.* 319:525-32, 1988.
Watanabe, et al., *Clin Colorectal Cancer.* 10(22):134-41, 2011.
Watanabe, et al., *Int J Oncol.* 38(1):201-7, 2011.
Wilting, et al., *Mol Cancer.* 9:167, 2010.
Wu, et al., *Gastroenterology.* 135:1624-1635 e24, 2008.
Zisman, et al., *J Gastroenterol.* 14:2662-9, 2008.

What is claimed is:

1. A method for determining increased methylation levels in genes from a sample from a patient with ulcerative colitis comprising measuring in the sample increased methylation levels for genes encoding miR-1 and miR-9 compared to a control or reference methylation level for the genes.

2. The method of claim 1, further comprising treating the patient for dysplasia or cancer.

3. The method of claim 1, wherein the sample is a tissue sample, a whole blood sample, a urine sample, a saliva sample, a serum sample or a fecal sample.

4. The method of claim 1, wherein the sample is a tissue sample.

5. The method of claim 1, wherein the sample is a rectum sample, a colon sample or a cecum sample.

6. The method of claim 1, wherein the sample is a fresh, frozen or preserved sample or a fine needle aspirate.

7. The method of claim 1, wherein the sample is a formalin-fixed, paraffin-embedded (FFPE) sample.

8. The method of claim 1, wherein the method comprises isolating nucleic acids in the sample.

9. The method of claim 1, wherein the method comprises assaying nucleic acids in the sample.

10. The method of claim 9, wherein assaying nucleic acids comprises a methylation assay of the promoter in the gene.

11. The method of claim 10, wherein the methylation assay comprises next generation sequencing, single-molecule real-time sequencing, mass spectrometry, bisulfite sequencing, combined bisulfite restriction analysis (COBRA), Southern blotting, single nucleotide primer extension (SNuPE), methylation-specific PCR (MSPCR), restriction landmark genomic scanning for methylation (RLGS-M), HpaII-tiny fragment enrichment by ligation-mediated PCR (HELP assay), CpG island microarray, ChIP-chip (chromatin immnuprecipitation-on-chip), ChIP-seq (chromatin immunoprecipitation-sequencing), methylated DNA immunoprecipitation (MeDIP), or a microarray-based methylation profiling.

12. The method of claim 1, further comprising recording the methylation levels or risk in a tangible medium.

13. The method of claim 1, further comprising reporting the methylation levels or risk to the patient, a health care payer, a physician, an insurance agent, or an electronic system.

14. The method of claim 1, further comprising monitoring the ulcerative colitis patient for colorectal dysplasia or cancer.

15. The method of claim 1, further comprising measuring in the sample increased methylation levels for genes encoding miR-137, miR-124 and miR-34b/c compared to a control or reference methylation level for the genes.

16. A method for treating a patient comprising administering treatment for dysplasia or cancer to an ulcerative colitis patient determined to have increased methylation levels in genes encoding miR-1, miR-9, miR-137, miR-124 and miR-34b/c compared to a control or reference methylation level for the genes.

17. A method for measuring methylation levels in genes from a sample from a patient comprising measuring methylation levels for genes encoding miR-1 and miR-9 and comparing the measured levels to a control or reference methylation level for the genes.

18. The method of claim 17, wherein the control or methylation level is the methylation level in normal tissue, a non-cancerous tissue, a non-dysplastic tissue, or a non-ulcerative colitis tissue.

19. The method of claim 17, wherein the sample is a rectum sample, a colon sample or a cecum sample.

* * * * *